(12) United States Patent
Taylor-Fishwick et al.

(10) Patent No.: US 7,355,024 B2
(45) Date of Patent: Apr. 8, 2008

(54) REGULATORY SEQUENCES FOR MODULATION OF INGAP EXPRESSION AND REPORTER CONSTRUCTS

(75) Inventors: David A. Taylor-Fishwick, Suffolk, VA (US); Aaron I. Vinik, Norfolk, VA (US)

(73) Assignee: GMP Endotherapeutics, Inc., Fort Lauderdale, FL (US)

( * ) Notice: Subject to any disclaimer, the term of this patent is extended or adjusted under 35 U.S.C. 154(b) by 668 days.

(21) Appl. No.: 10/339,767

(22) Filed: Jan. 9, 2003

(65) Prior Publication Data

US 2003/0207301 A1 Nov. 6, 2003

Related U.S. Application Data

(60) Provisional application No. 60/388,315, filed on Jun. 14, 2002, provisional application No. 60/361,073, filed on Mar. 1, 2002, provisional application No. 60/346,898, filed on Jan. 11, 2002.

(51) Int. Cl.
*C07H 21/04* (2006.01)
(52) U.S. Cl. ..................................... 536/23.5
(58) Field of Classification Search ..................... None
See application file for complete search history.

(56) References Cited

U.S. PATENT DOCUMENTS 5,834,590 A 11/1998 Vinik et al.
5,840,531 A 11/1998 Vinik et al.
6,090,620 A * 7/2000 Fu et al. ..................... 435/325

FOREIGN PATENT DOCUMENTS

WO WO9626215 A1 8/1996

OTHER PUBLICATIONS

Rafaeloff, R. et al., "Cloning and Sequencing of the Pancreatic Islet Neogenesis Associated Protein (INGAP) Gene and Its Expression in Islet Neogenesis in Hamsters", *J. Clin. Invest.*, 1997, vol. 99, No. 9, pp. 2100-2109.
Taylor-Fishwick, D.A., et al., "Cloning genomic INGAP: a Reg-related family member with distinct transcriptional regulation sites", *Biochem. Biophys. Acta*, 2003, vol. 1638, No. 1, pp. 83-89.
Boshart, M., et al., "A very strong enhancer is located upstream of an immediate early gene of human cytomegalovirus", *Cell*, 1985, vol. 41, No. 2, pp. 521-530.
Nordeen, S.K., "Luciferase Reporter Gene Vectors for Analysis of Promoters and Enhancers", *BioTechniques*, 1988, vol. 6, No. 5, pp. 454-458.
Mir, L.M., "Therapeutic Perspectives of In vivo Cell electropermeabilization", *Bioelectrochemistry*, 2000, vol. 53, No. 1, pp. 1-10.

* cited by examiner

*Primary Examiner*—G. R. Ewoldt
(74) *Attorney, Agent, or Firm*—Michael J. Keller; Lott & Friedland, P.A.

(57) ABSTRACT

A an isolated mammalian INGAP 5"-regulatory region comprising at least about nucleotides 1-3137 of SEQ ID NO: 2 (SEQ ID NO: 23).

1 Claim, 13 Drawing Sheets

Predicted regulatory sites within the INGAP regulatory region nucleotide sequence SEQ ID NO: 23 (bases 1-3123)

| Start | End | Score | Predicted Promoter Sequence |
|---|---|---|---|
| 229 | 279 | 0.87 | TTCCTCAGCTTTATAACTAGGGTCTCTCTGCTTTCACTATGTCAGGTCAA |
| 1758 | 1808 | 0.98 | CCTGTTCATTAAAAAACTGCAGGAAAGTTGTGATTTATAATGCAACTGC |
| 2000 | 2050 | 0.94 | TATATATATATATATATATATCAGCACAGTGAAACAGTTAATA |
| 2009 | 2059 | 1.00 | ATATATATATATATATATATCAGCACAGTGGAAACAGTTAATAACATTTTAG |
| 2058 | 2108 | 0.95 | GCATATATACTATAGAAAATAGGAGGCTGGAAGGGGCTCAGCAGTTAAT |
| 2478 | 2528 | 0.82 | CTGTTTTCCTTAAAATCCTGGCTACAGTGTTGACTCAGTGGTTGCTTTA |
| 2653 | 2703 | 0.97 | TTAAATTTTTAAATGGGCATAAATTGCAGCTATTCCTACAGAAGTCAGT |
| 3083 | 3133 | 0.86 | TCAGATCCTATTAAAATAAAAAGCACAGTCGTCTCTTTCCTGGCAAAACACCCC |
| 3585 | 3635 | 0.96 | CCATATGTTAAATAAAAGGAGCATTCTCATGGGAAATCTTCTTCATCCTG |
| 4198 | 4248 | 0.84 | TATGCTCATGTATAATACTGTGTNCACACTCCTCGAACACACACATAC |
| 5507 | 5557 | 0.94 | GCTGACCCTTCATGTATAACTGGGAGAGGAACCCCCTCTATTGCTGACCGTG |
| 6451 | 6501 | 0.88 | ATCAAACATTTATATATAATATGGGTTAAAAATATTACTTCAATGGACTTAC |

Figure 4

5'-GTA ATA CGA CTC ACT ATA GGG CAC GCG TGG TCG ACG GCC CGG GCT GGT-3'
3'-H$_2$N-CC CGA CCA-PO$_4$-5'

| Gene Walk Fragment | GSP1 | GSP2 |
|---|---|---|
| 19_3 (1,1423) | INGEN 21_3 (1464, 1482) | INGEN 19_3 (1401, 1423) |
| 16_3 (1355,1876) | INGEN 15_3 (1929, 1948) | INGEN 16_3 (1855, 1876) |
| 14_3 (1769, 2168) | INGEN 13_3 (2177, 2200) | INGEN 14_3 (2147, 2168) |
| 8_3 (1973, 2565) | INGEN 7_3 (2666, 2689) | INGEN 8_3 (2544, 2565) |
| 2_3 (2162,3470) | INGEN 1_3 (3475,3501) | INGEN 2_3 (3444,3470) |
| 1_2 (3241,3734) | INGEN 1_2 (3241, 3266) | INGEN 2_2 (3330, 3350) |
| 14_5 (5544, 6586) | INGEN 13_5 (5463, 5485) | INGEN 14_5 (5544, 5563) |

| Genomic PCR Fragment | LEFT PRIMER | RIGHT PRIMER |
|---|---|---|
| 1_1 L/R (3475, 5976) | INGAP1_1L (3475, 3492) | INGAP1_1R (5957, 5976) |
| 2_1 L/R (4470, 5923) | INGAP2_1L (4470, 4488) | INGAP2_1R (5905, 5923) |

Figure 7

REGULATORY SEQUENCES FOR MODULATION OF INGAP EXPRESSION AND REPORTER CONSTRUCTS

This application incorporates by reference provisional applications Ser. No. 60/388,315 filed Jun. 14, 2002, Ser. No. 60/361,073 filed Mar. 1, 2002, and Ser. No. 60/346,898 filed Jan. 11, 2002.

FIELD OF THE INVENTION

The invention relates to the field of assays for the detection of factors that modulate gene expression. Specifically, the invention relates to reporter constructs and methods for identifying agents that modulate the expression of the INGAP gene.

BACKGROUND OF THE INVENTION

Islet neogenesis gene associated protein (INGAP protein) has been identified as a pancreatic acinar cell protein that can induce islet cell neogenesis from progenitor cells resident in the pancreas in a manner that recapitulates islet development during normal embryogenesis. INGAP is unique in its ability to stimulate growth and differentiation of islets of Langerhans from precursor cells associated with pancreas. These islets evolve a mature insulin secretory profile capable of responding to perturbations in blood glucose in a physiologic manner. This potential anti-diabetic therapeutic has been shown to demonstrate homology across several species and to exert a biological response.

Pancreatic islet cell mass is lost in type 1 diabetes mellitus, a disease in which a progressive autoimmune reaction results in the selective destruction of insulin-producing β-cells. In type 2 diabetes mellitus, so-called adult-onset disease, but also increasingly a condition in young overweight people, the β-cell mass may be reduced by as much as 60% of normal. The number of functioning β-cells in the pancreas is of critical significance for the development, course, and outcome of diabetes. In type I diabetes, there is a reduction of β-cell mass to less than 2% of normal. Even in the face of severe insulin resistance as occurs in type II diabetes, the development of diabetes only occurs if there is inadequate compensatory increase in β-cell mass. Thus, the development of either of the major forms of diabetes can be regarded as a failure of adaptive β-cell growth and a subsequent deficiency in insulin secretion. Stimulating the growth of islets and β-cells from precursor cells, known as islet neogenesis, is an attractive approach to the amelioration of diabetes. There is need in the art for methods to identify agents that can modulate the expression of INGAP, whether in animals or in cultured cells.

BRIEF SUMMARY OF THE INVENTION

It is an object of the invention to provide a reporter construct containing the 5'-regulatory region from mammalian INGAP gene.

It is another object of the invention to provide methods for identifying agents which modulate INGAP expression.

It is another object of the invention to provide a nucleic acid or fragment of INGAP 5'-regulatory region.

It is another object of the invention to provide methods for increasing INGAP expression.

It is another object of the invention to provide a kit for modulating INGAP expression.

These and other objects of the invention are provided by one or more of the embodiments described below.

In one aspect of the invention a reporter construct is provided. The reporter construct comprises a regulatory region nucleotide sequence and a nucleotide sequence encoding a detectable product. In one aspect of the invention, the reporter construct is provided in a vector. The regulatory region nucleotide sequence is linked to the nucleotide sequence encoding a detectable product. The regulatory region nucleotide sequence may comprise one or more fragments of 5' regulatory region of the INGAP genomic sequence, SEQ ID NO:23, or it may comprise the entire length of the 5' regulatory region. In one embodiment of the reporter construct, a promoter element is interposed between the regulatory region nucleotide sequence and the nucleotide sequence encoding a detectable product. The promoter element may be selected from the promoter elements present in the INGAP regulatory sequence. Alternatively, the promoter element present in the vector comprising the reporter construct may be used. The detectable product encoded by the said nucleotide sequence encoding a detectable product could be either a nucleic acid or a protein. The detectable product need not be the INGAP gene nucleic acid or protein.

In another embodiment of the invention, a method identifying agents that modulate INGAP expression is provided. The method comprises contacting a cell with a test agent, wherein the cell comprises a reporter construct of the present invention. Expression of the detectable nucleic acid or protein product in the cell is determined. A test agent is identified as a modulator of INGAP expression if the test agent modulates expression of the detectable product in the cell.

In another embodiment of the invention, an isolated nucleic acid comprising the genomic sequence of the hamster INGAP gene (SEQ ID NO: 2), or a fragment thereof is provided.

According to another embodiment of the invention, an in vitro method for identifying agents that modulate INGAP expression is provided. The method comprises contacting a test agent with a reporter construct of the present invention in a cell-free system that allows for transcription and translation of a nucleotide sequence. Expression of the detectable product is determined. The substance is identified as a modulator of INGAP expression if the test substance modulates expression of the detectable product.

According to another embodiment of the invention, an in vitro method for identifying an agent that modulate INGAP expression is provided. The method comprises contacting a test agent with a nucleic acid of the invention. Binding of the test agent to the nucleic acid is determined. The test agent is identified as a modulator of INGAP expression if the test agent binds to the nucleic acid.

According to another embodiment of the invention a method for increasing INGAP expression is provided. An effective amount of a factor that stimulates INGAP expression directly or indirectly, for example cytokines, chemokines, growth factors, or pharmacological agents, is administered to a mammal in need of increased INGAP expression.

According to another embodiment of the invention a kit for modulating INGAP expression is provided. The kit comprises a modulator of INGAP expression and instructions for using the modulator of INGAP expression to modulate INGAP expression.

According to another embodiment of the invention a method for modulating INGAP expression in a mammal to treat a disease state related to reduced islet cell function is provided. The method comprises the step of administering to the mammal an effective amount of a modulator of INGAP expression whereby the level of INGAP expression in the mammal is modified.

All documents cited are, in relevant part, incorporated herein by reference; the citation of any document is not to be construed as an admission that it is prior art with respect to the present invention.

BRIEF DESCRIPTION OF THE DRAWINGS

FIG. 4 shows the predicted transcription start sites within the 5'-regulatory region (SEQ ID NO: 1) of the hamster INGAP gene (SEQ ID NO: 2). The predicted start site is indicated by a boldface nucleotide. The start and end nucleotide numbers are indicated for the promoter sequence. The numbers refer to nucleotide numbers of the hamster INGAP gene (SEQ ID NO: 2)

FIG. 5 shows the adapter primer structure and sequence used in gene walking. Adapter primer 1 (API) and adapter primer 2 (AP2) are shown.

FIGS. 6 and 7 show the strategy for reconstructing the hamster INGAP gene. The hamster INGAP gene was reconstructed using the technique of gene walking. Shown are the fragments and the gene specific primers (GSP1 and GSP2) used in PCR amplification for gene walking. Fragments were joined together using unique restriction enzyme sites within each fragment. The nucleotide sequences of the individual primers are listed in Table 2.

DETAILED DESCRIPTION OF THE INVENTION

Definitions

Figure 1:
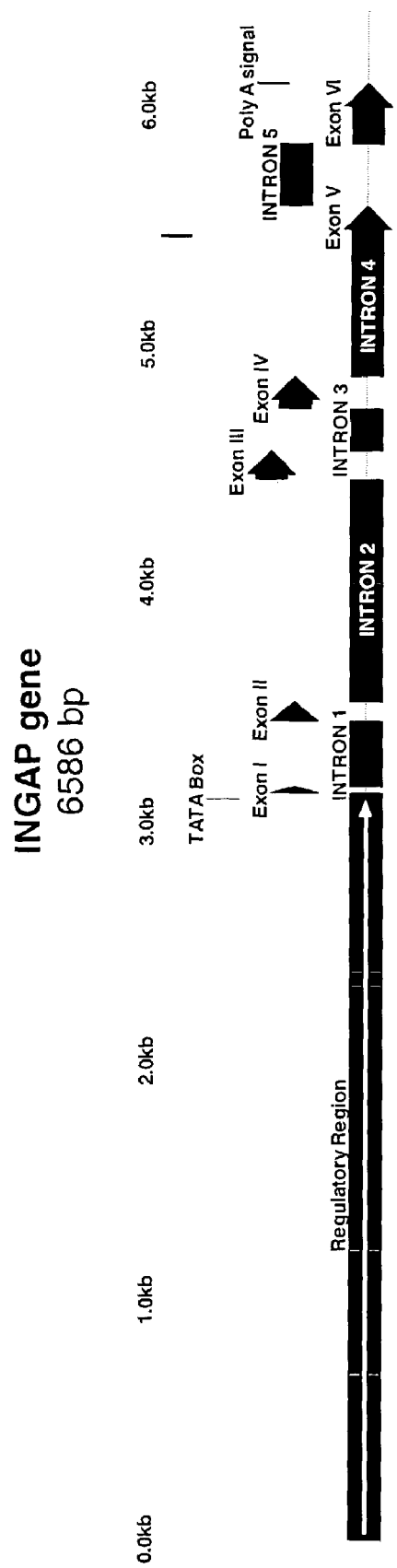
FIG. 1 shows the annotation of the hamster INGAP gene structure. The boundaries of introns 1-5 are listed in Table 1.

It must be noted that as used herein and in the appended claims, the singular forms "a", "an", and "the" include plural references unless the context clearly dictates otherwise.

The term "promoter" is used to define the region of a gene at which initiation and rate of transcription are controlled. It contains the site at which RNA polymerase binds and also sites for the binding of regulatory proteins, e.g. transcription factors, repressors, etc. In order to differentiate between the transcription initiation site and other sites that modulate rate of transcription, promoter region is generally subdivided into "minimal promoter element" and "regulatory region". The term "minimal promoter element" or sometimes simply referred to as "promoter" therefore may include TATA box, GC-rich sequence and CAAT box; while "regulatory region" is usually a long stretch of nucleotide sequence where transcription factors and other factors bind. Most eukaryotic genes have long regulatory regions where many different transcription factors bind. The expression or the lack of expression of a given gene in a given cell type, tissue, organ, or an organism is governed by the interactions that take place on its regulatory region.

The term "transcription factor" is used to describe the proteins that bind short stretches of DNA in the regulatory regions of a gene. Transcription factors may interact with each other as well as RNA polymerase. Thus, transcription factors may bind hormones or second messengers, DNA, RNA, other transcription factors, or other proteins. They may activate or inhibit transcription of a given gene. Transcription factors are also sometimes referred to as "enhancers" or "repressors". Transcription factor binding sites can be used to identify agents that bind to the 5'-regulatory region of the gene and modulate the gene's expression.

The term "reporter" is used to describe a coding sequence attached to a heterologous promoter or enhancer elements and whose product, either nucleic acid or protein, is easily detected and is quantifiable. Some common reporter genes include β-galactosidase (lacZ), chloramphenicol acetyltransferase (cat), β-glucuronidase (GUS), and green fluorescent protein (GFP).

A "reporter construct" is a piece of nucleic acid that includes a promoter element and a reporter gene housed in a suitable vector plasmid DNA. Regulatory region nucleotide sequences may be cloned 5' of the promoter element to determine if they contain transcription factor binding sites. The reporter construct-containing vector is introduced into a cell that contains many transcription factors. Activation of the reporter gene by transcription factors may be monitored by detection and quantification of the product of the reporter gene.

The term "agent" is used here to essentially describe any means to modulate INGAP expression. Agent may be a chemical compound, a biological agent, or a physical force, a mechanical contraption, or any combinations thereof.

INGAP Promoter and Regulatory Region

It is a discovery of the present inventors that INGAP gene is regulated by a 5'-regulatory region that is susceptible to modulation by many known transcription factors, including PMA and LIF.

It is a further discovery of the present invention that the 5'-regulatory region nucleotide sequence of the INGAP gene may be used in screening assays to identify agents capable of modulating the INGAP gene expression. These modulating agents have potential as therapeutic agents for treating pathological conditions including, but not limited to, diabetes mellitus, both type 1 and type 2, endocrine and non-endocrine hypoplasia, hypertrophy, adenoma, neoplasia, and nesidioblastosis.

Mammalian INGAP, like most genes, has a 5'-regulatory region followed by introns and exons. The sequence of a mammalian (Hamster sp.) INGAP gene is provided as SEQ ID NO: 2. FIG. 1 details the relative location of the 5'-regulatory region, the introns and the exons of the hamster INGAP gene. The boundaries of introns 1-5 and the location of the TATA-box and the poly-A signal are listed in Table 1.

TABLE 1

| Description | Position In INGAP Gene (SEQ ID NO: 2) |
|---|---|
| TATA-Box | 3094 |
| INTRON 1 | 3150-3426 |
| INTRON 2 | 3508-4442 |
| INTRON 3 | 4562-4735 |
| INTRON 4 | 4874-5459 |
| INTRON 5 | 5587-5843 |
| Poly-A Signal | 6098-6103 |

Figure 2:
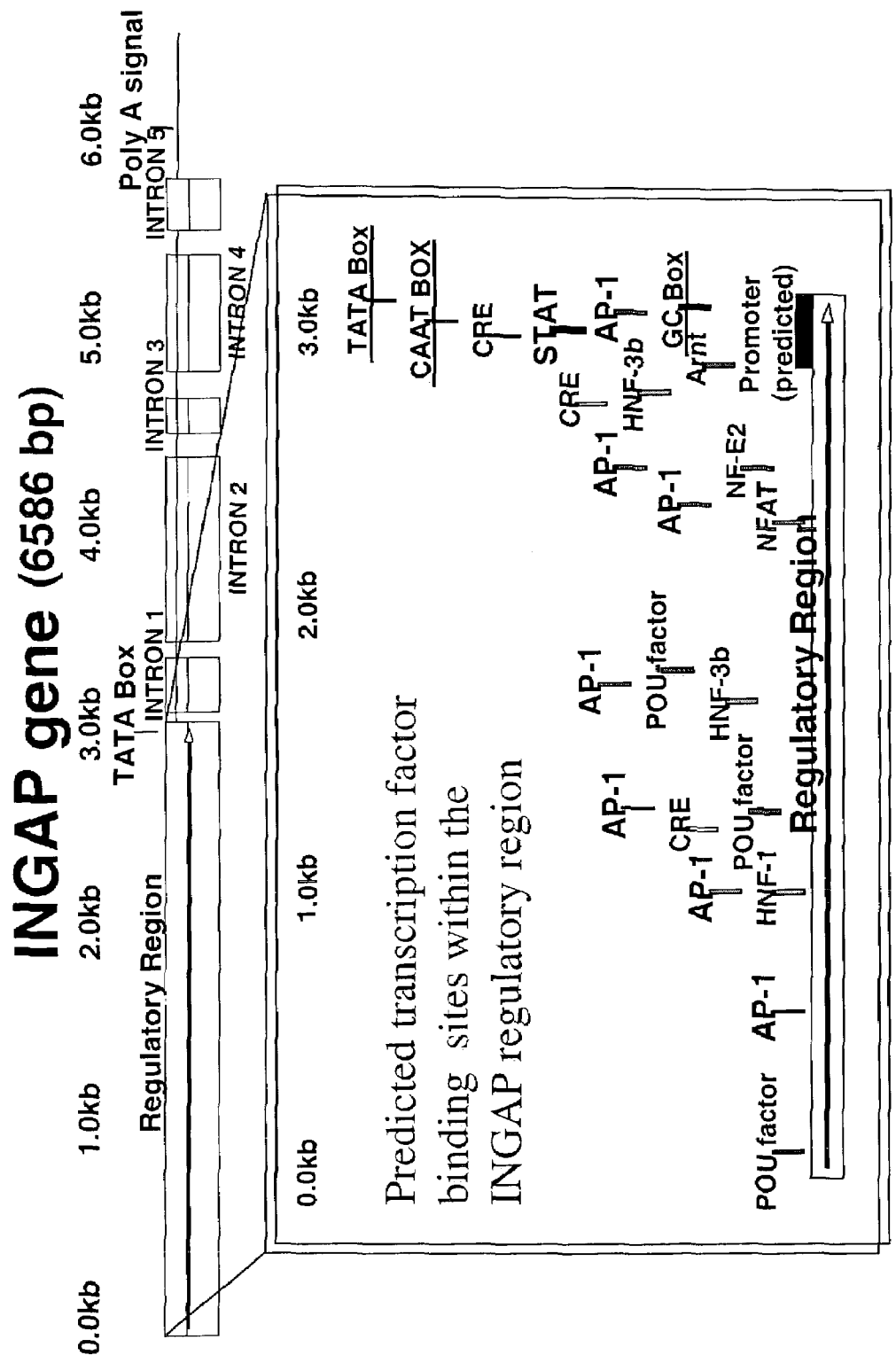
FIG. 2 shows an overview of the 5'-regulatory region of the hamster INGAP gene (nucleotides 1-3137 of SEQ ID NO: 2) showing many well known and well-characterized transcription factor binding sites. The minimal promoter element contains the regions noted with an underline (CAAT-box, TATA-box, and GC-box).
Figure 3:
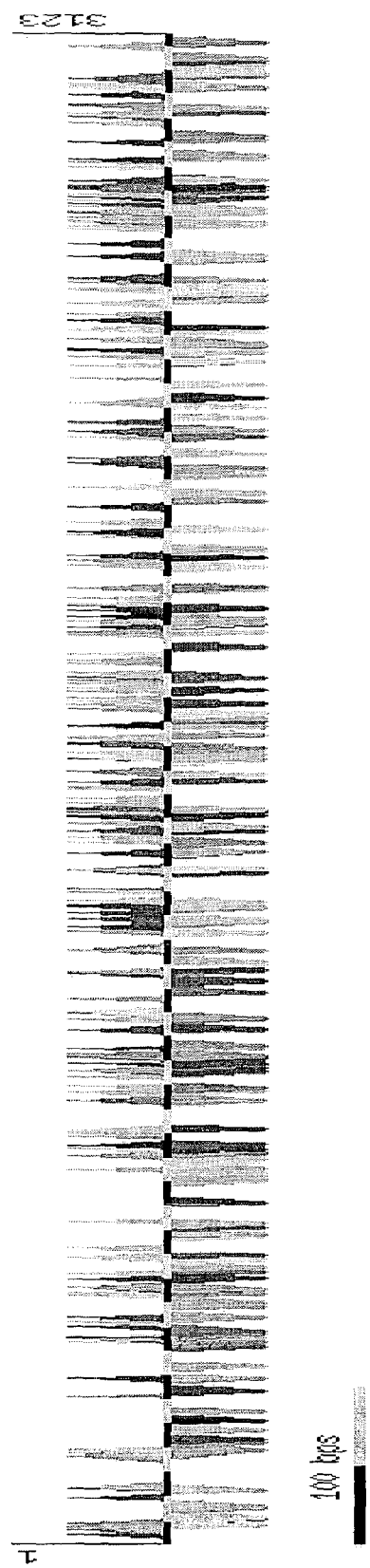
FIG. 3 shows a schematic of many well known and well-characterized transcription factor-binding sites for nucleotides 1-3123 of the 5'-regulatory region (SEQ ID NO: 1) of the hamster INGAP gene. Table 3 further describes these transcription factor-binding sites.

The nucleotide sequence of the 5'-regulatory region including the promoter elements of mammalian INGAP, is shown partially in SEQ ID NO: 1, and completely in SEQ ID NO: 2 and 23 (nucleotides 1-3137 of SEQ ID NO: 2). Nucleotides 1-3120 of SEQ ID NO: 1 are identical to nucleotides 1-3120 of SEQ ID NO: 2 and SEQ ID NO: 23. An overview of the 5'-regulatory region is shown in FIG. 2. Representative transcription enhancer/repressor binding sites are shown also in FIG. 2. Predicted transcription enhancer/repressor binding sites for nucleotides 1-3123 of the 5'-regulatory region are shown in FIG. 3. Table 3 at the end of the specification details these transcription factors and their binding sites, and their locations in the regulatory region. Potential transcription factor binding analysis was done using MatInspector professional™, which is a bioinformatics software that utilizes a library of matrix descriptions for transcription factor binding sites to locate matches in sequences of unlimited length (Quandt, K., Frech, K., Karas, H., Wingender, E., Werner, T. (1995) Nucleic Acids Res. 23, 4878-4884).

Table 3 lists predicted binding proteins (Further Information) based upon their classification into functionally similar matrix families (Family/matrix). The DNA sequence predicted to bind the protein (Sequence), whether sense or antisense DNA (Str) and location of the sequence in SEQ ID NO: 2, (Position) are listed. Further the similarity to the consecutive highest conserved nucleotides of a matrix (Core sim.) and similarity to all nucleotides in that matrix (Matrix sim.) along with the optimized value (Opt) defined in a way that a minimum number of matches is found in non-regulatory test sequences are also listed. Details to the algorithms used in MatInspector professional™ is referenced:

OPT: This matrix similarity is the optimized value defined in a way that a minimum number of matches are found in non-regulatory test sequences (i.e. with this matrix similarity the number of false positive matches is minimized). This matrix similarity is used when the user checks "Optimized" as the matrix similarity threshold for MatInspector professional™.

Family: Each matrix belongs to a so-called matrix family, where functionally similar matrices are grouped together, eliminating redundant matches by MatInspector professional™ professional (if the family option was selected). E.g. the matrix family V$NFKB includes 5 similar matrices for NFkappaB (V$NFKAPPAB.01, V$NFKAPPAB.02, V$NFKAPPAB.03, V$NFKAPPAB50.01, V$NFKAPPAB65.01) as well as 1 matrix for the NFkappaB related factor c-Rel (V$CREL.01).

Matrix: The MatInspector professional™ matrices have an identifier that indicates one of the following seven groups: vertebrates (V$), insects (I$), plants (P$), fungi (F$), nematodes (N$), bacteria (B$), and other functional elements (O$); followed by an acronym for the factor the matrix refers to, and a consecutive number discriminating between different matrices for the same factor. Thus, V$OCT1.02 indicates the second matrix for vertebral Oct-1 factor.

Core Sim: The "core sequence" of a matrix is defined as the (usually 4) consecutive highest conserved positions of the matrix. The core similarity is calculated as described here. The maximum core similarity of 1.0 is only reached when the highest conserved bases of a matrix match exactly in the sequence. More important than the core similarity is the matrix similarity which takes into account all bases over the whole matrix length.

Matrix Sim: The matrix similarity is calculated as described here. A perfect match to the matrix gets a score of 1.00 (each sequence position corresponds to the highest conserved nucleotide at that position in the matrix), a "good" match to the matrix usually has a similarity of >0.80. Mismatches in highly conserved positions of the matrix decrease the matrix similarity more than mismatches in less conserved regions.

Another aspect of the invention provides for a reporter construct. Reporter constructs contain a 5' regulatory region nucleotide sequence fragment of SEQ ID NO: 23 (e.g., an enhancer and/or repressor binding site containing region), a promoter element (which may or may not be from INGAP regulatory region nucleotide sequence, SEQ ID NO: 23), and a reporter gene. The 5'-regulatory region nucleotide sequence is positioned upstream of the reporter gene. In order to determine the identity of various transcription factors that bind the 5' regulatory region nucleotide sequence and to elucidate their binding locations within the 5' regulatory nucleotide sequence of the INGAP gene, the region may be mapped using deletion analysis. One or more fragments of the regulatory region nucleotide sequence may be initially analyzed for their responses to various transcription factor activators. Once, a region of interest is determined, further fine mapping may be carried out where DNA from different locations within the regulatory region could be combined to make a more robust, and responsive reporter construct. DNA sequences, such as INGAP 5'-regulatory region DNA or a fragment thereof, can be manipulated by methods well known in the art. Examples of such techniques include, but are not limited to, polymerase chain reaction (PCR), restriction enzyme endonuclease digestion, ligation, and gene walking. Cloning fragments of DNA, such as 5'-regulatory regions is well known in the art.

Another approach to quantify the expression levels of a gene is to measure transcription of the gene. PCR-ELISA may be used to capture transcripts onto a solid phase using biotin or digoxigenin-labelled primers, oligonucleotide probes (oligoprobes) or directly after incorporation of the digoxigenin into the transcripts (Watzinger, F. and Lion, T. (2001) *Nucleic Acids Res.*, 29, e52). Once captured, the transcripts can be detected using an enzyme-labeled avidin or anti-digoxigenin reporter molecule similar to a standard ELISA format. Another approach is to employ real-time PCR to detect the transcript of the reporter gene (Mackay, I. M. and Nitsche, A., Nucleic Acids Res. Mar. 15, 2002; 30(6), 1292-305). In real-time PCR fluorogenic nucleotides are used and progress of the transcript is monitored in real-time as the polymerase transcribes the reporter gene.

The promoter element in the reporter construct may or may not be from the same gene as the 5'-regulatory region. As an example, the enhancer/repressor region from the INGAP 5'-regulatory region, or a fragment of the enhancer/repressor region from the INGAP 5'-regulatory region, may be cloned upstream of a heterologous minimal promoter element, e.g., the minimal CMV promoter (Boshart et al., 1985) and the promoters for TK (Nordeen, 1988), IL-2, and MMTV.

Transcription of a gene begins around the minimal promoter. FIG. 4 shows the predicted transcription start sites for mammalian INGAP gene (SEQ ID NO: 2). SEQ ID NO: 2 was analyzed using "Neural Network Promoter Prediction" program designed by Martin Reese to identify eukaryotic promoter recognition elements such as TATA-box, GC-box, CAAT-box, and the transcription start site. These promoter elements are present in various combinations separated by various distances in sequence. The program is available on the Internet and is located at http://www.fruitfly.org/seq_tools/promoter.html.

The reporter construct can be used to identify agents that modulate, either alone or in combination, the expression of INGAP. Some such agents may modulate expression of INGAP by binding to the regulatory region directly while others may regulate expression of transcription factors that bind to the INGAP regulatory region.

The reporter construct can be transfected into a host cell in vitro, or in vivo through the pancreatic duct, either transiently or stably, and a test agent introduced to the assay system. Examples of test agents include, but are not limited to organic and inorganic chemical agents, carbohydrates, proteins, oligonucleotides, cholecystokinin, mechanically induced pressure, and agents which cause a pancreatic duct obstruction. Expression of the reporter gene product can be determined by an assay appropriate for the reporter gene employed. Examples of such assays include, but are not limited to a luminescent assay for β-galactosidase or luciferase, an enzymatic assay for chloramphenicol acetyl transferase, and fluorescence detection for fluorescent proteins. Such assays are well known in the art, and a skilled artisan will be able to select an appropriate assay for the chosen reporter. A test agent is identified as a modulator of INGAP expression if the test agent modulates expression of the reporter gene product. Preferably the level of increase or decrease is at least 50%, 100%, 200%, 500%, or 1000%, but any statistically significant change can be an indicator of modulatory activity. A skilled artisan may also determine reporter gene product expression in untreated cells, and in treated and untreated cells transfected with a promoter-less reporter gene only. Such determinations can be used to determine background levels of expression.

Test agents can also be obtained by fractionating pancreatic secretion fluids. A pancreatic duct obstruction can be used as an exemplary method of harvesting pancreatic secretion fluids. The pancreatic secretion fluids can be fractionated by methods well known in the art. Examples include high-pressure liquid chromatography (HPLC), size exclusion chromatography, hydrophobic interacting columns, and density gradient centrifugation. Individual fractions can be tested for agents that modulate reporter gene expression using a method described herein. The individual fractions can be further fractionated to identify agents that modulate reporter gene expression. The identified test agents can be used to modulate the expression of INGAP.

A host cell can be any cell suitable for transfection and maintenance in a suitable assay system. Examples of suitable cells include, but are not limited to, mammalian cells, human cells, mouse cells, rat cells, monkey cells, dog cells, bovine cells, and porcine cells. Preferably the cells used will be human cells. The cells could be either transformed cells line or primary cells. Whole organ explants may also be used where the regulation may be monitored over many different cell types. Many methods exist in the art for transfecting or infecting cells with reporter construct DNA. Such methods include, but are not limited to, lipofection, electroporation, calcium phosphate precipitation, DEAE dextran, gene guns, and modified viral techniques (e.g., recombinant adenovirus or recombinant retrovirus). The skilled artisan can readily choose a method suitable for use with a given cell type and assay system.

The reporter construct can also be introduced in vivo directly into cells of the pancreas. Examples of methods to introduce the reporter construct into pancreatic cells in vivo include pancreatic duct retrograde perfusion and in vivo electroporation (Mir, 2001). The reporter construct encodes a reporter gene product that is readily measured in vivo. A test agent can be administered systemically or locally, and expression of the reporter gene in vivo can be determined by an assay appropriate for the particular reporter employed. Examples of such include a fluorescence assay for green fluorescent protein.

Methods for identifying agents that modulate INGAP expression can also be accomplished in vitro. The reporter construct can be contacted with a test agent in vitro under conditions sufficient for transcription and/or translation of the reporter gene. Components such as rabbit reticulocyte lysates or wheat germ extracts can be utilized for such a method. Subsequently, the expression level of the reporter gene can be determined as described above utilizing an appropriate assay for a given reporter gene. A test agent is identified as a modulator of INGAP expression if the test agent modulates expression of the reporter gene. Threshold levels of change can be set by the practitioner as discussed above.

A test agent can alternatively be contacted with an isolated and purified INGAP 5'-regulatory DNA molecule and one can determine if the test agent binds to the DNA molecule. Test agents can be a chemical agent, a protein, or a nucleic acid. Appropriate INGAP 5'-regulatory DNA molecules would include nucleotides 1-6586 of SEQ ID NO: 2, the 5'-regulatory region DNA (SEQ ID NO: 1, or SEQ ID NO: 23), or any fragment of the 5'-regulatory region, preferably a fragment which contains one or more enhancer/repressor binding sites. Methods to determine binding of the test agent to the fragment of DNA are well known in the art, e.g., electrophoretic mobility shift assay (EMSA). See for example Sambrook et al., MOLECULAR CLONING: A LABORATORY MANUAL, 2d ed., 1989, at pages 9.50-9.51. Fragments of the 5'-regulatory region can be obtained by methods well known in the art using the disclosed sequence (SEQ ID NO: 2). Examples of such methods include, PCR, restriction enzyme digestion, and chemical synthesis. Any fragment of DNA within the 5'-regulatory region (SEQ ID NO: 1, or 23) can be used. The exact location that an agent binds can be determined for example by utilizing smaller fragments to map precisely the binding site for the test agent. Test agents that bind in the assay can be further tested in other assays that require modulatory activity.

An agent that causes an increase or decrease in reporter gene expression can be used as a modulator of INGAP expression. The modulator can be administered to a mammal in need of such modulation. Examples of mammals that may need INGAP expression modulation are those with reduced pancreatic function, in particular reduced islet cell function. Such mammals include those who have diabetes mellitus, impaired glucose tolerance, impaired fasting glucose, hyperglycemia, obesity, and pancreatic insufficiency.

An agent that is identified as a modulator of INGAP expression can be supplied in a kit to treat diseases associated with reduced islet cell function. The kit would comprise in single or divided containers, in single or divided doses a modulator of INGAP expression. Written instructions may be included for using the modulator of INGAP expression. The instructions may simply refer a reader to another location such as a website or other information source.

Agents that cause an increase in reporter gene expression can be used to increase INGAP expression to treat a disease state related to reduced islet cell function.

Agents that cause a decrease in reporter gene expression can be used to decrease INGAP expression to treat a disease state related to hyperactivity of islet cells or a disease where reduced INGAP expression is desirable. Examples of such agents include, but are not limited to, PMA, LIF, interleukin-6, Oncostatin M, and ciliary neurotropic factor. Agents can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, rectal, or pancreatic duct retrograde perfusion. Agents for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the mammal. Agents for intravenous, intramuscular, intra-arterial, transdermal, and subcutaneous injections can be formulated using pharmaceutically acceptable carriers well known in the art in dosages suitable for injection into the mammal.

Agents for intranasal, topical, and rectal administration can be formulated using pharmaceutically acceptable carriers well known in the art in dosages suitable for surface administration to the mammal. Mammals in need of an increase in INGAP expression include for example, mammals with diabetes mellitus, impaired glucose tolerance, impaired fasting glucose, hyperglycemia, obesity, and pancreatic insufficiency. Mammals in need of a decrease in INGAP expression include for example, mammals with hypoglycemia.

The following examples are offered by way of illustration and do not limit the invention disclosed herein.

EXAMPLES

Example 1

Hamster INGAP Genomic Sequence and Structure

The hamster INGAP genomic sequence and structure was determined by gene walking (Clontech) and DNA sequencing. Gene walking is a method for walking upstream toward a promoter or downstream in genomic DNA from a known sequence, such as cDNA. This method utilizes four uncloned, adapter-ligated genomic fragment libraries. The manufacturer's recommended protocol is followed with one notable exception; hamster genomic DNA was used to create the uncloned, adapter-ligated genomic fragment libraries.

To create uncloned, adapter ligated genomic fragment libraries, genomic DNA was purified from hamster cells. Four separate aliquots were thoroughly digested with PvuII, StuI, DraI, or EcoRV. Following digestion, inactivation of the restriction enzymes, and dephosphorylation, each separate pool of DNA fragments was ligated to an adapter, see FIG. 5. The adapter was phosphorylated to provide the requisite phosphate group for a ligation reaction. Also note that the 3-prime side of the short adapter contains an amine group to prevent the adapters from forming concatamers.

Figure 6:
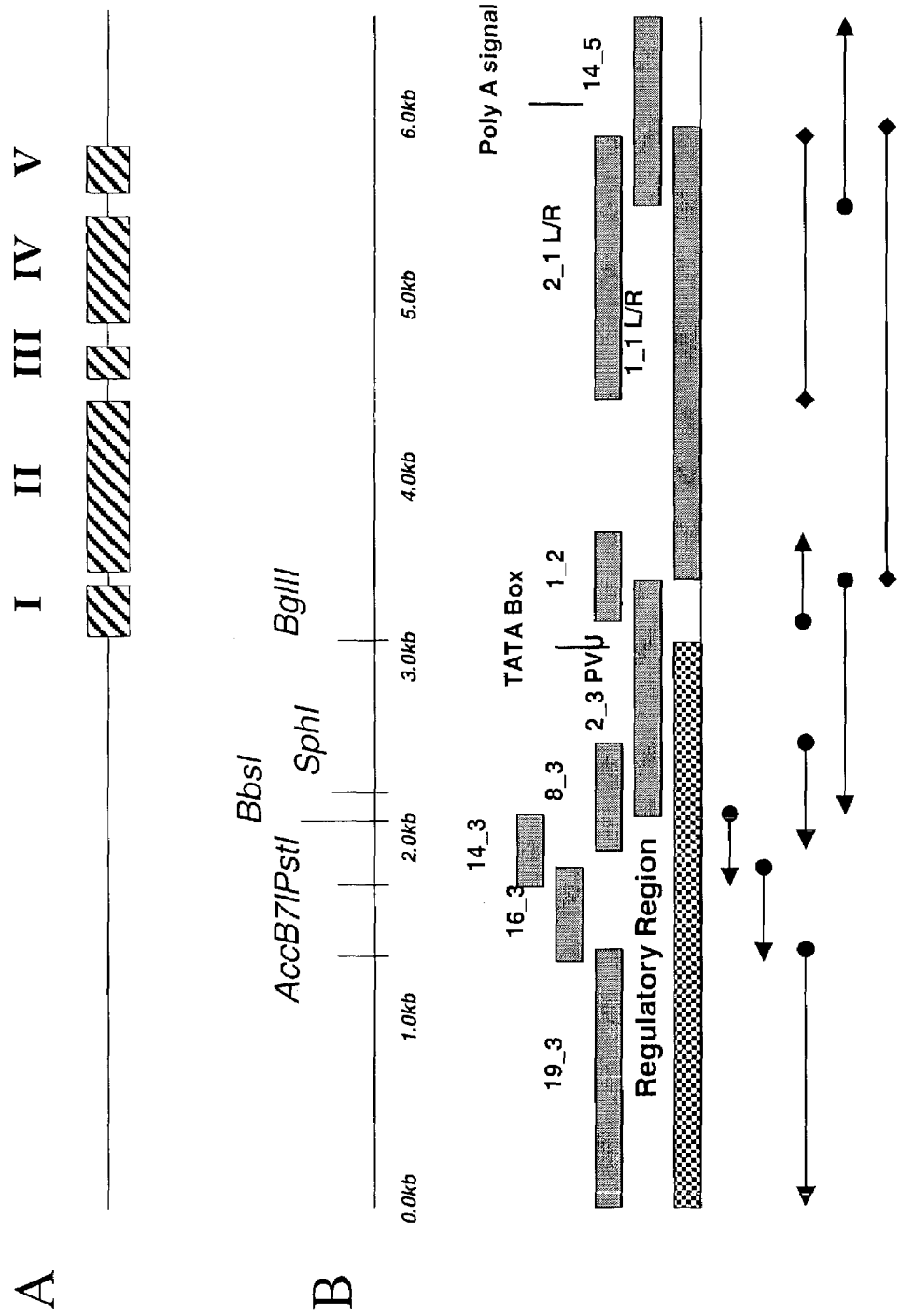

Two gene specific primers (GSP1 and GSP2) were designed for each region of known sequence (i.e., the exons of the INGAP gene). See FIG. 6 for fragment location and GSP1 and GSP2 location. The gene specific primers were designed as reverse PCR primers for all fragments except fragments 1_2 and 14_5. The gene specific primers for fragments 1_2 and 14_5 were designed as forward primers. Adapter primer 1 (API) and adapter primer 2 (AP2) (FIG. 5) were forward PCR primers for all fragments except fragments 1_2 and 14_5, which were reverse PCR primers. The outer gene specific primer (GSP1) was used with adapter primer 1 in a PCR reaction. To increase specificity, a second, nested PCR was set up using the inner gene specific primer (GSP2) and adapter primer 2. A small aliquot of the first reaction served as template for the second reaction. Gene specific PCR primers utilized for gene walking are listed in Table 2 and the strategy used to build the INGAP genomic sequence is shown in FIGS. 6 and 7. The arrowheads in FIG. 6 represent the adapter primers (AP1 and AP2), while the circles represent the gene specific primers (GSP1 and GSP2).

TABLE 2

| NAME (LOCATION) | SEQUENCE | |
|---|---|---|
| INGEN 21_3 (1464, 1482) | 5'-ACAAGCAATCTAGAGATGG-3' | (SEQ ID NO: 3) |
| INGEN 19_3 (1401, 1423) | 5'-GTTCAGCTATGTTCATAGCAGGG-3' | (SEQ ID NO: 4) |
| INGEN 16_3 (1855, 1876) | 5'-GTCTGTATGACTGTGTGGGAAG-3' | (SEQ ID NO: 5) |
| INGEN 15_3 (1929, 1948) | 5'-GCACTTGAACTCAATGGCTC-3' | (SEQ ID NO: 6) |
| INGEN 14_3 (2147, 2168) | 5'-GAACCACCTGACATGGGTGATG-3' | (SEQ ID NO: 7) |
| INGEN 13_3 (2177, 2200) | 5'-GGGCATCGTATCATCTGGTTACAG-3' | (SEQ ID NO: 8) |
| INGEN 8_3 (2544, 2565) | 5'-GGTTCAAAAAAGCTGCTTCAAC-3' | (SEQ ID NO: 9) |
| INGEN 7_3 (2666, 2689) | 5'-GGAATAGCTGCAATTTATGCCCAT-3' | (SEQ ID NO: 10) |
| INGEN 4_3 (2833, 2858) | 5'-CTTAGGAACATTCAGGCAGCCTCCTG-3' | (SEQ ID NO: 11) |
| INGEN 3_3 (2866, 2891) | 5'-GTTGCCCTCTGCCACGTGTCAAGTTC-3' | (SEQ ID NO: 12) |
| INGEN 2_3 (3444, 3470) | 5'-CATCCAAGACATCCTACAGAGGGTCAT-3' | (SEQ ID NO: 13) |
| INGEN 1_3 (3475, 3501) | 5'-CCCAAGAAAGGAACATCAGGCAGGAAA-3' | (SEQ ID NO: 14) |
| INGEN 2_2 (3330, 3350) | 5'-CCAAATGAGTGCTTCCCTGAA-3' | (SEQ ID NO: 15) |
| INGEN 1_2 (3241, 3266) | 5'-GCAGCACTCTGAAACTCAGTAGAGTT-3' | (SEQ ID NO: 16) |
| INGEN 14_5 (5544, 5563) | 5'-GCTGCTGACCGTGGTTATTG-3' | (SEQ ID NO: 17) |
| INGEN 13_5 (5463 5485) | 5'-ACACTACCCAACGGAAGTGGATG-3' | (SEQ ID NO: 18) |
| INGAP1_1L (3475, 3492) | 5'-TTTCCTGCCTGATGTTCC-3' | (SEQ ID NO: 19) |
| INGAP1_1R (5957, 5976) | 5'-TCATACTTGCTTCCTTGTCC-3' | (SEQ ID NO: 20) |
| INGAP2_1L (4470, 4488) | 5'-CTTCACGTATAACCTGTCC-3' | (SEQ ID NO: 21) |
| INGAP2_1R (5905, 5923) | 5'-ATTAGAACTGCCCTAGACC-3' | (SEQ ID NO: 22) |

The PCR fragments were sequenced to determine the nucleotide sequence of the INGAP 5'-regulatory region; the introns, the intron/exon junctions, and the 3-prime polyadenylation regions. The nucleotide sequence of hamster INGAP genomic DNA is shown in SEQ ID NO: 2.

Example 2

Cloning Hamster INGAP 5'-Regulatory Region Fragment into a Reporter Construct

To construct the INGAP 5'-regulatory region, individual PCR fragments were joined together at unique restriction sites located within two adjoining fragments. FIGS. 6 and 7 detail the strategy used to piece the INGAP 5'-regulatory region together. Fragments 8_3 and 2_3 were joined at a unique SphI site; 14_3 and 8_3 were joined at a unique BbsI site; 16_3 and 14_3 were joined at a unique PstI site. The nucleotide sequence of hamster INGAP 5'-regulatory region DNA is shown in SEQ ID NO: 1 and 23 in the sequence listing.

Figure 8:
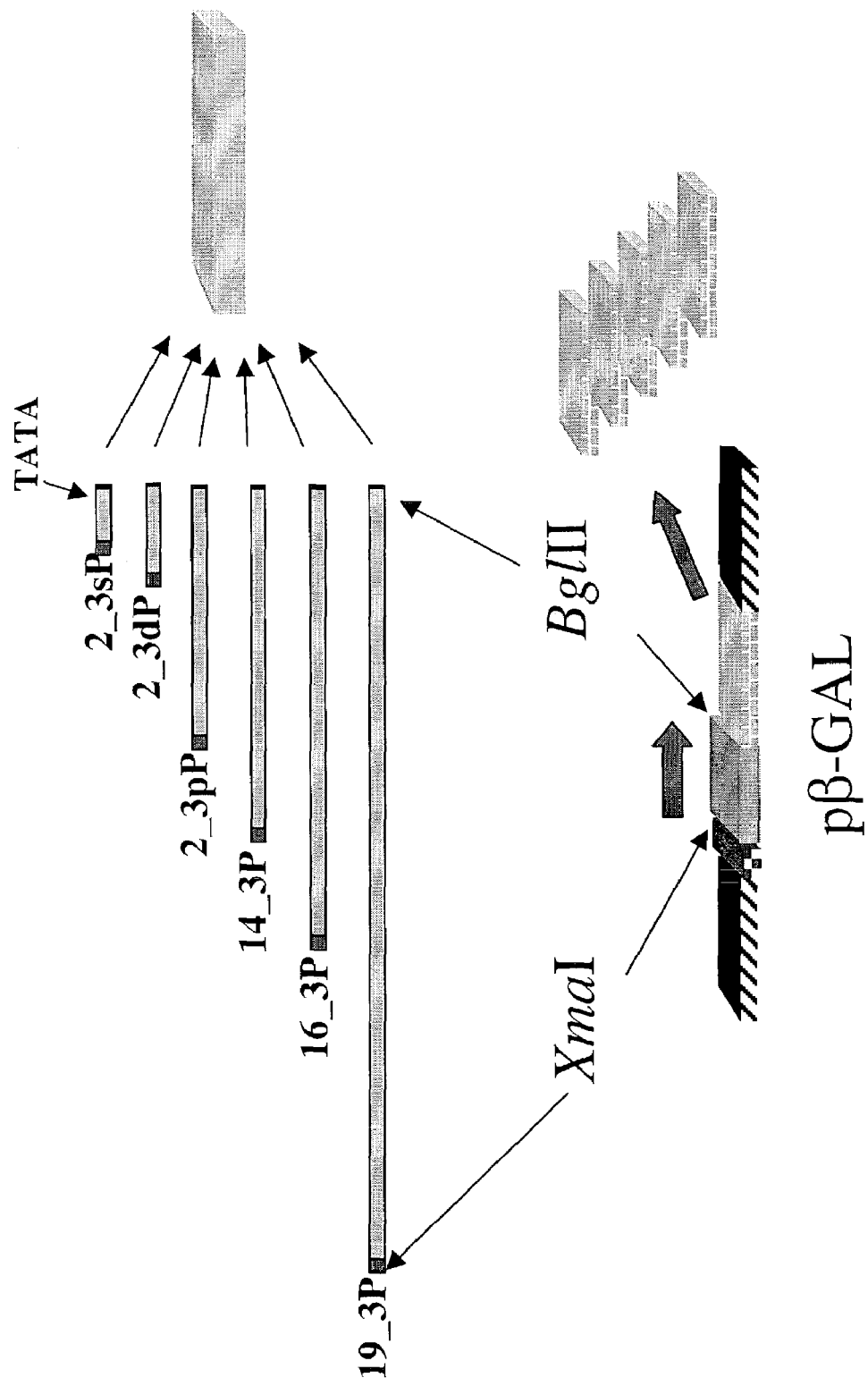
FIG. 8 shows the fragments of INGAP 5'-regulatory region, which were cloned into pβGal-basic upstream of a P-galactosidase reporter gene. The labels on the left refer to the nucleotide fragments of SEQ ID NO: 23 which were cloned upstream of pβGal-basic.

The hamster INGAP 5'-regulatory region or a fragment of the 5'-regulatory region was cloned into a reporter plasmid, pβGal-Basic (Clontech). The 5'-regulatory region or fragments were cloned utilizing the unique XmaI site from the gene walking adapter primer and a unique BglII site located at the 3-prime side of the regulatory region. FIG. 8 details the fragments cloned into pβGal-Basic. The sizes of the fragments are indicated to the right of the fragments and are expressed as the number of nucleotides of the fragment.

Example 3

Assay System to Screen for Factors that Modulate the Expression of INGAP

Promoter analysis of INGAP identified a number of potential promoter-proximal regulatory sites including the consensus transcription factor binding sites; cAMP response element (CRE), AP-1 and STAT. Promoter-fragment reporter-gene constructs were transiently transfected into 293T cells and co-transfection of secretory alkaline phosphatase was used to normalize for transfection efficiency.

Figure 9A:
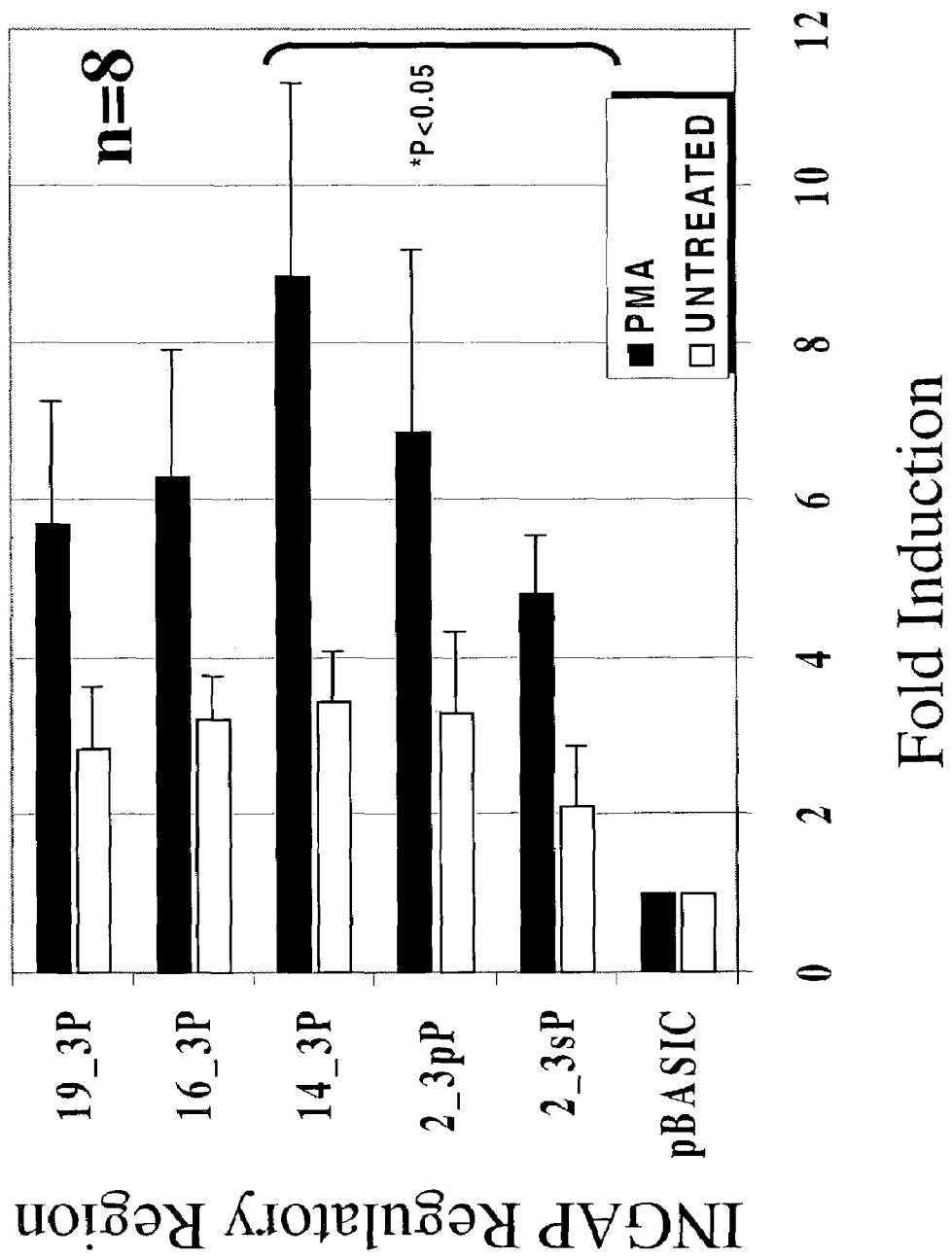
FIG. 9A shows reporter activity in human embryonic kidney cells (293T) transfected with a reporter construct that contains various fragments of the 5'-regulatory region (SEQ ID NO: 23) of hamster INGAP DNA cloned upstream of a β-galactosidase reporter gene (pβGal-basic), or in a reporter construct which contains no INGAP DNA. The cells are stimulated with phorbol myristate acetate. Promoter activity is assessed by determining the level of β-galactosidase present in the cell using a β-galactosidase luminescent assay.

Reporter constructs containing INGAP 5'-regulatory region fragments 2_3sP (SEQ ID NO: 37), 2_3dP (SEQ ID NO: 38), 2_3pP (SEQ ID NO: 36), 14_3P (SEQ ID NO: 34), 16_3P (SEQ ID NO: 31), or 19_3P (SEQ ID NO: 23) were transfected into human cells. The pβGal-Basic plasmid without the hamster INGAP DNA was also transfected into human cells as a control to measure the level of endogenous reporter activity. Two days following transfection, the cells were treated with PMA for 24 hours or were untreated. To determine the level of promoter activity, the amount of β-galactosidase gene product was determined using a luminescent assay for β-galactosidase. FIG. 9A shows that construct 14_3P activated the INGAP expression the most, followed by 2_3pP, and 16_3P.

Figure 9B:
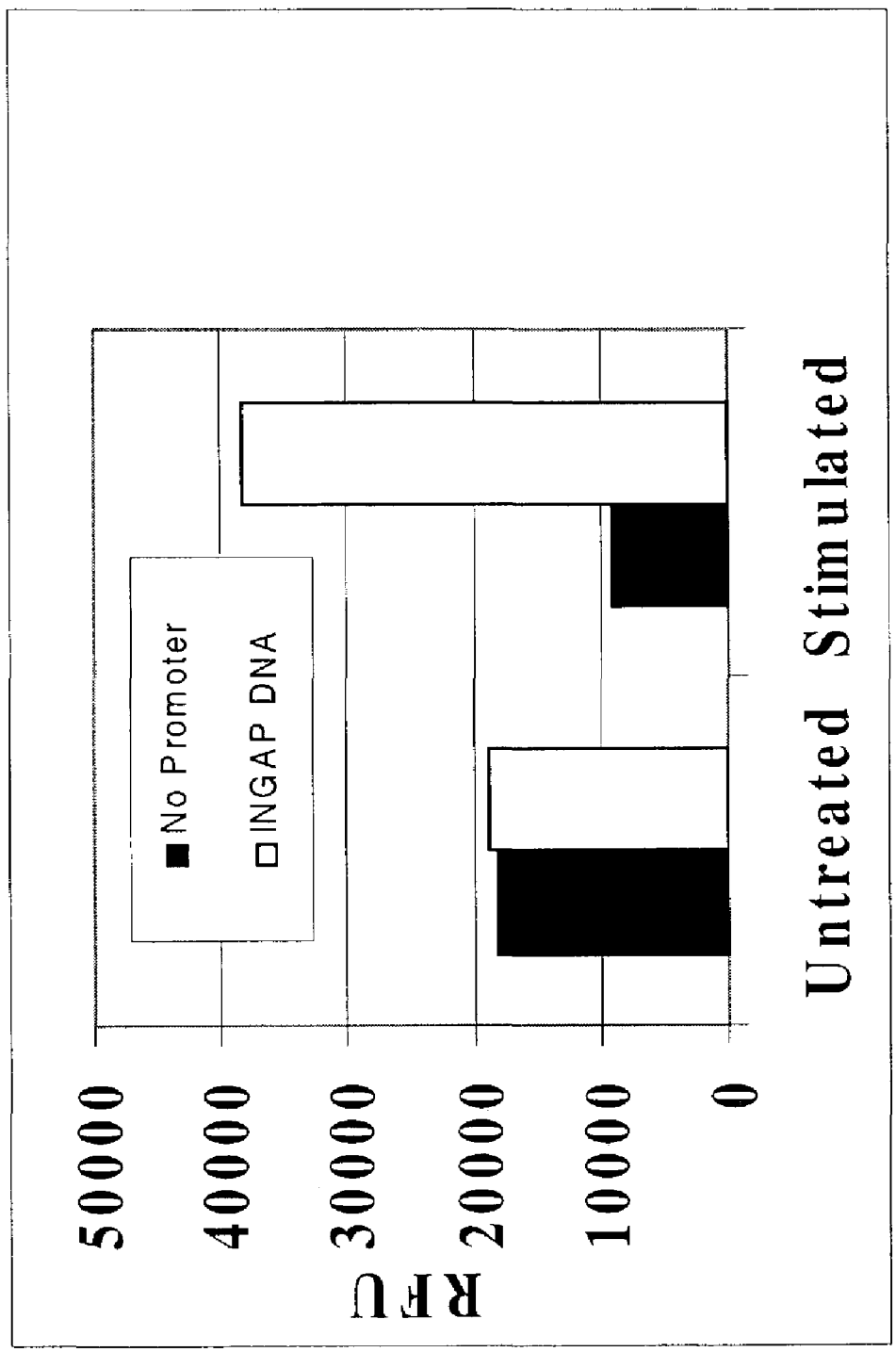
FIG. 9B shows reporter activity in human embryonic kidney cells (293T) transfected with a reporter construct that contains nucleotides 2030 to 3137 of the 5'-regulatory region (SEQ ID NO: 23) of hamster INGAP cloned upstream of a β-galactosidase reporter gene, or in a reporter construct which contains no INGAP DNA. The cells are stimulated with leukemia inhibitory factor. Promoter activity is assessed by determining the level of P-galactosidase present in the cell using a β-galactosidase luminescent assay.

Reporter construct containing INGAP 5'-regulatory region DNA nucleotides 2030 to 3120 was transfected into human cells. The pβGal-Basic plasmid without the hamster INGAP DNA was also transfected into human cells as a control to measure the level of endogenous reporter activity. Two days following transfection, the cells were treated with LIF for 24 hours or were untreated. To determine the level of promoter activity, the amount of β-galactosidase gene product was determined using a luminescent assay for β-galactosidase. FIG. 9B shows the results. LIF was determined to increase the activity of the 5'-regulatory region of mammalian INGAP. Forskolin (an activator of cAMP/CREB/CRE) did not modulate gene expression (data not shown).

It is important to note that when present in human cells, the hamster INGAP 5'-regulatory region is transactivated by the human transcription factors. Thus, linked to a reporter gene, the 5'-regulatory region of hamster INGAP creates a sensitive assay system to screen for factors that modulate the expression of INGAP.

Example 4

Figure 10:
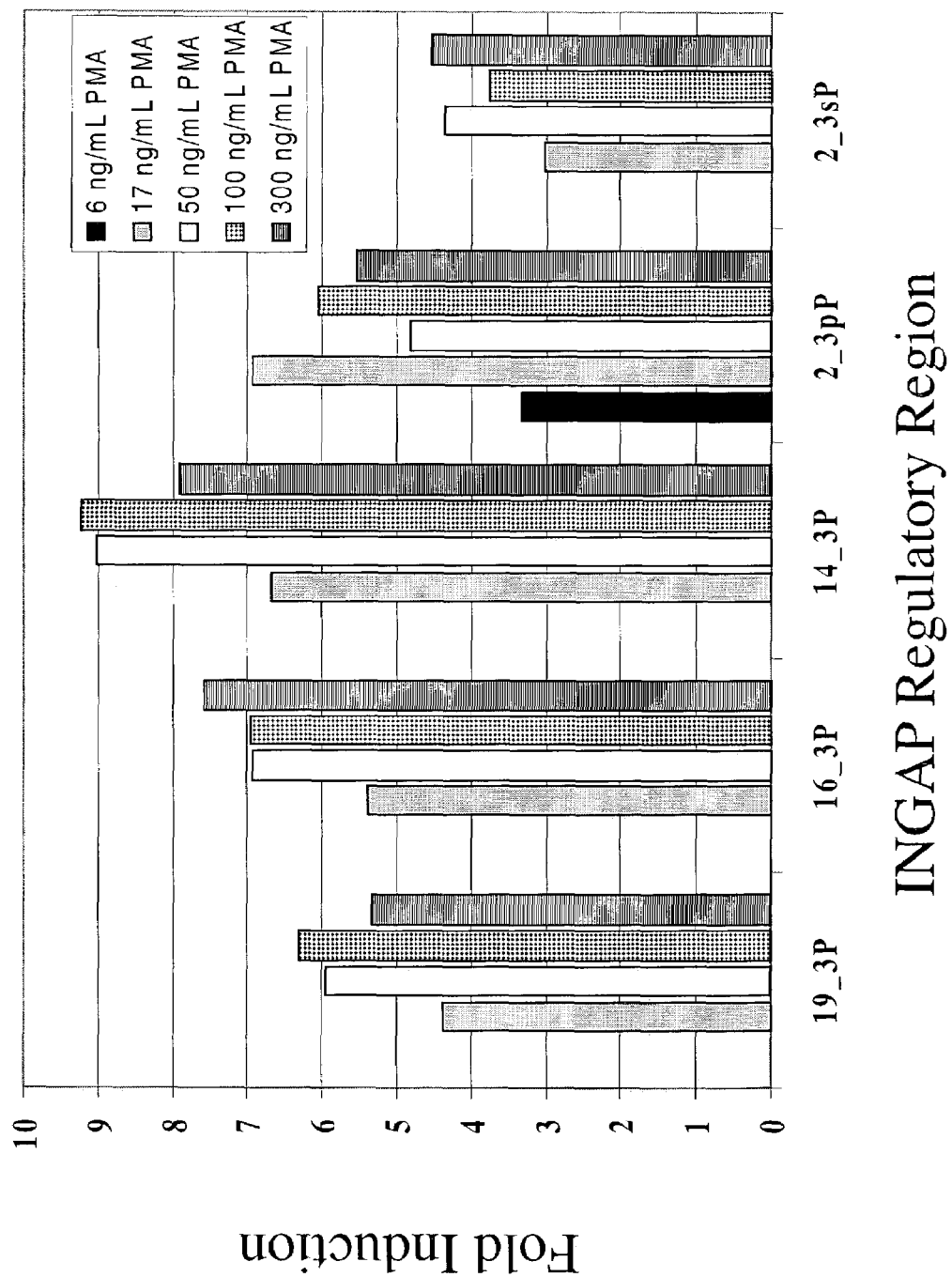
FIG. 10 shows the reporter activity in human embryonic kidney cells (293T) transfected with a reporter construct that contains different fragments (see FIG. 8) of the 5'-regulatory region of hamster INGAP cloned upstream of a β-galactosidase reporter gene. The cells are stimulated with phorbol myristate acetate. Concentrations of PMA used are 6 ng/ml, 17 ng/ml, 50 ng/ml, 100 ng/ml, or 300 ng/ml. Promoter activity is assessed by determining the level of β-galactosidase present in the cell using a β-galactosidase luminescent assay.
Figure 11:
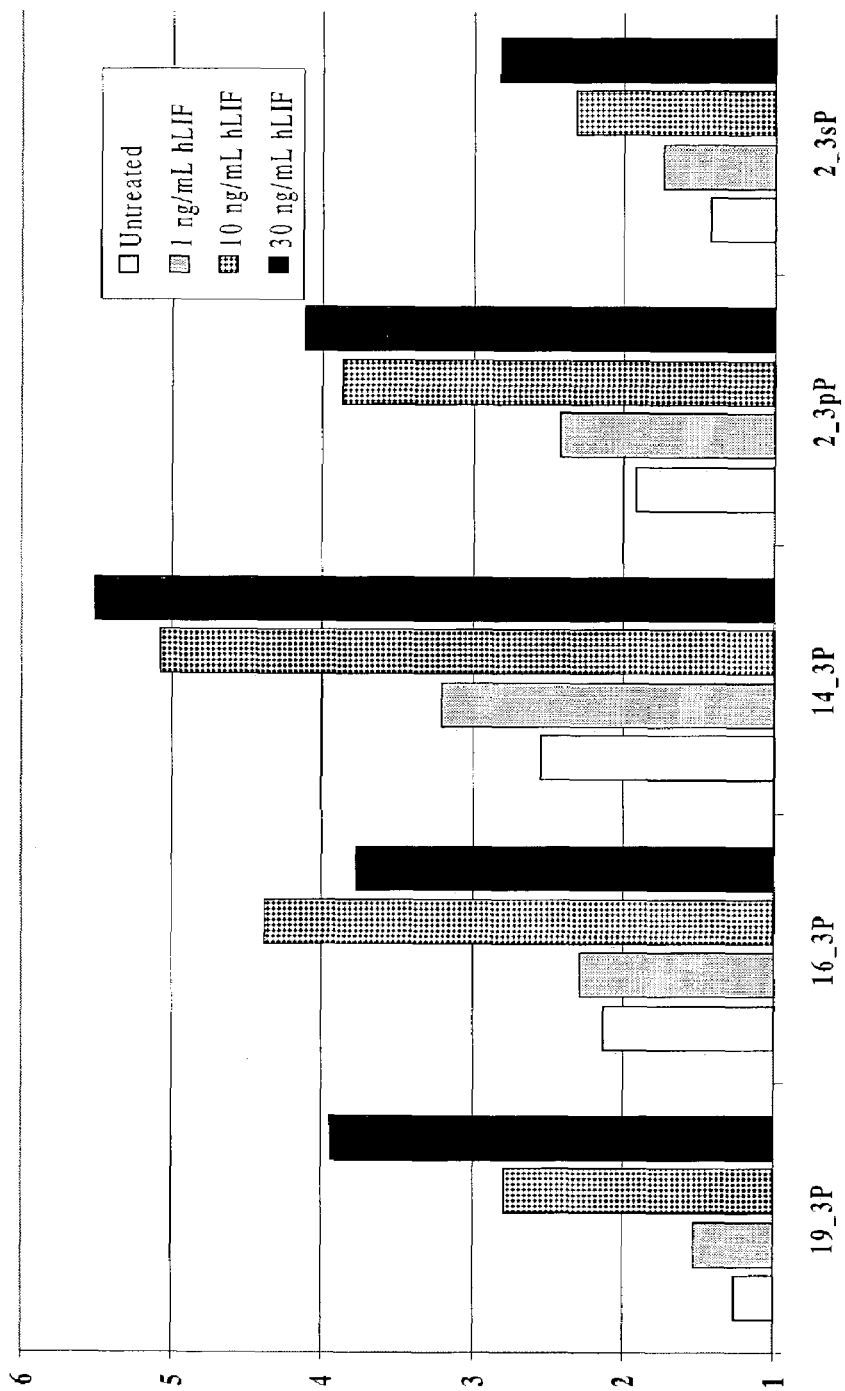
FIG. 11 shows reporter activity in human embryonic kidney cells (293T) transfected with a reporter construct that contains different fragments (see FIG. 8) of the 5'-regulatory region of hamster INGAP cloned upstream of a β-galactosidase reporter gene. The cells are stimulated with human leukemia inhibitory factor (hLIF). Concentrations of hLIF used are 1 ng/ml, 10 ng/ml, or 30 ng/ml. Promoter activity was assessed by determining the level of β-galactosidase present in the cell using a β-galactosidase luminescent assay.

Determination of Approximate Location of PMA and LIF-mediated Transcription Factor Binding in the 5'-Regulatory Region To map the approximate location of PMA-initiated or LIF-initiated transcription factor binding different fragments of the hamster INGAP 5'-regulatory region were cloned into pβGal-Basic. See FIG. 8. The fragments cloned into the reporter construct were 2_3sP (SEQ ID NO: 37), 2_3dP (SEQ ID NO: 38), 2_3pP (SEQ ID NO: 36), 14_3P (SEQ ID NO: 34), 16_3P (SEQ ID NO: 31), or 19_3P (SEQ ID NO: 23). The reporter constructs were transfected into human cells. Two days following transfection, the cells were treated with different concentrations of PMA or LIF for 24 hours. The concentrations of PMA used were 6 ng/ml, 17 ng/ml, 50 ng/ml, 100 ng/ml, or 300 ng/ml. The concentrations of LIF used were 1 ng/ml, 10 ng/ml, or 30 ng/ml. To determine the level of promoter activity, the amount of β-galactosidase gene product was determined using a luminescent assay for β-galactosidase. FIGS. 10 and 11 show the results for PMA and LIF treatment, respectively. Both PMA and LIF activated the cell reporter constructs. The exact location of the DNA contact sites can be narrowed further by cloning smaller fragments of the hamster INGAP 5'-regulatory region and by site directed mutations or deletions.

Example 5

RNA Analysis of INGAP Gene Upregulation

To determine if INGAP RNA levels increase after stimulation with a cytokine that signals through STAT, rat amphocrine pancreatic cells, AR42J were treated with IL-6 (1000 U/ml) for 24 hours. Total RNA was extracted from the treated and untreated cells using techniques well known in the art, e.g., using TRIzoL® reagent.

Equal amounts of total RNA (10 μg) were loaded in 2.5% formaldehyde gel and electrophoresed for 4 hours at 70V with a constant circulation of the buffer using a circulating pump. The gel was photographed and washed with water twice at room temperature and soaked in 20×SSC. The gel was transferred to a nylon membrane (Amersham) in 20×SSC overnight following a standard procedure. The membrane was washed with 20×SSC to remove any agar that might have attached to the membrane and baked for 4 hours at −80° C.

One hundred nanograms of hamster INGAP cDNA was labeled using Random Prime Labeling kit (Roche-BMB) and alpha-$P^{32}$ dCTP (ICN). Approximately 20 million counts were used for hybridization in 20 ml hybridization buffer following the standard procedure at 42° for overnight. The blot was washed as follows: 2-times at room temperature with 2×SSC for 10 minutes each; 2-times at 42° with 2×SSC for 10 minutes each; 2-times at 55° with 1×SSC for 10 minutes each. The membrane was exposed to the film (XOMAT-Kodak) and kept at −80° C. overnight before developing.

Figure 12:
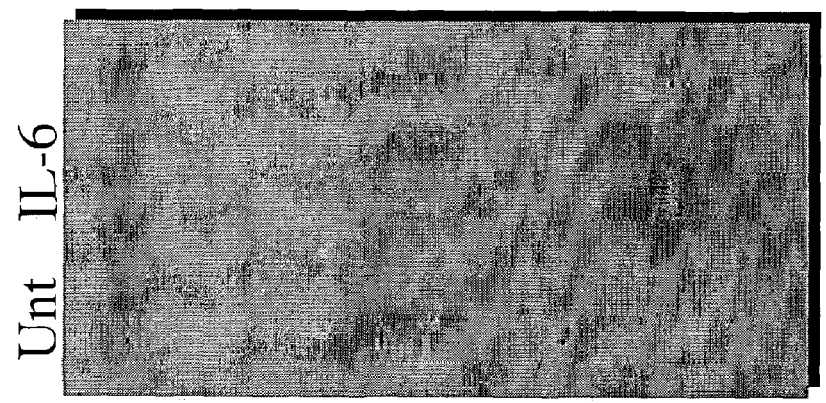
FIG. 12 shows RNA analysis for INGAP gene upregulation in rat amphicrine pancreatic cells, AR42J, treated with cytokine IL-6 or untreated. Total RNA is probed by Northern analysis for INGAP gene.

Treatment with IL-6 caused an increase in INGAP gene expression (FIG. 12). These data demonstrate that extracellular factors that elevate AP-1-binding transcription factors and STAT-binding transcription factors are involved in the regulation of INGAP gene expression. These studies suggest that it is feasible to enhance INGAP expression as a means of inducing islet neogenesis.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

TABLE 3

| Family/matrix | Further Information | Opt. | Position from-to | anchor | Str. | Core sim. | Matrix sim. | Sequence |
|---|---|---|---|---|---|---|---|---|
| V$LEFF/LEF1.01 | TCF/LEF-1, involved in the Wnt signal transduction pathway | 0.86 | 12-28 | 20 | (+) | 1.000 | 0.900 | ggaccatCAAAgtctgt |
| V$MITF/MIT.01 | MIT (microphthalmia transcription factor) and TFE3 | 0.81 | 22-40 | 31 | (+) | 1.000 | 0.823 | agtctgtCATGtcatttgg |
| V$OCT1/OCT1.05 | octamer-binding factor 1 | 0.90 | 27-41 | 34 | (+) | 0.833 | 0.904 | gTCATgtcatttggg |
| V$TCFF/TCF11.01 | TCF11/KCR-F1/Nrf1 homodimers | 1.00 | 32-38 | 35 | (+) | 1.000 | 1.000 | GTCAttt |
| V$MYOF/MYOGNF1.01 | Myogenin/nuclear factor 1 or related factors | 0.71 | 25-53 | 39 | (+) | 1.000 | 0.735 | ctgtcatgtcatTTGGgggagggcctatg |
| V$ZBPF/ZBP89.01 | Zinc finger transcription factor ZBP-89 | 0.93 | 36-48 | 42 | (−) | 1.000 | 0.982 | gccctCCCCcaaa |
| V$SP1F/GC.01 | GC box elements | 0.88 | 38-52 | 45 | (+) | 0.876 | 0.898 | tgggGGAGggcctat |
| V$PERO/PPARA.01 | PPAR/RXR heterodimers | 0.70 | 44-64 | 54 | (−) | 0.884 | 0.708 | acagaggagggcATAGgccct |
| V$PAX5/PAX9.01 | zebrafish PAX9 binding sites | 0.78 | 43-71 | 57 | (−) | 0.800 | 0.811 | cagataCACAgagagggcataggccctc |
| V$TBPF/ATATA.01 | Avian C-type LTR TATA box | 0.81 | 68-84 | 76 | (−) | 1.000 | 0.987 | tgctattTAAGcccaga |
| V$HMTB/MTBF.01 | muscle-specific Mt binding site | 0.90 | 76-84 | 80 | (−) | 1.000 | 0.932 | tgctATTTa |

TABLE 3-continued

| Family/matrix | Further Information | Opt. | Position from-to | anchor | Str. | Core sim. | Matrix sim. | Sequence |
|---|---|---|---|---|---|---|---|---|
| V$OCT1/OCT1.06 | octamer-binding factor 1 | 0.80 | 74-88 | 81 | (−) | 0.750 | 0.865 | ggtatgctATTTaag |
| V$BRNF/BRN2.01 | POU factor Brn-2 (N-Oct 3) | 0.91 | 89-105 | 97 | (+) | 1.000 | 0.970 | tccataggAAATgggct |
| V$HMTB/MTBF.01 | muscle-specific Mt binding site | 0.90 | 108-116 | 112 | (−) | 1.000 | 0.953 | tggaATTTg |
| V$OCT1/OCT1.05 | octamer-binding factor 1 | 0.90 | 106-120 | 113 | (−) | 0.944 | 0.917 | tATATggaatttggg |
| V$HNF6/HNF6.01 | Liver enriched Cut - Homeodomain transcription factor HNF6 (ONECUT) | 0.82 | 108-122 | 115 | (+) | 0.833 | 0.885 | caaatTCCAtatatg |
| V$SRFF/SRF.02 | serum response factor | 0.83 | 110-128 | 119 | (+) | 1.000 | 0.862 | aattCCAtatatgcactag |
| V$OCTP/OCT1P.01 | octamer-binding factor 1, POU-specific domain | 0.86 | 114-126 | 120 | (+) | 1.000 | 0.903 | ccatatATGCact |
| V$MYOF/MYOGNF1.01 | Myogenin/nuclear factor 1 or related factors | 0.71 | 171-199 | 185 | (+) | 0.857 | 0.740 | ctggtcttttagCTGGcacccatccatat |
| V$NF1F/NF1.02 | Nuclear factor 1 (CTF1) | 0.81 | 181-199 | 190 | (+) | 1.000 | 0.812 | agcTGGCacccatccatat |
| V$CLOX/CDPCR3HD.01 | cut-like homeodomain protein | 0.94 | 187-203 | 195 | (−) | 0.929 | 0.940 | ctgaatatgGATGggtg |
| V$MYOF/MYOGNF1.01 | Myogenin/nuclear factor 1 or related factors | 0.71 | 181-209 | 195 | (−) | 0.785 | 0.767 | aaccctctgaatATGGatgggtgccagct |
| V$OCTP/OCT1P.01 | octamer-binding factor 1, POU-specific domain | 0.86 | 192-204 | 198 | (+) | 0.980 | 0.907 | atccatATTCaga |
| V$CREB/TAXCREB.02 | Tax/CREB complex | 0.71 | 202-222 | 212 | (−) | 0.750 | 0.721 | ttgaacTGAAccaaaccctct |
| V$HOXF/EN1.01 | Homeobox protein engrailed (en-1) | 0.77 | 210-226 | 218 | (−) | 0.782 | 0.823 | aacaTTGAactgaacca |
| V$BARB/BARBIE.01 | barbiturate-inducible element | 0.88 | 230-244 | 237 | (−) | 1.000 | 0.894 | ttatAAAGctgagga |
| V$TBPF/TATA.01 | cellular and viral TATA box elements | 0.90 | 230-246 | 238 | (−) | 1.000 | 0.910 | agttaTAAAgctgagga |
| V$BARB/BARBIE.01 | barbiturate-inducible element | 0.88 | 252-266 | 259 | (−) | 1.000 | 0.902 | agtgAAAGcagagag |
| V$MYT1/MYT1.01 | MyT1 zinc finger transcription factor involved in primary neurogenesis | 0.75 | 272-284 | 278 | (−) | 0.750 | 0.756 | craCAGTtgacct |
| V$SMAD/SMAD4.01 | Smad4 transcription factor involved in TGF-beta signaling | 0.94 | 304-312 | 308 | (+) | 1.000 | 0.940 | GTCTtgact |
| V$HOXF/CRX.01 | Cone-rod homeobox-containing transcription factor/otx-like homeobox gene | 0.94 | 312-328 | 320 | (−) | 1.000 | 0.960 | gagggATTAgaaaagga |
| V$ECAT/NFY.01 | nuclear factor Y (Y-box binding factor) | 0.90 | 337-351 | 344 | (−) | 1.000 | 0.906 | ggaatCCAAtygtag |
| V$HOXF/PTX.01 | Pituitary Homeobox 1 (Ptx1) | 0.79 | 337-353 | 345 | (+) | 0.789 | 0.802 | ctacraTTGGattccat |
| V$FKHD/FREAC2.01 | Fork head RElated ACtivator-2 | 0.84 | 362-378 | 370 | (−) | 1.000 | 0.897 | tacagcTAAAcactgag |
| V$MINI/MUSCLE_INI.02 | Muscle Initiator Sequence | 0.86 | 401-419 | 410 | (−) | 0.840 | 0.865 | gagcctTCATccagtagct |
| V$MOKF/MOK2.01 | Ribonucleoprotein associated zinc finger protein MOK-2 (mouse) | 0.74 | 409-429 | 419 | (−) | 1.000 | 0.746 | tgtcatcttagagCCTTcatc |
| V$ZFIA/ZID.01 | zinc finger with interaction domain | 0.85 | 414-426 | 420 | (+) | 1.000 | 0.861 | agGCTCtaagatg |
| V$CART/XVENT2.01 | Xenopus homeodomain factor Xvent-2; early BMP signaling response | 0.82 | 418-434 | 426 | (+) | 0.750 | 0.837 | tcTAAGatgacaattaa |
| V$OCT1/OCT1.04 | octamer-binding factor 1 | 0.80 | 421-435 | 428 | (+) | 0.807 | 0.840 | aaGATGacaattaag |
| V$HOMS/S8.01 | Binding site for S8 type homeodomains | 0.97 | 426-434 | 430 | (+) | 1.000 | 0.994 | gacaATTAa |
| V$NKXH/NKX25.02 | homeo domain factor Nkx-2.5/Csx, tinman homolog low affinity sites | 0.88 | 424-436 | 430 | (−) | 1.000 | 1.000 | cctTAATtgtcat |
| V$CREB/CREBP1.01 | cAMP-responsive element binding protein 1 | 0.80 | 425-445 | 435 | (−) | 0.766 | 0.808 | cgacgattACCTtaattgtca |
| V$COMP/COMP1.01 | COMP1, cooperates with myogenic proteins in multicomponent complex | 0.76 | 434-454 | 444 | (−) | 0.750 | 0.768 | aatgaggATCGacgattacct |
| V$HOXF/HOX1-3.01 | Hox-1.3, vertebrate homeobox protein | 0.83 | 444-460 | 452 | (+) | 1.000 | 0.886 | cgatcctcATTAtagtg |
| V$ETSF/GABP.01 | GABP: GA binding protein | 0.85 | 454-470 | 462 | (+) | 1.000 | 0.868 | tatagtGGAAgggcttc |
| V$LEFF/LEF1.01 | TCF/LEF-1, involved in the Wnt signal transduction pathway | 0.86 | 463-479 | 471 | (+) | 1.000 | 0.904 | agggcttCAAAggcagt |
| V$STAT/STAT6.01 | STAT6: signal transducer and activator of transcription 6 | 0.84 | 464-482 | 473 | (−) | 0.758 | 0.867 | gagacTGCCtttgaagccc |
| V$GATA/GATA.03 | GATA-binding factor 1 | 0.95 | 490-502 | 496 | (−) | 1.000 | 0.971 | ttcaGATAggcag |
| V$SRFF/SRF.01 | serum response factor | 0.66 | 487-505 | 496 | (−) | 0.757 | 0.672 | atgttcaGATAggcagtag |
| V$EVI1/EVI1.04 | Ecotropic viral integration site 1 encoded factor | 0.77 | 493-509 | 501 | (−) | 0.800 | 0.824 | gGAAAtgttcagatagg |

TABLE 3-continued

| Family/matrix | Further Information | Opt. | Position from-to | anchor | Str. | Core sim. | Matrix sim. | Sequence |
|---|---|---|---|---|---|---|---|---|
| V$AP4R/TH1E47.01 | Thing1/E47 heterodimer, TH1 bHLH member specific expression in a variety of embryonic tissues | 0.93 | 509-525 | 517 | (+) | 1.000 | 0.951 | cctaatgCCAGatgtct |
| V$AP4R/TAL1BETAITF2.01 | Tal-1beta/ITF-2 heterodimer | 0.85 | 512-528 | 520 | (+) | 1.000 | 0.852 | aatgcCAGAtgtctctt |
| V$NEUR/NEUROD1.01 | DNA binding site for NEUROD1 (BETA-2/E47 dimer) | 0.83 | 514-526 | 520 | (−) | 1.000 | 0.851 | gagaCATCtggca |
| V$MEF2/MEF2.05 | MEF2 | 0.96 | 518-540 | 529 | (−) | 1.000 | 0.984 | aggataggttTAAAgagacatct |
| V$EVI1/EVI1.04 | Ecotropic viral integration site 1 encoded factor | 0.77 | 523-539 | 531 | (−) | 1.000 | 0.774 | gGATAggtttaaagaga |
| V$MEF2/AMEF2.01 | myocyte enhancer factor | 0.80 | 521-543 | 532 | (+) | 1.000 | 0.813 | tgtctcttTAAAcctatcctggc |
| V$TBPF/MTATA.01 | Muscle TATA box | 0.84 | 524-540 | 532 | (+) | 1.000 | 0.877 | ctcttTAAAcctatcct |
| V$HOXF/HOX1-3.01 | Hox-1.3, vertebrate homeobox protein | 0.83 | 543-559 | 551 | (+) | 1.000 | 0.845 | ctcccttcATTAaggta |
| V$PDX1/ISL1.01 | Pancreatic and intestinal lim-homeodomain factor | 0.82 | 543-563 | 553 | (−) | 1.000 | 0.834 | gagatacctTAATgaagggag |
| V$OCT1/OCT1.05 | octamer-binding factor 1 | 0.90 | 556-570 | 563 | (+) | 0.944 | 0.926 | gGTATctcattttt |
| V$CIZF/NMP4.01 | NMP4 (nuclear matrix protein 4)/CIZ (Cas-interacting zinc finger protein) | 0.97 | 562-572 | 567 | (−) | 1.000 | 0.972 | gcAAAAaatga |
| V$EVI1/EVI1.01 | Ecotropic viral integration site 1 encoded factor | 0.72 | 569-585 | 577 | (−) | 0.764 | 0.720 | ggaaCAGAggagagcaa |
| V$AP1F/AP1.01 | AP1 binding site | 0.95 | 582-602 | 592 | (−) | 0.881 | 0.964 | aaaactgaATCAgtggnggaa |
| V$PIT1/PIT1.01 | Pit1, GHF-1 pituitary specific pou domain transcription factor | 0.86 | 589-599 | 594 | (+) | 1.000 | 0.886 | actgATTCagt |
| V$AP1F/AP1.01 | AP1 binding site | 0.95 | 586-606 | 596 | (+) | 0.850 | 0.956 | nccactgaTTCAgttttctg |
| V$VMYB/VMYB.01 | v-Myb | 0.90 | 593-603 | 598 | (−) | 0.876 | 0.910 | aaaAACTgaat |
| V$CIZF/NMP4.01 | NMP4 (nuclear matrix protein 4)/CIZ (Cas-interacting zinc finger protein) | 0.97 | 595-605 | 600 | (−) | 1.000 | 0.975 | agAAAAactga |
| V$GREF/PRE.01 | Progesterone receptor binding site | 0.84 | 604-622 | 613 | (+) | 1.000 | 0.875 | ctgatccctctTGTTctcc |
| V$GKLF/GKLF.01 | Gut-enriched Krueppel-like factor | 0.91 | 632-646 | 639 | (−) | 1.000 | 0.971 | gaaaaagagaAGGGa |
| V$CIZF/NMP4.01 | NMP4 (nuclear matrix protein 4)/CIZ (Cas-interacting zinc finger protein) | 0.97 | 637-647 | 642 | (−) | 1.000 | 0.987 | ggAAAAagaga |
| V$NFAT/NFAT.01 | Nuclear factor of activated T-cells | 0.97 | 640-650 | 645 | (−) | 1.000 | 0.982 | ggagGAAAaag |
| V$MAZF/MAZ.01 | Myc associated zinc finger protein (MAZ) | 0.90 | 649-661 | 655 | (−) | 1.000 | 0.910 | ggtgGAGGgaagg |
| V$EGRF/WT1.01 | Wilms Tumor Suppressor | 0.88 | 658-672 | 665 | (−) | 1.000 | 0.932 | gggggTGGGagggtg |
| V$ZBPF/ZBP89.01 | Zinc finger transcription factor ZBP-89 | 0.93 | 663-675 | 669 | (+) | 1.000 | 0.972 | tcccaCCCCcatg |
| V$IRFF/IRF2.01 | interferon regulatory factor 2 | 0.80 | 702-716 | 709 | (−) | 1.000 | 0.815 | aggaagggGAAAggg |
| V$BRNF/BRN2.01 | POU factor Brn-2 (N-Oct 3) | 0.91 | 746-762 | 754 | (−) | 1.000 | 0.911 | aaaataggAAATaagga |
| V$ETSF/PU.1.01 | Pu.1 (Pu120) Ets-like transcription factor identified in lymphoid B-cells | 0.86 | 746-762 | 754 | (−) | 1.000 | 0.883 | aaaataGGAAataagga |
| V$EVI1/EVI1.04 | Ecotropic viral integration site 1 encoded factor | 0.77 | 750-766 | 758 | (−) | 0.760 | 0.792 | aGAGAaaataggaaata |
| V$EVI1/EVI1.05 | Ecotropic viral integration site 1 encoded factor | 0.80 | 755-771 | 763 | (−) | 0.763 | 0.817 | cccccagagaaAATAgg |
| V$ZBPF/ZBP89.01 | Zinc finger transcription factor ZBP-89 | 0.93 | 764-776 | 770 | (−) | 1.000 | 0.934 | ccacaCCCCcaga |
| V$FAST/FAST1.01 | FAST-1 SMAD interacting protein | 0.81 | 769-783 | 776 | (+) | 0.983 | 0.894 | gggtgtgGATTtat |
| V$TBPF/TATA.02 | Mammalian C-type LTR TATA box | 0.89 | 771-787 | 779 | (−) | 1.000 | 0.942 | caccaTAAAtccacac |
| V$PAX5/PAX9.01 | zebrafish PAX9 binding sites | 0.78 | 781-809 | 795 | (−) | 0.866 | 0.813 | aacataTGCAcagaagggcttccaccata |
| V$OCT1/OCT.01 | Octamer binding site (OCT1/OCT2 consensus) | 0.79 | 793-807 | 800 | (−) | 1.000 | 0.790 | catATGCacagaagg |
| V$OCTP/OCT1P.01 | octamer-binding factor 1, POU-specific domain | 0.86 | 798-810 | 804 | (−) | 1.000 | 0.910 | caacatATGCaca |
| V$SRFF/SRF.01 | serum response factor | 0.66 | 797-815 | 806 | (+) | 0.757 | 0.666 | ctgtgcaTATGttgtctta |
| V$EVI1/EVI1.05 | Ecotropic viral integration site 1 encoded factor | 0.80 | 802-818 | 810 | (−) | 0.750 | 0.828 | caataagacaaCATAtg |
| V$CLOX/CDP.01 | cut-like homeodomain protein | 0.75 | 803-819 | 811 | (−) | 1.000 | 0.776 | ccAATAagacaacatat |
| V$EVI1/EVI1.02 | Ecotropic viral integration site 1 encoded factor | 0.83 | 807-823 | 815 | (−) | 1.000 | 0.836 | tcaaccaatAAGAcaac |
| V$ECAT/NFY.02 | nuclear factor Y (Y-box binding factor) | 0.91 | 810-824 | 817 | (−) | 1.000 | 0.960 | atcaaCCAAtaagac |

TABLE 3-continued

| Family/matrix | Further Information | Opt. | Position from-to | anchor | Str. | Core sim. | Matrix sim. | Sequence |
|---|---|---|---|---|---|---|---|---|
| V$HAML/AML3.01 | Runt-related transcription factor 2/CBFA1 (core-binding factor, runt domain, alpha subunit 1) | 0.84 | 811-825 | 818 | (+) | 1.000 | 0.844 | tcttatTGGTtgata |
| V$PCAT/CAAT.01 | cellular and viral CCAAT box | 0.90 | 813-823 | 818 | (−) | 1.000 | 0.943 | tcaaCCAAtaa |
| V$GATA/GATA.01 | GATA binding site (consensus) | 0.95 | 818-830 | 824 | (+) | 1.000 | 0.956 | ggttGATAaataa |
| V$HNF1/HNF1.02 | Hepatic nuclear factor 1 | 0.76 | 818-834 | 826 | (+) | 0.757 | 0.791 | gGTTGataaataaagca |
| V$HOXT/MEIS1_HOXA9.01 | Homeobox protein MEIS1 binding site | 0.79 | 823-835 | 829 | (−) | 0.750 | 0.797 | gTGCTttatttat |
| V$ECAT/NFY.01 | nuclear factor Y (Y-box binding factor) | 0.90 | 837-851 | 844 | (+) | 1.000 | 0.912 | gttgtCCAAtaggga |
| V$FKHD/FREAC2.01 | Fork head RElated ACtivator-2 | 0.84 | 844-860 | 852 | (+) | 0.750 | 0.843 | aataggGAAAcaagata |
| V$EVI1/EVI1.06 | Ecotropic viral integration site 1 encoded factor | 0.83 | 846-862 | 854 | (+) | 1.000 | 0.960 | tagggaaacaAGATagg |
| V$GATA/GATA1.01 | GATA-binding factor 1 | 0.96 | 853-865 | 859 | (+) | 1.000 | 0.970 | acaaGATAggtgg |
| V$PCAT/ACAAT.01 | Avian C-type LTR CCAAT box | 0.86 | 856-866 | 861 | (−) | 0.750 | 0.867 | cccaCCTAtct |
| V$XBBF/RFX1.01 | X-box binding protein RFX1 | 0.89 | 909-927 | 918 | (−) | 1.000 | 0.929 | ggatcacatgGCAAcctc |
| V$EBOX/MYCMAX.02 | c-Myc/Max heterodimer | 0.92 | 912-928 | 920 | (−) | 0.895 | 0.936 | aggatCACAtggcaacc |
| V$MITF/MIT.01 | MIT (microphthalmia transcription factor) and TFE3 | 0.81 | 911-929 | 920 | (+) | 1.000 | 0.863 | ggggttgcCATGtgatccta |
| V$ETSF/PU1.01 | Pu.1 (Pu120) Ets-like transcription factor identified in lymphoid B-cells | 0.86 | 927-943 | 935 | (+) | 1.000 | 0.950 | ctaggaGGAAttgacac |
| V$OCT1/OCT1.06 | octamer-binding factor 1 | 0.80 | 932-946 | 939 | (−) | 1.000 | 0.800 | catgtgtcAATTcct |
| V$TALE/TGIF.01 | TG-interacting factor belonging to TALE class of homeodomain factors | 1.00 | 936-942 | 939 | (−) | 1.000 | 1.000 | tGTCAat |
| V$MITF/MIT.01 | MIT (microphthalmia transcription factor) and TFE3 | 0.81 | 935-953 | 944 | (−) | 1.000 | 0.835 | ccattctCATGtgtcaatt |
| V$OCT1/OCT1.04 | octamer-binding factor 1 | 0.80 | 941-955 | 948 | (+) | 0.846 | 0.800 | caCATGagaatgggg |
| V$GATA/GATA.01 | GATA binding site (consensus) | 0.95 | 962-974 | 968 | (+) | 1.000 | 0.998 | gaaaGATAagtcc |
| V$SRFF/SRF.01 | serum response factor | 0.66 | 968-986 | 977 | (−) | 1.000 | 0.672 | atattttTATAaggactta |
| V$CDXF/CDX2.01 | Cdx-2 mammalian caudal related intestinal transcr. factor | 0.84 | 970-988 | 979 | (−) | 1.000 | 0.867 | atatattTTTAtaaggact |
| V$FKHD/XFD2.01 | Xenopus fork head domain factor 2 | 0.89 | 972-988 | 980 | (+) | 1.000 | 0.894 | tccttaTAAAaatatat |
| V$MEF2/MEF2.01 | myogenic enhancer factor 2 | 0.74 | 970-992 | 981 | (+) | 1.000 | 0.740 | agtccttaTAAAaatatatatta |
| V$TBPF/TATA.01 | cellular and viral TATA box elements | 0.90 | 973-989 | 981 | (+) | 1.000 | 0.963 | ccttaTAAAaatatata |
| V$CART/CART1.01 | Cart-1 (cartilage homeoprotein 1) | 0.84 | 978-994 | 986 | (−) | 1.000 | 0.870 | acTAAtatatattttta |
| V$CART/CART1.01 | Cart-1 (cartilage homeoprotein 1) | 0.84 | 985-1001 | 993 | (−) | 1.000 | 0.855 | caTAATtactaatatat |
| V$SATB/SATB1.01 | Special AT-rich sequence-binding protein 1, predominantly expressed in thymocytes, binds to matrix attachment regions (MARs) | 0.93 | 985-1001 | 993 | (−) | 1.000 | 0.943 | cataattacTAATatat |
| V$BRNF/BRN3.01 | POU transcription factor Brn-3 | 0.78 | 987-1003 | 995 | (−) | 1.000 | 0.816 | cccATAAttactaatat |
| V$CLOX/CDP.01 | cut-like homeodomain protein | 0.75 | 987-1003 | 995 | (−) | 0.757 | 0.765 | ccCATAattactaatat |
| V$HOMS/S8.01 | Binding site for S8 type homeodomains | 0.97 | 992-1000 | 996 | (+) | 1.000 | 0.989 | agtaATTAt |
| V$NKXH/DLX1.01 | DLX-1, -2, and -5 binding sites | 0.91 | 990-1002 | 996 | (−) | 1.000 | 0.976 | ccatAATTactaa |
| V$HOXF/HOX1-3.01 | Hox-1.3, vertebrate homeobox protein | 0.83 | 989-1005 | 997 | (−) | 1.000 | 0.886 | aacccataATTActaat |
| V$PDX1/PDX1.01 | Pdx1 (IDX1/IPF1) pancreatic and intestinal homeodomain TF | 0.74 | 988-1008 | 998 | (−) | 1.000 | 0.775 | attaacccaTAATtactaata |
| V$FKHD/XFD3.01 | Xenopus fork head domain factor 3 | 0.82 | 998-1014 | 1006 | (+) | 0.826 | 0.844 | tatgggttAATAattaa |
| V$HNF1/HNF1.01 | hepatic nuclear factor 1 | 0.78 | 1000-1016 | 1008 | (−) | 0.755 | 0.857 | aCTTAattattaaccca |
| V$HNF1/HNF1.01 | hepatic nuclear factor 1 | 0.78 | 1002-1018 | 1010 | (+) | 1.000 | 0.966 | gGTTAataattaagtca |
| V$PAX4/PAX4.01 | Pax-4 paired domain protein, together with PAX-6 involved in pancreatic development | 0.97 | 1005-1015 | 1010 | (+) | 1.000 | 0.972 | taatAATTaag |
| V$HOMS/S8.01 | Binding site for S8 type homeodomains | 0.97 | 1007-1015 | 1011 | (−) | 1.000 | 0.995 | cttaATTAt |
| V$HOXF/HOX1-3.01 | Hox-1.3, vertebrate homeobox protein | 0.83 | 1003-1019 | 1011 | (−) | 1.000 | 0.873 | ctgacttaATTAttaac |
| V$NKXH/DLX1.01 | DLX-1, -2, and -5 binding sites | 0.91 | 1005-1017 | 1011 | (+) | 1.000 | 0.988 | taatAATTaagtc |

TABLE 3-continued

| Family/matrix | Further Information | Opt. | Position from-to | anchor | Str. | Core sim. | Matrix sim. | Sequence |
|---|---|---|---|---|---|---|---|---|
| V$RBIT/BRIGHT.01 | Bright, B cell regulator of IgH transcription | 0.92 | 1005-1017 | 1011 | (+) | 1.000 | 0.931 | taataATTAagtc |
| V$TBPF/ATATA.01 | Avian C-type LTR TATA box | 0.81 | 1005-1021 | 1013 | (+) | 1.000 | 0.881 | taataatTAAGtcagag |
| V$CREB/CREBP1.01 | cAMP-responsive element binding protein 1 | 0.80 | 1004-1024 | 1014 | (−) | 0.766 | 0.819 | tagctctgACTTaattattaa |
| V$RORA/RORA2.01 | RAR-related orphan receptor alpha2 | 0.82 | 1007-1023 | 1015 | (+) | 0.750 | 0.874 | ataattaAGTcagagct |
| V$PCAT/CAAT.01 | cellular and viral CCAAT box | 0.90 | 1022-1032 | 1027 | (+) | 0.856 | 0.928 | ctagCCATtaa |
| V$NKXH/NKX25.02 | homeo domain factor Nkx-2.5/Csx. tinman homolog low affinity sites | 0.88 | 1022-1034 | 1028 | (−) | 1.000 | 0.903 | tctTAATggctag |
| V$CREB/HLF.01 | hepatic leukemia factor | 0.84 | 1022-1042 | 1032 | (−) | 0.770 | 0.842 | ctagtGTTTcttaatggctag |
| V$HOXF/HOX1-3.01 | Hox-1.3, vertebrate homeobox protein | 0.83 | 1056-1072 | 1064 | (+) | 1.000 | 0.891 | gcttcataATTAatata |
| V$HOMS/S8.01 | Binding site for S8 type homeodomains | 0.97 | 1061-1069 | 1065 | (−) | 1.000 | 0.995 | attaATTAt |
| V$NKXH/DLX1.01 | DLX-1, -2, and -5 binding sites | 0.91 | 1059-1071 | 1065 | (+) | 1.000 | 0.988 | tcatAATTaatat |
| V$RBIT/BRIGHT.01 | Bright, B cell regulator of IgH transcription | 0.92 | 1059-1071 | 1065 | (+) | 1.000 | 0.952 | tcataATTAatat |
| V$BRNF/BRN2.01 | POU factor Brn-2 (N-Oct 3) | 0.91 | 1058-1074 | 1066 | (+) | 1.000 | 0.945 | ttcataatTAATatagt |
| V$OCT1/OCT1.06 | octamer-binding factor 1 | 0.80 | 1060-1074 | 1067 | (−) | 1.000 | 0.885 | actatattAATTatg |
| V$HOXF/HOX1-3.01 | Hox-1.3, vertebrate homeobox protein | 0.83 | 1061-1077 | 1069 | (−) | 1.000 | 0.854 | gatactatATTAattat |
| V$OCT1/OCT1.06 | octamer-binding factor 1 | 0.80 | 1079-1093 | 1086 | (+) | 0.750 | 0.875 | tgtatgttCATTtgg |
| V$FAST/FAST1.01 | FAST-1 SMAD interacting protein | 0.81 | 1080-1094 | 1087 | (+) | 0.850 | 0.887 | gtatgttCATTtggg |
| V$RREB/RREB1.01 | Ras-responsive element binding protein 1 | 0.79 | 1081-1095 | 1088 | (−) | 1.000 | 0.816 | cCCCAaatgaacata |
| V$E2FF/E2F.02 | E2F, involved in cell cycle regulation, interacts with Rb p107 protein | 0.84 | 1085-1099 | 1092 | (−) | 1.000 | 0.849 | tcagcccCAAAtgaa |
| V$CREB/TAXCREB.01 | Tax/CREB complex | 0.81 | 1091-1111 | 1101 | (+) | 1.000 | 0.828 | tggggcTGACacagttctggg |
| V$AP1F/VMAF.01 | v-Maf | 0.82 | 1092-1112 | 1102 | (+) | 1.000 | 0.833 | ggggcTGACacagttctggga |
| V$MYT1/MYT1.01 | MyT1 zinc finger transcription factor involved in primary neurogenesis | 0.75 | 1123-1135 | 1129 | (+) | 0.750 | 0.791 | aggAAGAytactt |
| V$CLOX/CLOX.01 | Clox | 0.81 | 1136-1152 | 1144 | (−) | 0.804 | 0.820 | cctacaATCCatgtacc |
| V$HNF4/HNF4.01 | Hepatic nuclear factor 4 | 0.82 | 1156-1172 | 1164 | (−) | 1.000 | 0.864 | atagagCAAAggactac |
| V$LEFF/LEF1.01 | TCF/LEF-1, involved in the Wnt signal transduction pathway | 0.86 | 1157-1173 | 1165 | (−) | 1.000 | 0.907 | catagagCAAAggacta |
| V$PERO/PPARA.01 | PPAR/RXR heterodimers | 0.70 | 1157-1177 | 1167 | (−) | 1.000 | 0.700 | tagacatagagcAAAGgactag |
| V$CLOX/CLOX.01 | Clox | 0.81 | 1173-1189 | 1181 | (+) | 0.804 | 0.831 | gtctaaATCCatatatg |
| V$HNF6/HNF6.01 | Liver enriched Cut-Homeodomain transcription factor HNF6 (ONECUT) | 0.82 | 1175-1189 | 1182 | (+) | 0.833 | 0.929 | ctaaaTCCAtatatg |
| V$SRFF/SRF.02 | serum response factor | 0.83 | 1177-1195 | 1186 | (+) | 1.000 | 0.851 | aaatCCAtatatgaatgag |
| V$CLOX/CDPCR3.01 | cut-like homeodomain protein | 0.75 | 1180-1196 | 1188 | (−) | 1.000 | 0.761 | actcattcatatATGGa |
| V$PIT1/PIT1.01 | Pit1, GHF-1 pituitary specific pou domain transcription factor | 0.86 | 1186-1196 | 1191 | (−) | 1.000 | 0.919 | actcATTcata |
| V$HMTB/MTBF.01 | muscle-specific Mt binding site | 0.90 | 1196-1204 | 1200 | (−) | 0.807 | 0.901 | tggtATGTa |
| V$FKHD/HFH8.01 | HNF-3/Fkh Homolog-8 | 0.92 | 1200-1216 | 1208 | (−) | 1.000 | 0.922 | gaaagayAAACatggta |
| V$E4FF/E4F.01 | GLI-Krueppel-related transcription factor, regulator of adenovirus E4 promoter | 0.82 | 1223-1235 | 1229 | (−) | 0.789 | 0.898 | gtgAGGTaacccc |
| V$CREB/HLF.01 | hepatic leukemia factor | 0.84 | 1221-1241 | 1231 | (+) | 1.000 | 0.854 | atgggGTTAcctcactcagga |
| V$VBPF/VBP.01 | PAR-type chicken vitellogenin promoter-binding protein | 0.86 | 1226-1236 | 1231 | (+) | 1.000 | 0.903 | gTTACctcact |
| V$OCT1/OCT.01 | Octamer binding site (OCT1/OCT2 consensus) | 0.79 | 1259-1273 | 1266 | (−) | 0.758 | 0.870 | cgcAGGCaaatgaat |
| V$STAT/STAT6.01 | STAT6: signal transducer and activator of transcription 6 | 0.84 | 1261-1279 | 1270 | (+) | 0.758 | 0.850 | tcattTGCCtgcgaatttt |
| V$CDXF/CDX2.01 | Cdx-2 mammalian caudal related intestinal transcr. factor | 0.84 | 1270-1288 | 1279 | (+) | 1.000 | 0.869 | tgcgaatTTTAagattcca |
| V$SORY/SOX9.01 | SOX (SRY-related HMG box) | 0.90 | 1280-1296 | 1288 | (−) | 1.000 | 0.990 | taaaaCAATggaatctt |
| V$FKHD/HFH2.01 | HNF-3/Fkh Homolog 2 | 0.93 | 1285-1301 | 1293 | (−) | 1.000 | 0.931 | aggaataaAACAatgga |
| V$CDXF/CDX2.01 | Cdx-2 mammalian caudal related intestinal transcr. factor | 0.84 | 1286-1304 | 1295 | (+) | 1.000 | 0.865 | ccattgtTTTAttcctctg |
| V$OCTB/TST1.01 | POU-factor Tst-1/Oct-6 | 0.87 | 1288-1302 | 1295 | (−) | 0.894 | 0.876 | gaggAATAaaacaat |

TABLE 3-continued

| Family/matrix | Further Information | Opt. | Position from-to | anchor | Str. | Core sim. | Matrix sim. | Sequence |
|---|---|---|---|---|---|---|---|---|
| V$PDX1/ISL1.01 | Pancreatic and intestinal lim-homeodomain factor | 0.82 | 1298-1318 | 1308 | (+) | 1.000 | 0.824 | tcctctgagTAATactccatt |
| V$SORY/SOX9.01 | SOX (SRY-related HMG box) | 0.90 | 1308-1324 | 1316 | (−) | 1.000 | 0.925 | ttacaCAATggagtatt |
| V$CREB/HLF.01 | hepatic leukemia factor | 0.84 | 1310-1330 | 1320 | (−) | 0.901 | 0.920 | ggtacATTAcacaatggagta |
| V$VBPF/VBP.01 | PAR-type chicken vitellogenin promoter-binding protein | 0.86 | 1315-1325 | 1320 | (−) | 1.000 | 0.871 | aTTACacaatg |
| V$CEBP/CEBPB.01 | CCAAT/enhancer binding protein beta | 0.94 | 1313-1331 | 1322 | (+) | 0.929 | 0.955 | tccattgtGTAAtgtacca |
| V$PDX1/ISL1.01 | Pancreatic and intestinal lim-homeodomain factor | 0.82 | 1313-1333 | 1323 | (+) | 1.000 | 0.859 | tccattgtTAATgtaccaca |
| V$HAML/AML1.01 | runt-factor AML-1 | 1.00 | 1323-1337 | 1330 | (−) | 1.000 | 1.000 | aaaatgTGGTacatt |
| V$GREF/ARE.01 | Androgene receptor binding site | 0.80 | 1323-1341 | 1332 | (+) | 0.750 | 0.819 | aatgtaccacaTTTTctcc |
| V$TEAF/TEF1.01 | TEF-1 related muscle factor | 0.84 | 1343-1355 | 1349 | (+) | 1.000 | 0.896 | taCATTcttcagt |
| V$CMYB/CMYB.01 | c-Myb, important in hematopoesis, cellular equivalent to avian myoblastosis virus oncogene v-myb | 0.99 | 1352-1360 | 1356 | (+) | 1.000 | 0.990 | caGTTGagg |
| V$AP4R/TH1E47.01 | Thing1/E47 heterodimer, TH1 bHLH member specific expression in a variety of embryonic tissues | 0.93 | 1378-1394 | 1386 | (−) | 1.000 | 0.932 | gcaatagCCAGaacctg |
| V$CP2F/CP2.01 | CP2 | 0.90 | 1384-1394 | 1389 | (−) | 1.000 | 0.945 | gcaatagCCAG |
| V$CHOP/CHOP.01 | heterodimers of CHOP and C/EBPalpha | 0.90 | 1386-1398 | 1392 | (−) | 1.000 | 0.951 | attTGCAatagcc |
| V$CEBP/CEBP.02 | C/EBP binding site | 0.85 | 1385-1403 | 1394 | (+) | 1.000 | 0.853 | tggctattGCAAataaccc |
| V$MEF2/HMEF2.01 | myocyte enhancer factor | 0.76 | 1384-1406 | 1395 | (+) | 1.000 | 0.809 | ctggctattgcAAATaaccctgc |
| V$OCT1/OCT1.03 | octamer-binding factor 1 | 0.85 | 1388-1402 | 1395 | (+) | 1.000 | 0.889 | ctattgcAAATaacc |
| V$HMTB/MTBF.01 | muscle-specific Mt binding site | 0.90 | 1394-1402 | 1398 | (−) | 1.000 | 0.900 | ggttATTTg |
| V$CLOX/CDPCR3.01 | cut-like homeodomain protein | 0.75 | 1422-1438 | 1430 | (+) | 0.975 | 0.761 | acatatgtcattATTGt |
| V$OCT1/OCT1.05 | octamer-binding factor 1 | 0.90 | 1423-1437 | 1430 | (+) | 0.944 | 0.938 | cATATgtcattattg |
| V$HOXF/HOX1-3.01 | Hox-1.3, vertebrate homeobox protein | 0.83 | 1423-1439 | 1431 | (+) | 1.000 | 0.836 | catatgtcATTAttgta |
| V$PDX1/PDX1.01 | Pdx1 (IDX1/IPF1) pancreatic and intestinal homeodomain TF | 0.74 | 1423-1443 | 1433 | (−) | 1.000 | 0.889 | ttcatacaaTAATgacatatg |
| V$SORY/SOX5.01 | Sox-5 | 0.87 | 1426-1442 | 1434 | (−) | 1.000 | 0.870 | tcataCAATaatgacat |
| V$OCT1/OCT1.05 | octamer-binding factor 1 | 0.90 | 1444-1458 | 1451 | (−) | 0.944 | 0.914 | aATATgtaaaacaga |
| V$CREB/E4BP4.01 | E4BP4, bZIP domain, transcriptional repressor | 0.80 | 1443-1463 | 1453 | (−) | 1.000 | 0.856 | tttaaaatatGTAAaacagat |
| V$VBPF/VBP.01 | PAR-type chicken vitellogenin promoter-binding protein | 0.86 | 1449-1459 | 1454 | (+) | 1.000 | 0.886 | tTTACatattt |
| V$TBPF/MTATA.01 | Muscle TATA box | 0.84 | 1455-1471 | 1463 | (+) | 1.000 | 0.841 | tattTAAAccatctct |
| V$PBXF/PBX1.01 | homeo domain factor Pbx-1 | 0.78 | 1469-1481 | 1475 | (−) | 1.000 | 0.783 | caagCAATctaga |
| V$COMP/COMP1.01 | COMP1, cooperates with myogenic proteins in multicomponent complex | 0.76 | 1467-1487 | 1477 | (+) | 1.000 | 0.765 | tctctagATTGcttgtaatat |
| V$SORY/SOX5.01 | Sox-5 | 0.87 | 1478-1494 | 1486 | (−) | 1.000 | 0.997 | tttaaCAATattacaag |
| V$FKHD/FREAC2.01 | Fork head RElated ACtivator-2 | 0.84 | 1485-1501 | 1493 | (+) | 1.000 | 0.885 | tatttgtTAAAcatagag |
| V$PDX1/ISL1.01 | Pancreatic and intestinal lim-homeodomain factor | 0.82 | 1495-1515 | 1505 | (+) | 1.000 | 0.839 | catagagagTAATaatgctat |
| V$HOXF/HOX1-3.01 | Hox-1.3, vertebrate homeobox protein | 0.83 | 1499-1515 | 1507 | (−) | 1.000 | 0.872 | atagcattATTActctc |
| V$PDX1/PDX1.01 | Pdx1 (IDX1/IPF1) pancreatic and intestinal homeodomain TF | 0.74 | 1498-1518 | 1508 | (−) | 0.826 | 0.843 | tttatagcaTTATtactctct |
| V$CART/XVENT2.01 | Xenopus homeodomain factor Xvent-2; early BMP signaling response | 0.82 | 1502-1518 | 1510 | (+) | 1.000 | 0.829 | agTAATaatgctataaa |
| V$CDXF/CDX2.01 | Cdx-2 mammalian caudal related intestinal transcr. factor | 0.84 | 1507-1525 | 1516 | (−) | 1.000 | 0.906 | tttaattTTTAtagcatta |
| V$MEF2/MEF2.05 | MEF2 | 0.96 | 1505-1527 | 1516 | (+) | 1.000 | 0.983 | aataatgctaTAAAaattaaaaa |
| V$HNF1/HNF1.01 | hepatic nuclear factor 1 | 0.78 | 1510-1526 | 1518 | (−) | 0.755 | 0.805 | tTTTAatttttatagca |
| V$OCT1/OCT1.06 | octamer-binding factor 1 | 0.80 | 1511-1525 | 1518 | (+) | 1.000 | 0.832 | gctataaaAATTaaa |
| V$TBPF/TATA.02 | Mammalian C-type LTR TATA box | 0.89 | 1510-1526 | 1518 | (+) | 1.000 | 0.991 | tgctaTAAAaattaaaa |
| V$NKXH/MSX.01 | Homeodomain proteins MSX-1 and MSX-2 | 0.97 | 1514-1526 | 1520 | (−) | 1.000 | 0.989 | tttTAATttttat |
| V$RBIT/BRIGHT.01 | Bright, B cell regulator of IgH transcription | 0.92 | 1515-1527 | 1521 | (+) | 1.000 | 0.944 | taaaaATTAaaaa |
| V$MEF2/AMEF2.01 | myocyte enhancer factor | 0.80 | 1514-1536 | 1525 | (+) | 1.000 | 0.807 | ataaaaatTAAAaataatgataa |

TABLE 3-continued

| Family/matrix | Further Information | Opt. | Position from-to | anchor | Str. | Core sim. | Matrix sim. | Sequence |
|---|---|---|---|---|---|---|---|---|
| V$EVI1/EVI1.02 | Ecotropic viral integration site 1 encoded factor | 0.83 | 1526-1542 | 1534 | (+) | 1.000 | 0.872 | aataatgatAAGAaaga |
| V$GATA/GATA1.02 | GATA-binding factor 1 | 0.99 | 1528-1540 | 1534 | (+) | 1.000 | 0.993 | taatGATAagaaa |
| V$GATA/GATA3.02 | GATA-binding factor 3 | 0.91 | 1537-1549 | 1543 | (+) | 1.000 | 0.931 | gaaAGATcctata |
| V$GATA/GATA3.02 | GATA-binding factor 3 | 0.91 | 1559-1571 | 1565 | (+) | 1.000 | 0.915 | tacAGATgaaaat |
| V$OCT1/OCT1.02 | octamer-binding factor 1 | 0.82 | 1561-1575 | 1568 | (+) | 0.763 | 0.867 | cagATGAaaatttag |
| V$CEBP/CEBPB.01 | CCAAT/enhancer binding protein beta | 0.94 | 1567-1585 | 1576 | (+) | 0.985 | 0.964 | aaaatttaGAAAtacttta |
| V$PLZF/PLZF.01 | Promyelocytic leukemia zink finger (TF with nine Krueppel-like zink fingers) | 0.86 | 1574-1588 | 1581 | (−) | 0.958 | 0.866 | agcTAAAgtatttct |
| V$PAX3/PAX3.01 | Pax-3 paired domain protein, expressed in embryogenesis, mutations correlate to Waardenburg Syndrome | 0.76 | 1587-1599 | 1593 | (−) | 1.000 | 0.763 | TCGTcagtggtag |
| V$CREB/ATF.01 | activating transcription factor | 0.90 | 1588-1608 | 1598 | (+) | 1.000 | 0.923 | taccacTGACgaaatttgtat |
| V$AP4R/TH1E47.01 | Thinq1/E47 heterodimer, TH1 bHLH member specific expression in a variety of embryonic tissues | 0.93 | 1614-1630 | 1622 | (−) | 1.000 | 0.959 | ttttaattCCAGacattc |
| V$NKXH/MSX.01 | Homeodomain proteins MSX-1 and MSX-2 | 0.97 | 1619-1631 | 1625 | (−) | 1.000 | 0.977 | cttTAATtccaga |
| V$RBIT/BRIGHT.01 | Bright, B cell regulator of IgH transcription | 0.92 | 1620-1632 | 1626 | (+) | 1.000 | 0.923 | ctggaATTAaaga |
| V$OCTB/TST1.01 | POU-factor Tst-1/Oct-6 | 0.87 | 1620-1634 | 1627 | (+) | 1.000 | 0.898 | ctggAATTaaagaaa |
| V$NKXH/DLX3.01 | Distal-less 3 homeodomain transcription factor | 0.91 | 1628-1640 | 1634 | (−) | 1.000 | 0.915 | cagTAATttcttt |
| V$GREF/PRE.01 | Progesterone receptor binding site | 0.84 | 1628-1646 | 1637 | (+) | 1.000 | 0.922 | aaagaaattacTGTTctttt |
| V$TBPF/TATA.01 | cellular and viral TATA box elements | 0.90 | 1636-1652 | 1644 | (−) | 1.000 | 0.934 | ttataTAAAgaacagta |
| V$FKHD/XFD2.01 | Xenopus fork head domain factor 2 | 0.89 | 1637-1653 | 1645 | (−) | 1.000 | 0.890 | attataTAAAgaacagt |
| V$TBPF/TATA.01 | cellular and viral TATA box elements | 0.90 | 1638-1654 | 1646 | (−) | 0.891 | 0.923 | tattaTATAagaacag |
| V$CREB/E4BP4.01 | E4BP4, bZIP domain, transcriptional repressor | 0.80 | 1638-1658 | 1648 | (−) | 0.769 | 0.856 | ctattattatATAAagaacag |
| V$PDX1/ISL1.01 | Pancreatic and intestinal lim-homeodomain factor | 0.82 | 1644-1664 | 1654 | (+) | 1.000 | 0.836 | ttttatataaTAATagactgta |
| V$COMP/COMP1.01 | COMP1, cooperates with myogenic proteins in multicomponent complex | 0.76 | 1648-1668 | 1658 | (+) | 0.791 | 0.760 | tataataATAGactgtaaaat |
| V$TBPF/TATA.02 | Mammalian C-type LTR TATA box | 0.89 | 1658-1674 | 1666 | (+) | 1.000 | 0.912 | gactgTAAAatggcaac |
| V$IRFF/ISRE.01 | interferon-stimulated response element | 0.81 | 1662-1676 | 1669 | (+) | 0.750 | 0.817 | gtaaaatgGCAActt |
| V$XBBF/RFX1.01 | X-box binding protein RFX1 | 0.89 | 1660-1678 | 1669 | (+) | 1.000 | 0.907 | ctgtaaaatgGCAActttt |
| V$MYT1/MYT1.02 | MyT1 zinc finger transcription factor involved in primary neurogenesis | 0.88 | 1667-1679 | 1673 | (−) | 1.000 | 0.882 | taaAAGTtgccat |
| V$OCT1/OCT1.06 | octamer-binding factor 1 | 0.80 | 1683-1697 | 1690 | (+) | 1.000 | 0.878 | tatttgctAATTcac |
| V$AP1F/TCF11MAFG.01 | TCF11/MafG heterodimers, binding to subclass of AP1 sites | 0.81 | 1681-1701 | 1691 | (−) | 0.777 | 0.865 | tcctgTGAAttagcaaatatt |
| V$NKXH/MSX2.01 | Muscle segment homeo box 2, homologue of Drosophila (HOX 8) | 0.95 | 1687-1699 | 1693 | (+) | 1.000 | 0.969 | tgCTAAttcacag |
| V$FAST/FAST1.01 | FAST-1 SMAD interacting protein | 0.81 | 1687-1701 | 1694 | (−) | 0.850 | 0.866 | tcctgtgAATTagca |
| V$PBXC/PBX1_MEIS1.03 | Binding site for a Pbx1/Meis1 heterodimer | 0.76 | 1686-1702 | 1694 | (+) | 0.750 | 0.788 | ttgctaatTCACaggat |
| V$CIZF/NMP4.01 | NMP4 (nuclear matrix protein 4)/CIZ (Cas-interacting zinc finger protein) | 0.97 | 1699-1709 | 1704 | (−) | 1.000 | 0.973 | agAAAAaatcc |
| V$STAT/STAT6.01 | STAT6: signal transducer and activator of transcription 6 | 0.84 | 1702-1720 | 1711 | (−) | 1.000 | 0.908 | agatgTTCCaaagaaaaaa |
| V$AP4R/TAL1BETAE47.01 | Tal-1beta/E47 heterodimer | 0.87 | 1710-1726 | 1718 | (−) | 1.000 | 0.919 | ttgttCAGAtgttccaa |
| V$SORY/HMGIY.01 | HMGI(Y) high-mobility-group protein I (Y), architectural transcription factor organizing the framework of a nuclear protein-DNA transcriptional complex | 0.92 | 1720-1736 | 1728 | (+) | 1.000 | 0.953 | tgaacaAATTccctta |

TABLE 3-continued

| Family/matrix | Further Information | Opt. | Position from-to | anchor | Str. | Core sim. | Matrix sim. | Sequence |
|---|---|---|---|---|---|---|---|---|
| V$MYT1/MYT1.01 | MyT1 zinc finger transcription factor involved in primary neurogenesis | 0.75 | 1723-1735 | 1729 | (+) | 0.750 | 0.757 | acaAATTtcccctt |
| V$SRFF/SRF.01 | serum response factor | 0.66 | 1728-1746 | 1737 | (+) | 1.000 | 0.771 | tttccctTATAtgaatcac |
| V$HOXF/HOXA9.01 | Member of the vertebrate HOX - cluster of homeobox factors | 0.87 | 1731-1747 | 1739 | (−) | 1.000 | 0.908 | agtGATTcatataaggg |
| V$HOXT/MEIS1_HOXA9.01 | Homeobox protein MEIS1 binding site | 0.79 | 1734-1746 | 1740 | (−) | 1.000 | 0.797 | gTGATtcatataa |
| V$PIT1/PIT1.01 | Pit1, GHF-1 pituitary specific pou domain transcription factor | 0.86 | 1737-1747 | 1742 | (−) | 1.000 | 0.912 | agtgATTCata |
| V$AP1F/AP1.01 | AP1 binding site | 0.95 | 1734-1754 | 1744 | (+) | 0.881 | 0.958 | ttatatgaATCActtacattt |
| V$VBPF/VBP.01 | PAR-type chicken vitellogenin promoter-binding protein | 0.86 | 1746-1756 | 1751 | (+) | 1.000 | 0.860 | cTTACattttt |
| V$FAST/FAST1.01 | FAST-1 SMAD interacting protein | 0.81 | 1757-1771 | 1764 | (+) | 0.850 | 0.829 | gcctgttCATTtaaa |
| V$HOXF/EN1.01 | Homeobox protein engrailed (en-1) | 0.77 | 1759-1775 | 1767 | (−) | 1.000 | 0.832 | gttttTTTAaatgaacag |
| V$TBPF/MTATA.01 | Muscle TATA box | 0.84 | 1763-1779 | 1771 | (+) | 1.000 | 0.853 | tcattTAAAaaactgca |
| V$ETSF/ETS2.01 | c-Ets-2 binding site | 0.86 | 1774-1790 | 1782 | (+) | 1.000 | 0.866 | actgcAGGAaagttgtg |
| V$MYT1/MYT1.02 | MyT1 zinc finger transcription factor involved in primary neurogenesis | 0.88 | 1780-1792 | 1786 | (+) | 1.000 | 0.891 | ggaAAGTtgtgat |
| V$GFI1/GFI1.01 | Growth factor independence 1 zinc finger protein acts as transcriptional repressor | 0.97 | 1782-1796 | 1789 | (−) | 1.000 | 1.000 | ataAATCacaactttt |
| V$TBPF/TATA.01 | cellular and viral TATA box elements | 0.90 | 1784-1800 | 1792 | (−) | 1.000 | 0.931 | cattaTAAAtcacaact |
| V$BRNF/BRN2.01 | POU factor Brn-2 (N-Oct 3) | 0.91 | 1786-1802 | 1794 | (−) | 1.000 | 0.933 | tgcattatAAATcacaa |
| V$HOXT/MEIS1_HOXA9.01 | Homeobox protein MEIS1 binding site | 0.79 | 1788-1800 | 1794 | (+) | 1.000 | 0.924 | gTGATttataatg |
| V$MEF2/AMEF2.01 | myocyte enhancer factor | 0.80 | 1783-1805 | 1794 | (−) | 0.866 | 0.827 | agttgcatTATAaatcacaactt |
| V$OCTB/TST1.01 | POU-factor Tst-1/Oct-6 | 0.87 | 1787-1801 | 1794 | (+) | 0.894 | 0.898 | tgtgATTTataatgc |
| V$HOXF/HOXA9.01 | Member of the vertebrate HOX - cluster of homeobox factors | 0.87 | 1787-1803 | 1795 | (+) | 1.000 | 0.971 | tgtGATTtataatgcaa |
| V$BRNF/BRN2.01 | POU factor Brn-2 (N-Oct 3) | 0.91 | 1788-1804 | 1796 | (+) | 1.000 | 0.916 | gtgatttaTAATgcaac |
| V$PARF/DBP.01 | Albumin D-box binding protein | 0.84 | 1791-1805 | 1798 | (+) | 0.884 | 0.891 | attttaTAATgcaact |
| V$OCT1/OCT1.02 | octamer-binding factor 1 | 0.82 | 1795-1809 | 1802 | (+) | 1.000 | 0.861 | ataATGCaactgcac |
| V$FKHD/FREAC2.01 | Fork head RElated ACtivator-2 | 0.84 | 1816-1832 | 1824 | (+) | 1.000 | 0.910 | cagtctTAAAcaatgct |
| V$SORY/SOX5.01 | Sox-5 | 0.87 | 1821-1837 | 1829 | (+) | 1.000 | 0.992 | ttaaaCAATgctaacca |
| V$AREB/AREB6.04 | AREB6 (Atp1a1 regulatory element binding factor 6) | 0.98 | 1837-1849 | 1843 | (+) | 1.000 | 0.981 | actgtGTTTcagc |
| V$MYT1/MYT1.02 | MyT1 zinc finger transcription factor involved in primary neurogenesis | 0.88 | 1848-1860 | 1854 | (−) | 1.000 | 0.889 | gggAAGTttatgc |
| V$RBPF/RBPJK.01 | Mammalian transcriptional repressor RBP-Jkappa/CBF1 | 0.84 | 1851-1865 | 1858 | (−) | 1.000 | 0.878 | tgtgTGGGaagttta |
| V$OCT1/OCT1.02 | octamer-binding factor 1 | 0.82 | 1875-1889 | 1882 | (+) | 0.763 | 0.826 | actATGAaaacacat |
| V$FKHD/FREAC4.01 | Fork head RElated ACtivator-4 | 0.78 | 1875-1891 | 1883 | (+) | 1.000 | 0.786 | actatgaaAACAcatgc |
| V$EBOX/MYCMAX.02 | c-Myc/Max heterodimer | 0.92 | 1880-1896 | 1888 | (+) | 0.895 | 0.920 | gaaaaCACAtgcttaaa |
| V$PAX6/PAX6.01 | Pax-6 paired domain protein | 0.75 | 1880-1898 | 1889 | (−) | 0.773 | 0.791 | cctttAAGCatgtgttttc |
| V$IRFF/IRF3.01 | Interferon regulatory factor 3 (IRF-3) | 0.86 | 1891-1905 | 1898 | (+) | 1.000 | 0.874 | cttaaaggCAAAtct |
| V$HNF1/HNF1.02 | Hepatic nuclear factor 1 | 0.76 | 1895-1911 | 1903 | (−) | 0.858 | 0.782 | aGGTAaagatttgccctt |
| V$FKHD/FREAC2.01 | Fork head RElated ACtivator-2 | 0.84 | 1898-1914 | 1906 | (−) | 1.000 | 0.853 | ctgaggTAAAgatttgc |
| V$E4FF/E4F.01 | GLI-Krueppel-related transcription factor, regulator of adenovirus E4 promoter | 0.82 | 1902-1914 | 1908 | (−) | 0.789 | 0.830 | ctgAGGTaaagat |
| V$CREB/CREBP1.01 | cAMP-responsive element binding protein 1 | 0.80 | 1900-1920 | 1910 | (+) | 0.766 | 0.820 | aaatctttACCTcagttaact |
| V$VBPF/VBP.01 | PAR-type chicken vitellogenin promoter-binding protein | 0.86 | 1905-1915 | 1910 | (+) | 1.000 | 0.862 | tTTACctcagt |
| V$MYT1/MYT1.01 | MyT1 zinc finger transcription factor involved in primary neurogenesis | 0.75 | 1912-1924 | 1918 | (−) | 0.750 | 0.775 | gaaTAGTtaactg |
| V$HNF1/HNF1.01 | hepatic nuclear factor 1 | 0.78 | 1913-1929 | 1921 | (+) | 1.000 | 0.811 | aGTTAactattccatag |
| V$PCAT/CAAT.01 | cellular and viral CCAAT box | 0.90 | 1928-1938 | 1933 | (+) | 0.856 | 0.925 | agagCCATga |
| V$HNF6/HNF6.01 | Liver enriched Cut - Homeodomain transcription factor HNF6 (ONECUT) | 0.82 | 1929-1943 | 1936 | (−) | 1.000 | 0.873 | tgaacTCAAtggctc |

TABLE 3-continued

| Family/matrix | Further Information | Opt. | Position from-to | anchor | Str. | Core sim. | Matrix sim. | Sequence |
|---|---|---|---|---|---|---|---|---|
| V$PXRF/PXRCAR.01 | Halfsite of PXR (pregnane X receptor)/RXR resp. CAR (constitutive androstane receptor)/RXR heterodimer binding site | 0.98 | 1935-1945 | 1940 | (−) | 1.000 | 0.980 | ctTGAActcaa |
| V$RARF/RTR.01 | Retinoid receptor-related testis-associated receptor (GCNF/RTR) | 0.81 | 1934-1952 | 1943 | (+) | 1.000 | 0.854 | attgagtTCAAgtgcattt |
| V$HOXF/EN1.01 | Homeobox protein engrailed (en-1) | 0.77 | 1936-1952 | 1944 | (+) | 0.782 | 0.813 | tgagTTCAagtgcattt |
| V$NKXH/NKX25.01 | homeo domain factor Nkx-2.5/Csx, tinman homolog, high affinity sites | 1.00 | 1939-1951 | 1945 | (+) | 1.000 | 1.000 | gttcAAGTgcatt |
| V$GATA/GATA3.02 | GATA-binding factor 3 | 0.91 | 1953-1965 | 1959 | (+) | 1.000 | 0.928 | agaAGATataatg |
| V$TBPF/TATA.01 | cellular and viral TATA box elements | 0.90 | 1968-1984 | 1976 | (−) | 0.891 | 0.912 | atataTATAtggccata |
| V$SRFF/SRF.01 | serum response factor | 0.66 | 1969-1987 | 1978 | (+) | 1.000 | 0.777 | atggccaTATAtatatata |
| V$CLOX/CDPCR3.01 | cut-like homeodomain protein | 0.75 | 1972-1988 | 1980 | (−) | 1.000 | 0.806 | atatatatatATGGc |
| V$PAX1/PAX1.01 | Pax1 paired domain protein, expressed in the developing vertebral column of mouse embryos | 0.61 | 2016-2034 | 2025 | (−) | 0.750 | 0.675 | CTGTgctgatatatatata |
| V$TBPF/ATATA.01 | Avian C-type LTR TATA box | 0.81 | 2019-2035 | 2027 | (+) | 0.750 | 0.827 | atatataTCAGcacagt |
| V$GFI1/GfI1B.01 | Growth factor independence 1 zinc finger protein Gfi-1B | 0.82 | 2021-2035 | 2028 | (+) | 1.000 | 0.904 | ataTATCagcacagt |
| V$NRSF/NRSF.01 | neuron-restrictive silencer factor | 0.69 | 2025-2045 | 2035 | (+) | 1.000 | 0.704 | atcAGCAcagtggaaacagtt |
| V$NFAT/NFAT.01 | Nuclear factor of activated T-cells | 0.97 | 2033-2043 | 2038 | (+) | 1.000 | 0.970 | agtgGAAAcag |
| V$AREB/AREB6.04 | AREB6 (Atp1a1 regulatory element binding factor 6) | 0.98 | 2034-2046 | 2040 | (−) | 1.000 | 0.991 | taactGTTTccac |
| V$HNF1/HNF1.01 | hepatic nuclear factor 1 | 0.78 | 2036-2052 | 2044 | (−) | 1.000 | 0.798 | tGTTAttaactgtttcc |
| V$FKHD/XFD3.01 | Xenopus fork head domain factor 3 | 0.82 | 2038-2054 | 2046 | (+) | 0.826 | 0.824 | aaacagttAATAacatt |
| V$PDX1/PDX1.01 | Pdx1 (IDX1/IPF1) pancreatic and intestinal homeodomain TF | 0.74 | 2036-2056 | 2046 | (+) | 1.000 | 0.749 | ggaaacagtTAATaacatttt |
| V$OCT1/OCT1.01 | octamer-binding factor 1 | 0.77 | 2050-2064 | 2057 | (−) | 1.000 | 0.863 | taTATGctaaaatgt |
| V$TBPF/TATA.01 | cellular and viral TATA box elements | 0.90 | 2053-2069 | 2061 | (−) | 0.891 | 0.908 | tagtaTATAtgctaaaa |
| V$ETSF/GABP.01 | GABP: GA binding protein | 0.85 | 2080-2096 | 2088 | (+) | 1.000 | 0.897 | gaggctGGAAggggggct |
| V$BEL1/BEL1.01 | Bel-1 similar region (defined in Lentivirus LTRs) | 0.78 | 2083-2105 | 2094 | (+) | 1.000 | 0.787 | gctggaagggggcTCAGcagtta |
| V$VMYB/VMYB.01 | v-Myb | 0.90 | 2097-2107 | 2102 | (−) | 0.876 | 0.901 | attAACTgctg |
| V$GREF/ARE.01 | Androgene receptor binding site | 0.80 | 2106-2124 | 2115 | (+) | 0.750 | 0.840 | atagcacatacTATTcttc |
| V$PDX1/PDX1.01 | Pdx1 (IDX1/IPF1) pancreatic and intestinal homeodomain TF | 0.74 | 2137-2157 | 2147 | (+) | 0.782 | 0.747 | gtttggtttTCATcacccatg |
| V$MYOD/MYOD.02 | myoblast determining factor | 0.98 | 2154-2168 | 2161 | (−) | 1.000 | 0.988 | gaacCACCtgacatg |
| V$GATA/GATA1.03 | GATA-binding factor 1 | 0.95 | 2169-2181 | 2175 | (−) | 1.000 | 0.958 | tacaGATAgaaat |
| V$AP4R/TAL1BETAE47.01 | Tal-1beta/E47 heterodimer | 0.87 | 2179-2195 | 2187 | (+) | 1.000 | 0.924 | gtaacCAGAtgatacga |
| V$OAZF/ROAZ.01 | Rat C2H2 Zn finger protein involved in olfactory neuronal differentiation | 0.73 | 2204-2220 | 2212 | (−) | 0.750 | 0.762 | agGTACccaaggggact |
| V$GATA/GATA1.01 | GATA-binding factor 1 | 0.96 | 2217-2229 | 2223 | (−) | 1.000 | 0.960 | aggtGATAgaggt |
| V$MYOD/E47.02 | TAL1/E47 dimers | 0.93 | 2220-2234 | 2227 | (−) | 1.000 | 0.939 | atagCAGGtgataga |
| V$LTUP/TAACC.01 | Lentiviral TATA upstream element | 0.71 | 2225-2247 | 2236 | (+) | 0.759 | 0.710 | cacctgctattctCACCcaaaga |
| V$RREB/RREB1.01 | Ras-responsive element binding protein 1 | 0.79 | 2239-2253 | 2246 | (+) | 1.000 | 0.805 | aCCCAaagacacaca |
| V$OCT1/OCT1.05 | octamer-binding factor 1 | 0.90 | 2251-2265 | 2258 | (−) | 0.944 | 0.904 | tGTATgtgagtgtgt |
| V$OCT1/OCT1.02 | octamer-binding factor 1 | 0.82 | 2282-2296 | 2289 | (+) | 1.000 | 0.854 | tgcATGCacatagtt |
| V$COUP/COUP.01 | COUP antagonizes HNF-4 by binding site competition or synergizes by direct protein-protein interaction with HNF-4 | 0.81 | 2284-2298 | 2291 | (−) | 0.977 | 0.855 | tGAACtatgtgcatg |
| V$MEF2/MEF2.01 | myogenic enhancer factor 2 | 0.74 | 2290-2312 | 2301 | (+) | 0.750 | 0.767 | catagttcAAAAaataaaatttt |
| V$CDXF/CDX2.01 | Cdx-2 mammalian caudal related intestinal transcr. factor | 0.84 | 2296-2314 | 2305 | (−) | 1.000 | 0.896 | ttaaaatTTTAtttttga |
| V$MYT1/MYT1.01 | MyT1 zinc finger transcription factor involved in primary neurogenesis | 0.75 | 2301-2313 | 2307 | (−) | 0.750 | 0.798 | taaAATTttattt |

TABLE 3-continued

| Family/matrix | Further Information | Opt. | Position from-to | anchor | Str. | Core sim. | Matrix sim. | Sequence |
|---|---|---|---|---|---|---|---|---|
| V$NFAT/NFAT.01 | Nuclear factor of activated T-cells | 0.97 | 2314-2324 | 2319 | (+) | 1.000 | 0.991 | aaagGAAAaaa |
| V$CIZF/NMP4.01 | NMP4 (nuclear matrix protein 4)/CIZ (Cas-interacting zinc finger protein) | 0.97 | 2317-2327 | 2322 | (+) | 1.000 | 0.977 | ggAAAAaaagc |
| V$GATA/GATA3.02 | GATA-binding factor 3 | 0.91 | 2326-2338 | 2332 | (−) | 1.000 | 0.946 | aaaAGATttgagc |
| V$HMTB/MTBF.01 | muscle-specific Mt binding site | 0.90 | 2351-2359 | 2355 | (−) | 1.000 | 0.901 | aggaATTTt |
| V$NOLF/OLF1.01 | olfactory neuron-specific factor | 0.82 | 2350-2372 | 2361 | (+) | 0.806 | 0.820 | taaaatTCCTatgagtgtgtgat |
| V$PDX1/PDX1.01 | Pdx1 (IDX1/IPF1) pancreatic and intestinal homeodomain TF | 0.74 | 2363-2383 | 2373 | (−) | 0.782 | 0.753 | tactgacttTGATcacacact |
| V$GATA/GATA3.02 | GATA-binding factor 3 | 0.91 | 2395-2407 | 2401 | (−) | 1.000 | 0.942 | cacAGATtatacc |
| V$NFAT/NFAT.01 | Nuclear factor of activated T-cells | 0.97 | 2406-2416 | 2411 | (+) | 1.000 | 0.971 | tgtgGAAAaca |
| V$OCTP/OCT1P.01 | octamer-binding factor 1, POU-specific domain | 0.86 | 2433-2445 | 2439 | (+) | 0.980 | 0.879 | ctcagtATTCaca |
| V$MITF/MIT.01 | MIT (microphthalmia transcription factor) and TFE3 | 0.81 | 2438-2456 | 2447 | (−) | 1.000 | 0.827 | ctactttCATGtgtgaata |
| V$PAX8/PAX8.01 | PAX 2/5/8 binding site | 0.88 | 2441-2453 | 2447 | (−) | 0.850 | 0.952 | cttTCATgtgtga |
| V$TBPF/ATATA.01 | Avian C-type LTR TATA box | 0.81 | 2451-2467 | 2459 | (+) | 1.000 | 0.838 | aagtagcTAAGaataaa |
| V$GATA/GATA3.02 | GATA-binding factor 3 | 0.91 | 2462-2474 | 2468 | (−) | 1.000 | 0.960 | aatAGATtttatt |
| V$CLOX/CLOX.01 | Clox | 0.81 | 2462-2478 | 2470 | (+) | 0.806 | 0.819 | aataaaATCTattcatc |
| V$HNF6/HNF6.01 | Liver enriched Cut-Homeodomain transcription factor HNF6 (ONECUT) | 0.82 | 2464-2478 | 2471 | (+) | 0.785 | 0.846 | taaaaTCTAttcatc |
| V$PIT1/PIT1.01 | Pit1, GHF-1 pituitary specific pou domain transcription factor | 0.86 | 2468-2478 | 2473 | (+) | 1.000 | 0.890 | atctATTCatc |
| V$AP4R/ TAL1BETAITF2.01 | Tal-1beta/ITF-2 heterodimer | 0.85 | 2469-2485 | 2477 | (−) | 1.000 | 0.881 | aaaaaCAGAtgaataga |
| V$CIZF/NMP4.01 | NMP4 (nuclear matrix protein 4)/CIZ (Cas-interacting zinc finger protein) | 0.97 | 2477-2487 | 2482 | (−) | 1.000 | 0.981 | ggAAAAacaga |
| V$NFAT/NFAT.01 | Nuclear factor of activated T-cells | 0.97 | 2480-2490 | 2485 | (−) | 1.000 | 0.976 | taagGAAAaac |
| V$STAT/STAT.01 | signal transducers and activators of transcription | 0.87 | 2479-2497 | 2488 | (−) | 1.000 | 0.872 | aggattttaaGGAAaaaca |
| V$TBPF/TATA.02 | Mammalian C-type LTR TATA box | 0.89 | 2484-2500 | 2492 | (+) | 1.000 | 0.897 | ttcctTAAAatcctggc |
| V$FKHD/XFD3.01 | Xenopus fork head domain factor 3 | 0.82 | 2501-2517 | 2509 | (−) | 1.000 | 0.880 | actgagtcAACActgta |
| V$AP1F/AP1.01 | AP1 binding site | 0.95 | 2500-2520 | 2510 | (−) | 1.000 | 0.984 | accactgaGTCAacactgtag |
| V$AP1F/AP1.01 | AP1 binding site | 0.95 | 2504-2524 | 2514 | (+) | 0.964 | 0.984 | agtgttgaCTCAgtggttgct |
| V$PCAT/CAAT.01 | cellular and viral CCAAT box | 0.90 | 2513-2523 | 2518 | (−) | 0.826 | 0.904 | gcaaCCACtga |
| V$CDXF/CDX2.01 | Cdx-2 mammalian caudal related intestinal transcr. factor | 0.84 | 2524-2542 | 2533 | (+) | 1.000 | 0.883 | ttttaaatTTTAtgctcaaa |
| V$MYT1/MYT1.02 | MyT1 zinc finger transcription factor involved in primary neurogenesis | 0.88 | 2539-2551 | 2545 | (+) | 1.000 | 0.891 | caaAAGTtgaagc |
| V$ETSF/FLI.01 | ETS family member FLI | 0.81 | 2560-2576 | 2568 | (+) | 1.000 | 0.829 | tgaaCCGGtaattctac |
| V$MYT1/MYT1.01 | MyT1 zinc finger transcription factor involved in primary neurogenesis | 0.75 | 2569-2581 | 2575 | (−) | 1.000 | 0.757 | acaAAGTagaatt |
| V$TBPF/ATATA.01 | Avian C-type LTR TATA box | 0.81 | 2576-2592 | 2584 | (−) | 0.750 | 0.816 | aagtattTAATacaaag |
| V$SATB/SATB1.01 | Special AT-rich sequence-binding protein 1, predominantly expressed in thymocytes, binds to matrix attachment regions (MARs) | 0.93 | 2578-2594 | 2586 | (−) | 1.000 | 0.939 | acaagtattTAATacaa |
| V$NKXH/NKX31.01 | prostate-specific homeodomain protein NKX3.1 | 0.84 | 2584-2596 | 2590 | (−) | 1.000 | 0.865 | taacAAGTattta |
| V$PARF/DBP.01 | Albumin D-box binding protein | 0.84 | 2589-2603 | 2596 | (+) | 1.000 | 0.882 | acttgTTATgcatcg |
| V$PAX5/PAX5.02 | B-cell-specific activating protein | 0.75 | 2591-2619 | 2605 | (−) | 1.000 | 0.758 | aacttgatttgttgAGCGatgcataacaa |
| V$ECAT/NFY.03 | nuclear factor Y (Y-box binding factor) | 0.80 | 2604-2618 | 2611 | (+) | 0.750 | 0.809 | ctcaaCAAAtcaagt |
| V$GFI1/GFI1.01 | Growth factor independence 1 zinc finger protein acts as transcriptional repressor | 0.97 | 2608-2622 | 2615 | (+) | 1.000 | 0.976 | acaAATCaagtttta |

TABLE 3-continued

| Family/matrix | Further Information | Opt. | Position from-to | anchor | Str. | Core sim. | Matrix sim. | Sequence |
|---|---|---|---|---|---|---|---|---|
| V$HNF6/HNF6.01 | Liver enriched Cut - Homeodomain transcription factor HNF6 (ONECUT) | 0.82 | 2608-2622 | 2615 | (+) | 1.000 | 0.830 | acaaaTCAAgtttta |
| V$MYT1/MYT1.01 | MyT1 zinc finger transcription factor involved in primary neurogenesis | 0.75 | 2610-2622 | 2616 | (−) | 0.750 | 0.756 | taaAACTtgattt |
| V$PAX8/PAX8.01 | PAX 2/5/8 binding site | 0.88 | 2610-2622 | 2616 | (+) | 1.000 | 0.907 | aaaTCAAgtttta |
| V$TTFF/TTF1.01 | Thyroid transcription factor-1 (TTF1) binding site | 0.92 | 2609-2623 | 2616 | (+) | 1.000 | 0.936 | caaatCAAGttttaa |
| V$MYT1/MYT1.02 | MyT1 zinc finger transcription factor involved in primary neurogenesis | 0.88 | 2612-2624 | 2618 | (+) | 1.000 | 0.887 | atcAAGttttaac |
| V$CDXF/CDX2.01 | Cdx-2 mammalian caudal related intestinal transcr. factor | 0.84 | 2612-2630 | 2621 | (+) | 1.000 | 0.883 | atcaagtTTTAacacacca |
| V$SORY/HMGIY.01 | HMGI(Y) high-mobility-group protein I (Y), architectural transcription factor organizing the framework of a nuclear protein-DNA transcriptional complex | 0.92 | 2649-2665 | 2657 | (−) | 1.000 | 0.925 | ttaaaaAATTtaagata |
| V$HOXF/EN1.01 | Homeobox protein engrailed (en-1) | 0.77 | 2657-2673 | 2665 | (+) | 1.000 | 0.780 | attTTTAaatgggcat |
| V$OCT1/OCT1.06 | octamer-binding factor 1 | 0.80 | 2662-2676 | 2669 | (−) | 0.750 | 0.818 | tttatgccCATTtaa |
| V$BCL6/BCL6.01 | POZ/zinc finger protein, transcriptional repressor, translocations observed in diffuse large cell lymphoma | 0.76 | 2683-2699 | 2691 | (+) | 1.000 | 0.796 | ctaTTCCtacagaagtc |
| V$OCTP/OCT1P.01 | octamer-binding factor 1, POU-specific domain | 0.86 | 2715-2727 | 2721 | (+) | 1.000 | 0.860 | ctgaaaATGCatt |
| V$TEAF/TEF1.01 | TEF-1 related muscle factor | 0.84 | 2722-2734 | 2728 | (+) | 1.000 | 0.898 | tgCATTcctgatt |
| V$GFI1/GFI1.01 | Growth factor independence 1 zinc finger protein acts as transcriptional repressor | 0.97 | 2723-2737 | 2730 | (−) | 1.000 | 0.981 | ataAATCaggaatgc |
| V$HOXT/ MEIS1_HOXA9.01 | Homeobox protein MEIS1 binding site | 0.79 | 2729-2741 | 2735 | (+) | 1.000 | 0.929 | cTGATttatgtaa |
| V$HOXF/HOXA9.01 | Member of the vertebrate HOX - cluster of homeobox factors | 0.87 | 2728-2744 | 2736 | (+) | 1.000 | 0.964 | cctGATTtatgtaaata |
| V$PARF/DBP.01 | Albumin D-box binding protein | 0.84 | 2729-2743 | 2736 | (+) | 1.000 | 0.861 | ctgatTTATgtaaat |
| V$VBPF/VBP.01 | PAR-type chicken vitellogenin promoter-binding protein | 0.86 | 2732-2742 | 2737 | (−) | 1.000 | 0.929 | tTTACataaat |
| V$CREB/E4BP4.01 | E4BP4, bZIP domain, transcriptional repressor | 0.80 | 2728-2748 | 2738 | (+) | 1.000 | 0.943 | cctgatttatGTAAatatatg |
| V$OCT1/OCT1.01 | octamer-binding factor 1 | 0.77 | 2733-2747 | 2740 | (+) | 1.000 | 0.895 | ttTATGtaaatatat |
| V$FKHD/XFD1.01 | Xenopus fork head domain factor 1 | 0.90 | 2733-2749 | 2741 | (+) | 1.000 | 0.940 | ttttatgTAAAtatatgt |
| V$SRFF/SRF.01 | serum response factor | 0.66 | 2736-2754 | 2745 | (+) | 1.000 | 0.691 | atgtaaaTATAtgtatata |
| V$OCTP/OCT1P.01 | octamer-binding factor 1, POU-specific domain | 0.86 | 2746-2758 | 2752 | (+) | 0.849 | 0.883 | atgtatATACata |
| V$CLOX/CDPCR3.01 | cut-like homeodomain protein | 0.75 | 2748-2764 | 2756 | (+) | 0.888 | 0.755 | gtatatacatatATAGc |
| V$TBPF/TATA.01 | cellular and viral TATA box elements | 0.90 | 2749-2765 | 2757 | (−) | 0.891 | 0.903 | ggctaTATAtgtatata |
| V$SRFF/SRF.01 | serum response factor | 0.66 | 2750-2768 | 2759 | (+) | 1.000 | 0.709 | atatacaTATAtagccttta |
| V$TBPF/ATATA.01 | Avian C-type LTR TATA box | 0.81 | 2759-2775 | 2767 | (−) | 1.000 | 0.816 | ttgttttTAAGgctata |
| V$TBPF/TATA.02 | Mammalian C-type LTR TATA box | 0.89 | 2762-2778 | 2770 | (+) | 1.000 | 0.899 | agcctTAAAaacaaaga |
| V$CABL/CABL.01 | Multifunctional c-Abl src type tyrosine kinase | 0.97 | 2769-2779 | 2774 | (+) | 1.000 | 0.973 | aaAACaaagat |
| V$LEFF/LEF1.01 | TCF/LEF-1, involved in the Wnt signal transduction pathway | 0.86 | 2766-2782 | 2774 | (+) | 1.000 | 0.863 | ttaaaaaCAAAgattgt |
| V$OCT1/OCT1.06 | octamer-binding factor 1 | 0.80 | 2775-2789 | 2782 | (+) | 1.000 | 0.811 | aagattgtAATTttt |
| V$MEF2/MMEF2.01 | myocyte enhancer factor | 0.90 | 2776-2798 | 2787 | (−) | 1.000 | 0.900 | acaattttaTAAAaattacaatct |
| V$OCT1/OCT1.06 | octamer-binding factor 1 | 0.80 | 2780-2794 | 2787 | (−) | 1.000 | 0.844 | tttataaaAATTaca |
| V$TBPF/TATA.01 | cellular and viral TATA box elements | 0.90 | 2779-2795 | 2787 | (−) | 1.000 | 0.956 | attttaTAAAaattacaa |
| V$CART/CART1.01 | Cart-1 (cartilage homeoprotein 1) | 0.84 | 2780-2796 | 2788 | (+) | 1.000 | 0.875 | tgTAATttttataaatt |
| V$FKHD/XFD2.01 | Xenopus fork head domain factor 2 | 0.89 | 2780-2796 | 2788 | (−) | 1.000 | 0.903 | aattttaTAAAaattaca |
| V$MEF2/MEF2.05 | MEF2 | 0.96 | 2778-2800 | 2789 | (−) | 1.000 | 0.973 | tcacaattttaTAAAaattacaat |
| V$BRNF/BRN3.01 | POU transcription factor Brn-3 | 0.78 | 2785-2801 | 2793 | (−) | 0.750 | 0.798 | atcACAAtttataaaaa |

TABLE 3-continued

| Family/matrix | Further Information | Opt. | Position from-to | anchor | Str. | Core sim. | Matrix sim. | Sequence |
|---|---|---|---|---|---|---|---|---|
| V$TBPF/TATA.01 | cellular and viral TATA box elements | 0.90 | 2786-2802 | 2794 | (+) | 1.000 | 0.927 | ttttaTAAAttgtgatt |
| V$GFI1/GFI1.01 | Growth factor independence 1 zinc finger protein acts as transcriptional repressor | 0.97 | 2791-2805 | 2798 | (−) | 1.000 | 0.997 | aaaAATCacaattta |
| V$HOXT/ MEIS1_HOXA9.01 | Homeobox protein MEIS1 binding site | 0.79 | 2797-2809 | 2803 | (+) | 1.000 | 0.806 | gTGATttttaaaa |
| V$MEF2/MMEF2.01 | myocyte enhancer factor | 0.90 | 2792-2814 | 2803 | (−) | 1.000 | 0.923 | tattttttTAAAaatcacaattt |
| V$MEF2/MEF2.05 | MEF2 | 0.96 | 2795-2817 | 2806 | (+) | 1.000 | 0.990 | ttgtgattttTAAAaaaataaac |
| V$MEF2/MMEF2.01 | myocyte enhancer factor | 0.90 | 2797-2819 | 2808 | (+) | 1.000 | 0.905 | gtgattttTAAAaaaataaacct |
| V$HNF1/HNF1.01 | hepatic nuclear factor 1 | 0.78 | 2802-2818 | 2810 | (−) | 0.755 | 0.796 | gGTTTattttttaaaa |
| V$MEF2/MEF2.01 | myogenic enhancer factor 2 | 0.74 | 2799-2821 | 2810 | (+) | 0.750 | 0.775 | gattttaAAAAaataaacctgc |
| V$HOXF/HOX1-3.01 | Hox-1.3, vertebrate homeobox protein | 0.83 | 2814-2830 | 2822 | (+) | 1.000 | 0.848 | aaacctgcATTAtcttc |
| V$PARF/DBP.01 | Albumin D-box binding protein | 0.84 | 2816-2830 | 2823 | (−) | 0.884 | 0.851 | gaagaTAATgcaggt |
| V$PDX1/ISL1.01 | Pancreatic and intestinal lim-homeodomain factor | 0.82 | 2814-2834 | 2824 | (−) | 1.000 | 0.853 | tgctgaagaTAATgcaggttt |
| V$GATA/GATA1.02 | GATA-binding factor 1 | 0.99 | 2819-2831 | 2825 | (−) | 1.000 | 0.993 | tgaaGATAatgca |
| V$HEAT/HSF1.01 | heat shock factor 1 | 0.93 | 2845-2855 | 2850 | (+) | 0.867 | 0.951 | TGAAtgttcct |
| V$MYT1/MYT1.02 | MyT1 zinc finger transcription factor involved in primary neurogenesis | 0.88 | 2853-2865 | 2859 | (+) | 1.000 | 0.893 | cctAAGTtttgta |
| V$BCL6/BCL6.02 | POZ/zinc finger protein, transcriptional repressor, translocations observed in diffuse large cell lymphoma | 0.77 | 2857-2873 | 2865 | (+) | 1.000 | 0.772 | agttttgTAGAacttga |
| V$TTFF/TTF1.01 | Thyroid transcription factor-1 (TTF1) binding site | 0.92 | 2863-2877 | 2870 | (−) | 1.000 | 0.927 | cgtgtCAAGttctac |
| V$EBOX/USF.02 | upstream stimulating factor | 0.94 | 2868-2884 | 2876 | (−) | 1.000 | 0.997 | tctgccaCGTGtcaagt |
| V$HOXF/PTX1.01 | Pituitary Homeobox 1 (Ptx1) | 0.79 | 2892-2908 | 2900 | (+) | 1.000 | 0.795 | aggattTTAGtctacac |
| V$MYOD/ LMO2COM.01 | complex of Lmo2 bound to Tal-1, E2A proteins, and GATA-1, half-site 1 | 0.98 | 2901-2915 | 2908 | (−) | 1.000 | 0.981 | gatgCAGGtgtagac |
| V$REBV/EBVR.01 | Epstein-Barr virus transcription factor R | 0.81 | 2904-2924 | 2914 | (−) | 1.000 | 0.832 | ctgtcctcagatgcaGGTGta |
| V$ETSF/PU1.01 | Pu.1 (Pu120) Ets-like transcription factor identified in lymphoid B-cells | 0.86 | 2932-2948 | 2940 | (+) | 1.000 | 0.873 | ctaacaGGAAaggagac |
| V$MITF/MIT.01 | MIT (microphthalmia transcription factor) and TFE3 | 0.81 | 2943-2961 | 2952 | (+) | 1.000 | 0.829 | ggagacaCATGtgtggtag |
| V$HAML/AML1.01 | runt-factor AML-1 | 1.00 | 2950-2964 | 2957 | (+) | 1.000 | 1.000 | catgtgTGGTagttc |
| V$NFKB/CREL.01 | c-Rel | 0.91 | 2954-2968 | 2961 | (+) | 1.000 | 0.919 | tgtggtagTTCCcag |
| V$IKRS/IK3.01 | Ikaros 3, potential regulator of lymphocyte differentiation | 0.84 | 2958-2970 | 2964 | (−) | 1.000 | 0.841 | aactgGGAActac |
| V$RBPF/RBPJK.01 | Mammalian transcriptional repressor RBP-Jkappa/CBF1 | 0.84 | 2957-2971 | 2964 | (−) | 1.000 | 0.842 | aaacTGGAactacc |
| V$E2FF/E2F.01 | E2F, involved in cell cycle regulation, interacts with Rb p107 protein | 0.74 | 2966-2980 | 2973 | (−) | 0.750 | 0.784 | ttcacgtCAAAactg |
| V$E4FF/E4F.01 | GLI-Krueppel-related transcription factor, regulator of adenovirus E4 promoter | 0.82 | 2968-2980 | 2974 | (−) | 1.000 | 0.830 | ttcACGTcaaaac |
| V$CREB/ATF6.02 | Activating transcription factor 6, member of b-zip family, induced by ER stress | 0.85 | 2966-2986 | 2976 | (+) | 1.000 | 0.985 | cagttttGACGtgaaaagtcc |
| V$EBOX/ARNT.01 | AhR nuclear translocator homodimers | 0.89 | 2968-2984 | 2976 | (+) | 1.000 | 0.891 | gttttgaCGTGaaaagt |
| V$E4FF/E4F.01 | GLI-Krueppel-related transcription factor, regulator of adenovirus E4 promoter | 0.82 | 2971-2983 | 2977 | (+) | 1.000 | 0.909 | ttgACGTgaaaag |
| V$EBOR/XBP1.01 | X-box-binding protein 1 | 0.86 | 2970-2984 | 2977 | (+) | 1.000 | 0.890 | ttttgACGTgaaaagt |
| V$E2FF/E2F.01 | E2F, involved in cell cycle regulation, interacts with Rb p107 protein | 0.74 | 2971-2985 | 2978 | (+) | 1.000 | 0.837 | ttgacgtGAAAagtc |
| V$STAT/STAT.01 | signal transducers and activators of transcription | 0.87 | 2989-3007 | 2998 | (+) | 1.000 | 0.937 | cattcttactGGAAcctc |
| V$BCL6/BCL6.02 | POZ/zinc finger protein, transcriptional repressor, translocations observed in diffuse large cell lymphoma | 0.77 | 2991-3007 | 2999 | (+) | 0.800 | 0.805 | ttcttacTGGAaacctc |
| V$XSEC/STAF.01 | Se-Cys tRNA gene transcription activating factor | 0.77 | 3003-3025 | 3014 | (+) | 0.782 | 0.791 | acctCCCTgaatccatgccagc |
| V$NF1F/NF1.01 | Nuclear factor 1 | 0.94 | 3007-3025 | 3016 | (−) | 1.000 | 0.964 | gctTGGCatggattcaggg |
| V$OCT1/OCT1.02 | octamer-binding factor 1 | 0.82 | 3014-3028 | 3021 | (+) | 1.000 | 0.820 | tccATGCcaagcact |

TABLE 3-continued

| Family/matrix | Further Information | Opt. | Position from-to | anchor | Str. | Core sim. | Matrix sim. | Sequence |
|---|---|---|---|---|---|---|---|---|
| V$RCAT/ CLTR_CAAT.01 | Mammalian C-type LTR CCAAT box | 0.75 | 3019-3043 | 3031 | (+) | 1.000 | 0.787 | gCCAAgcactacccatcaccttgac |
| V$SF1F/SF1.01 | SF1 steroidogenic factor 1 | 0.95 | 3033-3045 | 3039 | (−) | 1.000 | 0.954 | cagtCAAGgtgat |
| V$OCT1/OCT1.01 | octamer-binding factor 1 | 0.77 | 3038-3052 | 3045 | (−) | 1.000 | 0.800 | ctTATGccagtcaag |
| V$PARF/DBP.01 | Albumin D-box binding protein | 0.84 | 3042-3056 | 3049 | (−) | 1.000 | 0.862 | agtgcTTATgccagt |
| V$ETSF/ETS1.01 | c-Ets-1 binding site | 0.92 | 3057-3073 | 3065 | (−) | 1.000 | 0.920 | atcaaAGGAaatgagtg |
| V$LEFF/LEF1.01 | TCF/LEF-1, involved in the Wnt signal transduction pathway | 0.86 | 3062-3078 | 3070 | (−) | 1.000 | 0.969 | ggggcatCAAAggaaat |
| V$MAZF/MAZ.01 | Myc associated zinc finger protein (MAZ) | 0.90 | 3072-3084 | 3078 | (−) | 1.000 | 0.912 | gaggGAGGggcat |
| V$SP1F/GC.01 | GC box elements | 0.88 | 3071-3085 | 3078 | (−) | 0.876 | 0.920 | tgagGGAGgggcatc |
| V$TBPF/TATA.01 | cellular and viral TATA box elements | 0.90 | 3091-3107 | 3099 | (+) | 1.000 | 0.973 | tattaTAAAagcacagt |
| V$SEF1/SEF1.01 | SEF1 binding site | 0.69 | 3099-3117 | 3108 | (−) | 1.000 | 0.700 | gaaagagacgaCTGTgctt |

We claim:

1. An isolated nucleic acid sequence comprising at least about nucleotides 1-3137 of SEQ ID NO: 2 (SEQ ID NO: 23).

\* \* \* \* \*

```
                         SEQUENCE LISTING

<160> NUMBER OF SEQ ID NOS: 38

<210> SEQ ID NO 1
<211> LENGTH: 3120
<212> TYPE: DNA
<213> ORGANISM: Hamster sp.
<220> FEATURE:
<221> NAME/KEY: misc_feature
<222> LOCATION: (1)..(3120)
<223> OTHER INFORMATION: n = A, C, G, or T

<400> SEQUENCE: 1
ccttctatgg aggaccatca aagtctgtca tgtcatttgg gggagggcct atgccctcct       60
ctgtgtatct gggcttaaat agcataacctc cataggaaat gggctcccaa attccatata      120
tgcactaggg aaaaatacag gttctactgt tagagatccc atagactgcc ctggtctttt      180
agctggcacc catccatatt cagagggttt ggttcagttc aatgttggtt cctcagcttt      240
ataactaggg tctctctgct ttcactatgt caggtcaact gtygttgrgg gttctccagc      300
acagtcttga ctccttttct aatccctctt ccctctctac rattggattc catgagtatg      360
gctcagtgtt tagctgtasg tacctgcttc tgcttccatc agctactgga tgaaggctct      420
aagatgacaa ttaaggtaat cgtcgatcct cattatagtg gaagggcttc aaaggcagtc      480
tctccactac tgcctatctg aacatttccc taatgccaga tgtctcttta aacctatcct      540
ggctcccttc attaaggtat ctcattttt gctctcctct gttccnccac tgattcagtt      600
tttctgatcc ctcttgttct ccacatmatc ttcccttctc ttttccctcc ttccctccac      660
cctcccaccc ccatgctccc aatttgctca ggagttcttc tcccttttccc cttcctcaga      720 ggaccatgca tttctattac gattctcctt atttcctatt ttctctgggg gtgtggattt      780
tatggtggaa gccttctgt gcatatgttg tcttattggt tgataaataa agcactgttg       840
tccaataggg aaacaagata ggtgggacta ggagttgaag aaaagtcttg gaaatgtagt      900
aaagagtaga gggttgccat gtgatcctag gaggaattga cacatgagaa tggggtcctc      960
agaaagataa gtccttataa aaatatatat tagtaattat gggttaataa ttaagtcaga    1020
gctagccatt aagaaacact agcaaacagc aaacagcttc ataattaata tagtatcctg    1080
tatgttcatt tggggctgac acagttctgg gaccaggcag gcaggaagay tacttggtac    1140
```

```
atggattgta ggatggtagt cctttgctct atgtctaaat ccatatatga atgagtacat    1200 accatgttr tctttctgtg atggggttac ctcactcagg atggtttctt ctagttccat    1260
tcatttgcct gcgaatttta agattccatt gttttattcc tctgagtaat actccattgt    1320
gtaatgtacc acattttctc catacattct tcagttgagg gggatctagg tttcttccag    1380
gttctggcta ttgcaaataa ccctgctatg aacatagctg aacatatgtc attattgtat    1440
gaatctgttt tacatatttt aaaccatctc tagattgctt gtaatattgt taaacataga    1500
gagtaataat gctataaaaa ttaaaaataa tgataagaaa gatcctatac atgttcagta    1560
cagatgaaaa tttagaaata ctttagctac cactgacgaa atttgtatgt gcagaatgtc    1620
tggaattaaa gaaattactg ttctttatat aataatagac tgtaaaatgg caacttttaa    1680
aatatttgct aattcacagg attttttctt tggaacatct gaacaaattt cccttatatg    1740
aatcacttac attttgcct gttcatttaa aaaactgcag gaaagttgtg atttataatg    1800
caactgcaca gcagccagtc ttaaacaatg ctaaccactg tgtttcagca taaacttccc    1860
acacagtcat acagactatg aaaacacatg cttaaaggca aatctttacc tcagttaact    1920
attccataga gccattgagt tcaagtgcat ttagaagata taatgtctat ggccatatat    1980 atatatat atatatatat atatatatat atatatatat atatatcagc acagtggaaa    2040
cagttaataa cattttagca tatatactat agaaaatagg aggctggaag ggggctcagc    2100
agttaatagc acatactatt cttccagaag actaaggttt ggttttcatc acccatgtca    2160
ggtggttcat ttctatctgt aaccagatga tacgatgccc tctagtcccc ttgggtacct    2220
ctatcacctg ctattctcac ccaaagacac acacactcac atacacatgt tcatggacac    2280
atgcatgcac atagttcaaa aataaaaatt ttaaaaggaa aaaaagctca aatcttttt    2340 gaagagtctt aaaattccta tgagtgtgtg atcaaagtca gtatactatt ctgaggtata    2400
atctgtgtgg aaaacacgct agcaaagtct ctctcagtat tcacacatga aagtagctaa    2460
gaataaaatc tattcatctg ttttccta aaatcctggc tacagtgttg actcagtggt    2520
tgctttaaat tttatgctca aaagttgaag cagcttttt gaaccggtaa ttctactttg    2580
tattaaatac ttgttatgca tcgctcaaca aatcaagttt taacacacca aatcttgccc    2640
tttttgtgta tcttaaattt tttaaatggg cataaattgc agctattcct acagaagtca    2700
gttcttcagt acaactgaaa atgcattcct gatttatgta aatatatgta tatacatata    2760
tagccttaaa aacaaagatt gtaattttta taaattgtga ttttaaaaa aataaacctg    2820 cattatcttc agcaggaggc tgcctgaatg ttcctaagtt ttgtagaact tgacacgtgg    2880
cagagggcaa caggatttta gtctacacct gcatctgagg acagagcagg cctaacagga    2940
aaggagacac atgtgtggta gttcccagtt ttgacgtgaa aagtcctgca ttcttactgg    3000
aaacctccct gaatccatgc caagcactac ccatcacctt gactggcata agcactcact    3060
catttccttt gatgcccctc cctcagatcc tattataaaa gcacagtcgt ctctttcctg    3120
```

<210> SEQ ID NO 2
<211> LENGTH: 6586
<212> TYPE: DNA
<213> ORGANISM: Hamster sp.
<220> FEATURE:
<221> NAME/KEY: misc_feature
<222> LOCATION: (1)..(6586)
<223> OTHER INFORMATION: n = A, C, G, or T

<400> SEQUENCE: 2

-continued

```
ccttctatgg aggaccatca aagtctgtca tgtcatttgg gggagggcct atgccctcct      60
ctgtgtatct gggcttaaat agcataggtc cataggaaat gggctcccaa attccatata     120
tgcactaggg aaaaatacag gttctactgt tagagatccc atagactgcc ctggtctttt     180
agctggcacc catccatatt cagagggttt ggttcagttc aatgttggtt cctcagcttt     240
ataactaggg tctctctgct ttcactatgt caggtcaact gtygttgrgg gttctccagc     300
acagtcttga ctccttttct aatccctctt ccctctctac rattggattc catgagtatg     360
gctcagtgtt tagctgtasg tacctgcttc tgcttccatc agctactgga tgaaggctct     420
aagatgacaa ttaaggtaat cgtcgatcct cattatagtg gaagggcttc aaaggcagtc     480
tctccactac tgcctatctg aacatttccc taatgccaga tgtctcttta aacctatcct     540
ggctcccttc attaaggtat ctcatttttt gctctcctct gttccnccac tgattcagtt     600
tttctgatcc ctcttgttct ccacatmatc ttcccttctc ttttttcctcc ttccctccac     660 cctcccaccc ccatgctccc aatttgctca ggagttcttc tcccttttccc cttcctcaga     720 ggaccatgca tttctattac gattctcctt atttcctatt ttctctgggg gtgtggattt     780
tatggtggaa gcccttctgt gcatatgttg tcttattggt tgataaataa agcactgttg     840
tccaataggg aaacaagata ggtgggacta ggagttgaag aaaagtcttg gaaatgtagt     900
aaagagtaga ggggttgccat gtgatcctag gaggaattga cacatgagaa tggggtcctc     960
agaaagataa gtccttataa aaatatatat tagtaattat gggttaataa ttaagtcaga    1020
gctagccatt aagaaacact agcaaacagc aaacagcttc ataattaata tagtatcctg    1080
tatgttcatt tggggctgac acagttctgg gaccaggcag gcaggaagay tacttggtac    1140
atggattgta ggatggtagt cctttgctct atgtctaaat ccatatatga atgagtacat    1200
accatgtttr tctttctgtg atggggttac ctcactcagg atggtttctt ctagttccat    1260
tcatttgcct gcgaattta agattccatt gttttattcc tctgagtaat actccattgt    1320
gtaatgtacc acattttctc catacattct tcagttgagg gggatctagg tttcttccag    1380
gttctggcta ttgcaaataa ccctgctatg aacatagctg aacatatgtc attattgtat    1440
gaatctgttt tacatatttt aaaccatctc tagattgctt gtaatattgt taaacataga    1500
gagtaataat gctataaaaa ttaaaaataa tgataagaaa gatcctatac atgttcagta    1560
cagatgaaaa tttagaaata cttagctac cactgacgaa atttgtatgt gcagaatgtc    1620
tggaattaaa gaaattactg ttctttatat aataatagac tgtaaaatgg caacttttaa    1680
aatatttgct aattcacagg attttttctt tggaacatct gaacaaattt cccttatatg    1740
aatcacttac attttgcct gttcatttaa aaaactgcag gaaagttgtg atttataatg    1800
caactgcaca gcagccagtc ttaaacaatg ctaaccactg tgtttcagca taaacttccc    1860
acacagtcat acagactatg aaaacacatg cttaaaggca aatctttacc tcagttaact    1920
attccataga gccattgagt tcaagtgcat ttagaagata taatgtctat ggccatatat    1980
atatatatat atatatatat atatatatat atatatatat atatatcagc acagtggaaa    2040
cagttaataa cattttagca tatatactat agaaaatagg aggctggaag ggggctcagc    2100
agttaatagc acatactatt cttccagaag actaaggttt ggttttcatc acccatgtca    2160
ggtggttcat ttctatctgt aaccagatga tacgatgccc tctagtcccc ttgggtacct    2220
ctatcacctg ctattctcac ccaaagacac acacactcac atacacatgt tcatggacac    2280
atgcatgcac atagttcaaa aaataaaatt ttaaaaggaa aaaaagctca atctttttt    2340 gaagagtctt aaaattccta tgagtgtgtg atcaaagtca gtatactatt ctgaggtata    2400
```

-continued

```
atctgtgtgg aaaacacgct agcaaagtct ctctcagtat tcacacatga aagtagctaa    2460
gaataaaatc tattcatctg tttttcctta aaatcctggc tacagtgttg actcagtggt    2520
tgctttaaat tttatgctca aaagttgaag cagcttttt gaaccggtaa ttctactttg     2580
tattaaatac ttgttatgca tcgctcaaca aatcaagttt taacacacca aatcttgccc    2640
tttttgtgta tcttaaattt tttaaatggg cataaattgc agctattcct acagaagtca    2700
gttcttcagt acaactgaaa atgcattcct gatttatgta aatatatgta tatacatata    2760
tagccttaaa aacaaagatt gtaatttta taaattgtga tttttaaaaa aataaacctg     2820
cattatcttc agcaggaggc tgcctgaatg ttcctaagtt ttgtagaact tgacacgtgg    2880
cagagggcaa caggatttta gtctacacct gcatctgagg acagagcagg cctaacagga    2940
aaggagacac atgtgtggta gttcccagtt ttgacgtgaa aagtcctgca ttcttactgg    3000
aaacctccct gaatccatgc caagcactac ccatcacctt gactggcata agcactcact    3060
catttccttt gatgcccctc cctcagatcc tattataaaa gcacagtcgt ctctttcctg    3120
gcaaaacacc ccagatctct gcaagacagg taagctggag ttcaatgata atgagaggca    3180
gatatgggtt cacctctcac atcgaaggag aaggggaaga aagttctctg ccctcacaag    3240
gcagcactct gaaactcagt agagtttgga gctgaaagct gaacatgggc tcttcatttt    3300
gctttggaat agaaagagag gggtcaaacc caaatgagtg cttccctgaa gatatacaag    3360
catgaaagaa agtagctgtg ttctgctttc atgtcctctc tatccatact accttctccc    3420
tcacaggtac catgatgctt cccatgaccc tctgtaggat gtcttggatg ctgctttcct    3480
gcctgatgtt cctttcttgg gtggaaggta aacttgctgt gcatctagca ctgggtcccc    3540
catgagtgtt cagaggaaag gggaagagaa aggctctgga gattccatat gttaaataaa    3600
aggagcattc tcatgggaaa tcttcttcat cctgcctccc tctagatcac tggaggagga    3660
tggatatgca taattgtaat ggaaagaaag ttttcccaca ttgtcagtgg actctaattt    3720
atgttggtag gtttaaaaag gaaagtgtaa atctcaggaa tgaactctaa gcaaggagac    3780
agaggacaga ggatgaacca cataggctgt cctccagcaa agggagaaaa caaaagacta    3840
ttaaatgcaa gaagtgtaaa ataaaaactc atgcttttct atatgaagaa gtctctttaa    3900
attaagaacc tgaagttgag gacgtgatag ctcagccagt aaagtgcttt ttaaagtaag    3960
catgaggact caagttgagc aaccaggtgg catttaaatt aaacgtgaca tggtgtccat    4020
gcttttaatg caaacactgg ggaaaaggat acagaaatat cctttagtaa tcactggatg    4080
accactctag caaaatatat tacccttcaa agtcagctag aaaccctatc aaaacattac    4140
agtgtgaata gggactaagc aatgacactt gagactgacc tctggcattc atatctatat    4200
gctcatgtat aatactgtgt ncacactcct cgaacacaca cacatacaca cacacataca    4260
cacacacaca cacacactca catgcacaca actgagaact agggaaatag taagagtggg    4320
aactcagaat tacagtccca atttcaaatg aagcttcata aacttttct atgttgacct     4380 ccattatcca atctccagtc tcttatccac tgcatcactg tctatttctc cctctaaacc    4440
aggtgaagaa tctcaaaaga aactgccttc ttcacgtata acctgtcctc aaggctctgt    4500
agcctatggg tcctattgct attcactgat tttgatacca cagacctggt ctaatgcaga    4560
agtgagtagt gacacacagg attgggaaca atagaaacaa gaacttccgg gtcaagagtg    4620
gtgttggatt ccaatctctg tggtttattt gactgaggtg aacccaatcc ctcacctaca    4680
ctctaccact tcccagtggg ggtttaatat tgtttccatt ctgtccttca aacagctatc    4740
```

```
ctgccagatg catttctcag gacacctggc atttcttctc agtactggtg aaattacctt    4800
cgtgtcctcc cttgtgaaga acagtttgac ggcctaccag tacatctgga ttggactcca    4860
tgatccctca catgtgcgat cctatctttg tcttgctttt tcctcatagt gccttttatc    4920
cctgtggaag attccctgtg acaccccaga aaaagcaaat gggtcataga tctccaatgc    4980
tggatggcat tagagagagg gaaatatcag ctgtagagat aagttctgtg aaatctcag     5040 agttcagttg aagtctgtat gcctatggct gacttctaag ttttcatgtg agatattgga    5100
agatattatc atcagtctta gggagtctgc aaatacaagt gtcagtaaat gctgaacaaa    5160
gaaatctttt gtgttttcc tttatagaat agattttgt tcagtggttt ctggagaaac      5220
ctcaaaagta ccaccatttg tatttatcag gaactgataa aatccagtaa atcccaattt    5280
cattccatag tttctggggg tttgtaaata ggactgaggg attctgggat aatattacac    5340
cagaaggctn ttggcaactg ggtatgacca taccaagttt ggtaaagcta ggcatgggac    5400
caaatgtttc agtgaaggta tcatgtaatc tgtaccaccc aatcctttgc actntacagg    5460
gtacactacc caacggaagt ggatggaagt ggagcagttc caatgtgctg accttctata    5520
actgggagag gaaccctct attgctgctg accgtggtta ttgtgcagtt ttgtctcaga     5580
aatcaggtaa gacagagaag aaccacctgt gattaaccca tcttcccaca tccagtatga    5640
caacctgggc atgacacagg tttgagacat acagtgtgga cgtgtggttt gtcatcttct    5700
ctcatggttg cctatatgtc tccttgcaac agtgattatc atgcagaaga gatgtcttaa    5760
gtcaagagca gacactgagt cattctttgt ttgagttcac agattcacct gccgcattcc    5820
ctttacctcc tatctctctg taggttttca gaagtggaga gattttaatt gtgaaaatga    5880
gcttccctat atctgcaaat tcaaggtcta gggcagttct aatttcaaca gcttgaaaat    5940
attatgaagc tcacatggac aaggaagcaa gtatgaggat tcactcagga agagcaagct    6000
ctgcctacac acccacacca attcccttat atcatctctg ctgtttttct atcagtatat    6060
tctgtggtgg ctgtaaccta aaggctcaga gaacaaaaat aaaatgtcat caacactctg    6120
ggcttttgtg gtctgttttt gcagtaagac tgtatgaggc tgtgcagagt aattatagaa    6180
ggaacttctg gaaatcactg catcccagtt ccaaccattg taccaaacca tgatctaact    6240
gcgtgactat tggtatactg tgatgaaagt gtggacaggg tttatagaag atgatgttgt    6300
gaacagacaa aagcattgcc ctcccttcac actgactgtc catacatacc ttcatgttgg    6360
gacacataga gtctgatgct atttaagtag accactgtaa ataccatctt tgaggcataa    6420
ctttaatcaa aatgcaatct actttgaaca atcaaacatt tatataatat gggttaaaaa    6480
tattacttca atggacttac cataaaggta tgggtagaga gtttgtccaa aacttcttac    6540
tccctcattt ccaacaaaat atcaaatatt taaagagaaa attgat                   6586
```

<210> SEQ ID NO 3
<211> LENGTH: 19
<212> TYPE: DNA
<213> ORGANISM: Hamster sp.

<400> SEQUENCE: 3
acaagcaatc tagagatgg                                                    19

<210> SEQ ID NO 4
<211> LENGTH: 23
<212> TYPE: DNA
<213> ORGANISM: Hamster sp.

<400> SEQUENCE: 4

-continued gttcagctat gttcatagca ggg  23

<210> SEQ ID NO 5
<211> LENGTH: 22
<212> TYPE: DNA
<213> ORGANISM: Hamster sp.

<400> SEQUENCE: 5
gtctgtatga ctgtgtggga ag  22

<210> SEQ ID NO 6
<211> LENGTH: 20
<212> TYPE: DNA
<213> ORGANISM: Hamster sp.

<400> SEQUENCE: 6
gcacttgaac tcaatggctc  20

<210> SEQ ID NO 7
<211> LENGTH: 22
<212> TYPE: DNA
<213> ORGANISM: Hamster sp.

<400> SEQUENCE: 7
gaaccacctg acatgggtga tg  22

<210> SEQ ID NO 8
<211> LENGTH: 24
<212> TYPE: DNA
<213> ORGANISM: Hamster sp.

<400> SEQUENCE: 8
gggcatcgta tcatctggtt acag  24

<210> SEQ ID NO 9
<211> LENGTH: 22
<212> TYPE: DNA
<213> ORGANISM: Hamster sp.

<400> SEQUENCE: 9
ggttcaaaaa agctgcttca ac  22

<210> SEQ ID NO 10
<211> LENGTH: 24
<212> TYPE: DNA
<213> ORGANISM: Hamster sp.

<400> SEQUENCE: 10
ggaatagctg caatttatgc ccat  24

<210> SEQ ID NO 11
<211> LENGTH: 26
<212> TYPE: DNA
<213> ORGANISM: Hamster sp.

<400> SEQUENCE: 11
cttaggaaca ttcaggcagc ctcctg  26

<210> SEQ ID NO 12
<211> LENGTH: 26
<212> TYPE: DNA
<213> ORGANISM: Hamster sp.

```
<400> SEQUENCE: 12
gttgccctct gccacgtgtc aagttc                                           26

<210> SEQ ID NO 13
<211> LENGTH: 27
<212> TYPE: DNA
<213> ORGANISM: Hamster sp.

<400> SEQUENCE: 13
catccaagac atcctacaga gggtcat                                          27

<210> SEQ ID NO 14
<211> LENGTH: 27
<212> TYPE: DNA
<213> ORGANISM: Hamster sp.

<400> SEQUENCE: 14
cccaagaaag gaacatcagg caggaaa                                          27

<210> SEQ ID NO 15
<211> LENGTH: 21
<212> TYPE: DNA
<213> ORGANISM: Hamster sp.

<400> SEQUENCE: 15
ccaaatgagt gcttccctga a                                                21

<210> SEQ ID NO 16
<211> LENGTH: 26
<212> TYPE: DNA
<213> ORGANISM: Hamster sp.

<400> SEQUENCE: 16
gcagcactct gaaactcagt agagtt                                           26

<210> SEQ ID NO 17
<211> LENGTH: 20
<212> TYPE: DNA
<213> ORGANISM: Hamster sp.

<400> SEQUENCE: 17
gctgctgacc gtggttattg                                                  20

<210> SEQ ID NO 18
<211> LENGTH: 23
<212> TYPE: DNA
<213> ORGANISM: Hamster sp.

<400> SEQUENCE: 18
acactaccca acggaagtgg atg                                              23

<210> SEQ ID NO 19
<211> LENGTH: 18
<212> TYPE: DNA
<213> ORGANISM: Hamster sp.

<400> SEQUENCE: 19
tttcctgcct gatgttcc                                                    18

<210> SEQ ID NO 20
<211> LENGTH: 20
<212> TYPE: DNA
<213> ORGANISM: Hamster sp.
```

<400> SEQUENCE: 20
tcatacttgc ttccttgtcc                                                     20

<210> SEQ ID NO 21
<211> LENGTH: 19
<212> TYPE: DNA
<213> ORGANISM: Hamster sp.

<400> SEQUENCE: 21
cttcacgtat aacctgtcc                                                      19

<210> SEQ ID NO 22
<211> LENGTH: 19
<212> TYPE: DNA
<213> ORGANISM: Hamster sp.

<400> SEQUENCE: 22
attagaactg ccctagacc                                                      19

<210> SEQ ID NO 23
<211> LENGTH: 3137
<212> TYPE: DNA
<213> ORGANISM: Hamster sp.
<220> FEATURE:
<221> NAME/KEY: misc_feature
<222> LOCATION: (1)..(3134)
<223> OTHER INFORMATION: n = A, T, G, or C

<400> SEQUENCE: 23
ccttctatgg aggaccatca aagtctgtca tgtcatttgg gggagggcct atgccctcct          60
ctgtgtatct gggcttaaat agcataccte cataggaaat gggctcccaa attccatata        120
tgcactaggg aaaaatacag gttctactgt tagagatccc atagactgcc ctggtctttt        180
agctggcacc catccatatt cagagggttt ggttcagttc aatgttggtt cctcagcttt        240
ataactaggg tctctctgct ttcactatgt caggtcaact gtygttgrgg gttctccagc        300
acagtcttga ctccttttct aatccctctt ccctctctac rattggattc catgagtatg        360
gctcagtgtt tagctgtasg tacctgcttc tgcttccatc agctactgga tgaaggctct        420
aagatgacaa ttaaggtaat cgtcgatcct cattatagtg gaaggcttc aaaggcagtc         480
tctccactac tgcctatctg aacatttccc taatgccaga tgtctcttta aacctatcct        540
ggctcccttc attaaggtat ctcatttttt gctctcctct gttccnccac tgattcagtt        600
tttctgatcc ctcttgttct ccacatmatc ttcccttctc tttttcctcc ttccctccac        660
cctcccaccc ccatgctccc aatttgctca ggagttcttc tcccttccc cttcctcaga        720
ggaccatgca tttctattac gattctcctt atttcctatt ttctctgggg gtgtggattt        780
tatggtggaa gcccttctgt gcatatgttg tcttattggt tgataaataa agcactgttg        840
tccaataggg aaacaagata ggtgggacta ggagttgaag aaaagtcttg gaaatgtagt        900
aaagagtaga gggttgccat gtgatcctag gaggaattga cacatgagaa tggggtcctc        960
agaaagataa gtccttataa aaatatatat tagtaattat gggttaataa ttaagtcaga       1020
gctagccatt aagaaacact agcaaacagc aaacagcttc ataattaata tagtatcctg       1080
tatgttcatt tggggctgac acagttctgg gaccaggcag gcaggaagay tacttggtac       1140
atggattgta ggatggtagt cctttgctct atgtctaaat ccatatatga atgagtacat       1200
accatgtttr tctttctgtg atggggttac ctcactcagg atggtttctt ctagttccat       1260

-continued

```
tcatttgcct gcgaatttta agattccatt gttttattcc tctgagtaat actccattgt    1320
gtaatgtacc acattttctc catacattct tcagttgagg gggatctagg tttcttccag    1380
gttctggcta ttgcaaataa ccctgctatg aacatagctg aacatatgtc attattgtat    1440
gaatctgttt tacatatttt aaaccatctc tagattgctt gtaatattgt taaacataga    1500
gagtaataat gctataaaaa ttaaaaataa tgataagaaa gatcctatac atgttcagta    1560
cagatgaaaa tttagaaata ctttagctac cactgacgaa atttgtatgt gcagaatgtc    1620
tggaattaaa gaaattactg ttctttatat aataatagac tgtaaaatgg caactttaa     1680 aatatttgct aattcacagg attttttctt tggaacatct gaacaaattt cccttatatg    1740
aatcacttac attttgcct gttcatttaa aaaactgcag gaaagttgtg atttataatg     1800
caactgcaca gcagccagtc ttaaacaatg ctaaccactg tgtttcagca taaacttccc    1860
acacagtcat acagactatg aaaacacatg cttaaaggca aatctttacc tcagttaact    1920
attccataga gccattgagt tcaagtgcat ttagaagata taatgtctat ggccatatat    1980
atatatatat atatatatat atatatatat atatatatat atatcagc acagtggaaa      2040 cagttaataa cattttagca tatatactat agaaaatagg aggctggaag ggggctcagc    2100
agttaatagc acatactatt cttccagaag actaaggttt ggttttcatc acccatgtca    2160
ggtggttcat ttctatctgt aaccagatga tacgatgccc tctagtcccc ttgggtacct    2220
ctatcacctg ctattctcac ccaaagacac acacactcac atacacatgt tcatggacac    2280
atgcatgcac atagttcaaa aaataaaatt ttaaaaggaa aaaaagctca aatctttttt    2340
gaagagtctt aaaattccta tgagtgtgtg atcaaagtca gtatactatt ctgaggtata    2400
atctgtgtgg aaaacacgct agcaaagtct ctctcagtat tcacacatga aagtagctaa    2460
gaataaaatc tattcatctg ttttttcctta aaatcctggc tacagtgttg actcagtggt    2520
tgctttaaat tttatgctca aaagttgaag cagcttttttt gaaccggtaa ttctactttg    2580
tattaaatac ttgttatgca tcgctcaaca aatcaagttt taacacacca aatcttgccc    2640
tttttgtgta tcttaaattt tttaaatggg cataaattgc agctattcct acagaagtca    2700
gttcttcagt acaactgaaa atgcattcct gatttatgta aatatatgta tatacatata    2760
tagccttaaa aacaaagatt gtaatttta taaattgtga ttttaaaaa aataaacctg      2820 cattatcttc agcaggaggc tgcctgaatg ttcctaagtt ttgtagaact tgacacgtgg    2880
cagagggcaa caggatttta gtctacacct gcatctgagg acagagcagg cctaacagga    2940
aaggagacac atgtgtggta gttcccagtt ttgacgtgaa aagtcctgca ttcttactgg    3000
aaacctccct gaatccatgc caagcactac ccatcacctt gactggcata agcactcact    3060
catttccttt gatgccctc cctcagatcc tattataaaa gcacagtcgt ctctttcctg     3120
gcaaaacacc ccagatc                                                   3137
```

```
<210> SEQ ID NO 24
<211> LENGTH: 1354
<212> TYPE: DNA
<213> ORGANISM: Hamster sp.
<220> FEATURE:
<221> NAME/KEY: misc_feature
<222> LOCATION: (1)..(1354)
<223> OTHER INFORMATION: n = A, T, G, C

<400> SEQUENCE: 24
ccttctatgg aggaccatca aagtctgtca tgtcatttgg gggagggcct atgccctcct      60
ctgtgtatct gggcttaaat agcataccct cataggaaat gggctcccaa attccatata    120
```

| | |
|---|---|
| tgcactaggg aaaaatacag gttctactgt tagagatccc atagactgcc ctggtctttt | 180 |
| agctggcacc catccatatt cagagggttt ggttcagttc aatgttggtt cctcagcttt | 240 |
| ataactaggg tctctctgct ttcactatgt caggtcaact gtygttgrgg gttctccagc | 300 |
| acagtcttga ctccttttct aatccctctt ccctctctac rattggattc catgagtatg | 360 |
| gctcagtgtt tagctgtasg tacctgcttc tgcttccatc agctactgga tgaaggctct | 420 |
| aagatgacaa ttaaggtaat cgtcgatcct cattatagtg gaagggcttc aaaggcagtc | 480 |
| tctccactac tgcctatctg aacatttccc taatgccaga tgtctcttta aacctatcct | 540 |
| ggctcccttc attaaggtat ctcattttt gctctcctct gttccnccac tgattcagtt | 600 |
| tttctgatcc ctcttgttct ccacatmatc ttcccttctc tttttcctcc ttccctccac | 660 |
| cctcccaccc ccatgctccc aatttgctca ggagttcttc tccctttccc cttcctcaga | 720 |
| ggaccatgca tttctattac gattctcctt atttcctatt ttctctgggg gtgtggattt | 780 |
| tatggtggaa gcccttctgt gcatatgttg tcttattggt tgataaataa agcactgttg | 840 |
| tccaataggg aaacaagata ggtgggacta ggagttgaag aaaagtcttg gaaatgtagt | 900 |
| aaagagtaga gggttgccat gtgatcctag gaggaattga cacatgagaa tggggtcctc | 960 |
| agaaagataa gtccttataa aaatatatat tagtaattat gggttaataa ttaagtcaga | 1020 |
| gctagccatt aagaaacact agcaaacagc aaacagcttc ataattaata tagtatcctg | 1080 |
| tatgttcatt tggggctgac acagttctgg gaccaggcag gcaggaagay tacttggtac | 1140 |
| atggattgta ggatggtagt cctttgctct atgtctaaat ccatatatga atgagtacat | 1200 |
| accatgttr tctttctgtg atggggttac ctcactcagg atggtttctt ctagttccat | 1260 |
| tcatttgcct gcgaattta agattccatt gttttattcc tctgagtaat actccattgt | 1320 |
| gtaatgtacc acattttctc catacattct tcag | 1354 |

```
<210> SEQ ID NO 25
<211> LENGTH: 1768
<212> TYPE: DNA
<213> ORGANISM: Hamster sp.
<220> FEATURE:
<221> NAME/KEY: misc_feature
<222> LOCATION: (1)..(1768)
<223> OTHER INFORMATION: n = A, T, G, or C

<400> SEQUENCE: 25
```

| | |
|---|---|
| ccttctatgg aggaccatca aagtctgtca tgtcatttgg gggagggcct atgccctcct | 60 |
| ctgtgtatct gggcttaaat agcatacctc cataggaaat gggctcccaa attccatata | 120 |
| tgcactaggg aaaaatacag gttctactgt tagagatccc atagactgcc ctggtctttt | 180 |
| agctggcacc catccatatt cagagggttt ggttcagttc aatgttggtt cctcagcttt | 240 |
| ataactaggg tctctctgct ttcactatgt caggtcaact gtygttgrgg gttctccagc | 300 |
| acagtcttga ctccttttct aatccctctt ccctctctac rattggattc catgagtatg | 360 |
| gctcagtgtt tagctgtasg tacctgcttc tgcttccatc agctactgga tgaaggctct | 420 |
| aagatgacaa ttaaggtaat cgtcgatcct cattatagtg gaagggcttc aaaggcagtc | 480 |
| tctccactac tgcctatctg aacatttccc taatgccaga tgtctcttta aacctatcct | 540 |
| ggctcccttc attaaggtat ctcattttt gctctcctct gttccnccac tgattcagtt | 600 |
| tttctgatcc ctcttgttct ccacatmatc ttcccttctc tttttcctcc ttccctccac | 660 |
| cctcccaccc ccatgctccc aatttgctca ggagttcttc tccctttccc cttcctcaga | 720 |

```
ggaccatgca tttctattac gattctcctt atttcctatt ttctctgggg gtgtggattt      780
tatggtggaa gcccttctgt gcatatgttg tcttattggt tgataaataa agcactgttg      840
tccaataggg aaacaagata ggtgggacta ggagttgaag aaaagtcttg gaaatgtagt      900
aaagagtaga gggttgccat gtgatcctag gaggaattga cacatgagaa tggggtcctc      960
agaaagataa gtccttataa aaatatatat tagtaattat gggttaataa ttaagtcaga     1020
gctagccatt aagaaacact agcaaacagc aaacagcttc ataattaata tagtatcctg     1080
tatgttcatt tggggctgac acagttctgg gaccaggcag gcaggaagay tacttggtac     1140
atggattgta ggatggtagt cctttgctct atgtctaaat ccatatatga atgagtacat     1200
accatgtttr tctttctgtg atggggttac ctcactcagg atggtttctt ctagttccat     1260
tcatttgcct gcgaatttta agattccatt gtttttattcc tctgagtaat actccattgt     1320
gtaatgtacc acattttctc catacattct tcagttgagg gggatctagg tttcttccag     1380
gttctggcta ttgcaaataa ccctgctatg aacatagctg aacatatgtc attattgtat     1440
gaatctgttt tacatatttt aaaccatctc tagattgctt gtaatattgt taaacataga     1500
gagtaataat gctataaaaa ttaaaaataa tgataagaaa gatcctatac atgttcagta     1560
cagatgaaaa tttagaaata ctttagctac cactgacgaa atttgtatgt gcagaatgtc     1620
tggaattaaa gaaattactg ttctttatat aataatagac tgtaaaatgg caacttttaa     1680
aatatttgct aattcacagg attttttctt tggaacatct gaacaaattt cccttatatg     1740
aatcacttac atttttgcct gttcattt                                         1768

<210> SEQ ID NO 26
<211> LENGTH: 2167
<212> TYPE: DNA
<213> ORGANISM: Hamster sp.
<220> FEATURE:
<221> NAME/KEY: misc_feature
<222> LOCATION: (1)..(2167)
<223> OTHER INFORMATION: n = A, T, G, or C

<400> SEQUENCE: 26
ccttctatgg aggaccatca aagtctgtca tgtcatttgg gggagggcct atgccctcct       60
ctgtgtatct gggcttaaat agcataccte cataggaaat gggctcccaa attccatata      120
tgcactaggg aaaaatacag gttctactgt tagagatccc atagactgcc ctggtctttt      180
agctggcacc catccatatt cagagggttt ggttcagttc aatgttggtt cctcagcttt      240
ataactaggg tctctctgct ttcactatgt caggtcaact gtygttgrgg gttctccagc      300
acagtcttga ctccttttct aatccctctt ccctctctac rattggattc catgagtatg      360
gctcagtgtt tagctgtasg tacctgcttc tgcttccatc agctactgga tgaaggctct      420
aagatgacaa ttaaggtaat cgtcgatcct cattatagtg aagggcttc aaaggcagtc      480 tctccactac tgcctatctg aacatttccc taatgccaga tgtctcttta aacctatcct      540
ggctcccttc attaaggtat ctcattttttt gctctcctct gttccnccac tgattcagtt      600
tttctgatcc ctcttgttct ccacatmatc ttcccttctc ttttttcctcc ttccctccac      660 cctcccaccc ccatgctccc aatttgctca ggagttcttc tccctttccc cttcctcaga      720
ggaccatgca tttctattac gattctcctt atttcctatt ttctctgggg gtgtggattt      780
tatggtggaa gcccttctgt gcatatgttg tcttattggt tgataaataa agcactgttg      840
tccaataggg aaacaagata ggtgggacta ggagttgaag aaaagtcttg gaaatgtagt      900
aaagagtaga gggttgccat gtgatcctag gaggaattga cacatgagaa tggggtcctc      960
```

```
agaaagataa gtccttataa aaatatatat tagtaattat gggttaataa ttaagtcaga    1020
gctagccatt aagaaacact agcaaacagc aaacagcttc ataattaata tagtatcctg    1080
tatgttcatt tggggctgac acagttctgg gaccaggcag gcaggaagay tacttggtac    1140
atggattgta ggatggtagt cctttgctct atgtctaaat ccatatatga atgagtacat    1200
accatgtttr tctttctgtg atggggttac ctcactcagg atggtttctt ctagttccat    1260
tcatttgcct gcgaatttta agattccatt gttttattcc tctgagtaat actccattgt    1320
gtaatgtacc acattttctc catacattct tcagttgagg gggatctagg tttcttccag    1380
gttctggcta ttgcaaataa ccctgctatg aacatagctg aacatatgtc attattgtat    1440
gaatctgttt tacatatttt aaaccatctc tagattgctt gtaatattgt taaacataga    1500
gagtaataat gctataaaaa ttaaaaataa tgataagaaa gatcctatac atgttcagta    1560
cagatgaaaa tttagaaata ctttagctac cactgacgaa atttgtatgt gcagaatgtc    1620
tggaattaaa gaaattactg ttctttatat aataatagac tgtaaaatgg caacttttaa    1680
aatatttgct aattcacagg attttttctt tggaacatct gaacaaattt cccttatatg    1740
aatcacttac attttgcct gttcatttaa aaaactgcag gaaagttgtg atttataatg    1800
caactgcaca gcagccagtc ttaaacaatg ctaaccactg tgtttcagca taaacttccc    1860
acacagtcat acagactatg aaaacacatg cttaaaggca aatctttacc tcagttaact    1920
attccataga gccattgagt tcaagtgcat ttagaagata taatgtctat ggccatatat    1980
atatatatat atatatatat atatatatat atatatatat atatatcagc acagtggaaa    2040
cagttaataa cattttagca tatatactat agaaaatagg aggctggaag ggggctcagc    2100
agttaatagc atatactatt cttccagaag actaaggttt ggttttcatc acccatgtca    2160
ggtggtt                                                             2167

<210> SEQ ID NO 27
<211> LENGTH: 2930
<212> TYPE: DNA
<213> ORGANISM: Hamster sp.
<220> FEATURE:
<221> NAME/KEY: misc_feature
<222> LOCATION: (1)..(2930)
<223> OTHER INFORMATION: n = A, T, G, or C

<400> SEQUENCE: 27
ccttctatgg aggaccatca aagtctgtca tgtcatttgg gggagggcct atgccctcct      60
ctgtgtatct gggcttaaat agcataccctc cataggaaat gggctcccaa attccatata    120
tgcactaggg aaaaatacag gttctactgt tagagatccc atagactgcc ctggtctttt    180
agctggcacc catccatatt cagagggttt ggttcagttc aatgttggtt cctcagcttt    240
ataactaggg tctctctgct ttcactatgt caggtcaact gtygttgrgg gttctccagc    300
acagtcttga ctccttttct aatccctctt ccctctctac rattggattc catgagtatg    360
gctcagtgtt tagctgtasg tacctgcttc tgcttccatc agctactgga tgaaggctct    420
aagatgacaa ttaaggtaat cgtcgatcct cattatagtg gaagggcttc aaaggcagtc    480
tctccactac tgcctatctg aacatttccc taatgccaga tgtctcttta aacctatcct    540
ggctcccttc attaaggtat ctcatttttt gctctcctct gttccnccac tgattcagtt    600
tttctgatcc ctcttgttct ccacatmatc ttccctctc tttttcctcc ttccctccac    660
cctcccaccc ccatgctccc aatttgctca ggagttcttc tccctttccc cttcctcaga    720
```

```
ggaccatgca tttctattac gattctcctt atttcctatt ttctctgggg gtgtggattt      780
tatggtggaa gcccttctgt gcatatgttg tcttattggt tgataaataa agcactgttg      840
tccaataggg aaacaagata ggtgggacta ggagttgaag aaaagtcttg gaaatgtagt      900
aaagagtaga gggttgccat gtgatcctag gaggaattga cacatgagaa tggggtcctc      960
agaaagataa gtccttataa aaatatatat tagtaattat gggttaataa ttaagtcaga     1020
gctagccatt aagaaacact agcaaacagc aaacagcttc ataattaata tagtatcctg     1080
tatgttcatt tggggctgac acagttctgg gaccaggcag gcaggaagay tacttggtac     1140
atggattgta ggatggtagt cctttgctct atgtctaaat ccatatatga atgagtacat     1200
accatgtttr tctttctgtg atggggttac ctcactcagg atggtttctt ctagttccat     1260
tcatttgcct gcgaatttta agattccatt gttttattcc tctgagtaat actccattgt     1320
gtaatgtacc acattttctc catacattct tcagttgagg gggatctagg tttcttccag     1380
gttctggcta ttgcaaataa ccctgctatg aacatagctg aacatatgtc attattgtat     1440
gaatctgttt tacatatttt aaaccatctc tagattgctt gtaatattgt taaacataga     1500
gagtaataat gctataaaaa ttaaaaataa tgataagaaa gatcctatac atgttcagta     1560
cagatgaaaa tttagaaata ctttagctac cactgacgaa atttgtatgt gcagaatgtc     1620
tggaattaaa gaaattactg ttctttatat aataatagac tgtaaaatgg caacttttaa     1680
aatatttgct aattcacagg attttttctt tggaacatct gaacaaattt cccttatatg     1740
aatcacttac attttgcct gttcatttaa aaaactgcag gaaagttgtg atttataatg     1800
caactgcaca gcagccagtc ttaaacaatg ctaaccactg tgtttcagca taaacttccc     1860
acacagtcat acagactatg aaaacacatg cttaaaggca atctttacc tcagttaact     1920
attccataga gccattgagt tcaagtgcat ttagaagata taatgtctat ggccatatat     1980
atatatatat atatatatat atatatatat atatatatat atatatcagc acagtggaaa     2040
cagttaataa cattttagca tatatactat agaaaatagg aggctggaag ggggctcagc     2100
agttaatagc acatactatt cttccagaag actaaggttt ggttttcatc acccatgtca     2160
ggtggttcat ttctatctgt aaccagatga tacgatgccc tctagtcccc ttgggtacct     2220
ctatcacctg ctattctcac ccaaagacac acacactcac atacacatgt tcatggacac     2280
atgcatgcac atagttcaaa aaataaaatt ttaaaaggaa aaaaagctca atctttttt      2340
gaagagtctt aaaattccta tgagtgtgtg atcaaagtca gtatactatt ctgaggtata     2400
atctgtgtgg aaaacacgct agcaaagtct ctctcagtat tcacacatga agtagctaa      2460
gaataaaatc tattcatctg ttttttcctta aaatcctggc tacagtgttg actcagtggt     2520
tgctttaaat tttatgctca aaagttgaag cagcttttt gaaccggtaa ttctactttg      2580
tattaaatac ttgttatgca tcgctcaaca aatcaagttt taacacacca aatcttgccc     2640
tttttgtgta tcttaaattt tttaaatggg cataaattgc agctattcct acagaagtca     2700
gttcttcagt acaactgaaa atgcattcct gatttatgta aatatatgta tatacatata     2760
tagccttaaa aacaaagatt gtaatttta taaattgtga tttttaaaaa aataaacctg      2820
cattatcttc agcaggaggc tgcctgaatg ttcctaagtt ttgtagaact tgacacgtgg     2880
cagagggcaa caggatttta gtctacacct gcatctgagg acagagcagg               2930
```

<210> SEQ ID NO 28
<211> LENGTH: 414
<212> TYPE: DNA
<213> ORGANISM: Hamster sp.

```
<400> SEQUENCE: 28
ttgaggggga tctaggtttc ttccaggttc tggctattgc aaataaccct gctatgaaca      60
tagctgaaca tatgtcatta ttgtatgaat ctgttttaca tattttaaac catctctaga     120
ttgcttgtaa tattgttaaa catagagagt aataatgcta taaaaattaa aaataatgat     180
aagaaagatc ctatacatgt tcagtacaga tgaaaattta gaaatacttt agctaccact     240
gacgaaattt gtatgtgcag aatgtctgga attaaagaaa ttactgttct ttatataata     300
atagactgta aaatggcaac ttttaaaata tttgctaatt cacaggattt tttctttgga     360
acatctgaac aaatttccct tatatgaatc acttacattt ttgcctgttc attt           414

<210> SEQ ID NO 29
<211> LENGTH: 813
<212> TYPE: DNA
<213> ORGANISM: Hamster sp.

<400> SEQUENCE: 29
ttgaggggga tctaggtttc ttccaggttc tggctattgc aaataaccct gctatgaaca      60
tagctgaaca tatgtcatta ttgtatgaat ctgttttaca tattttaaac catctctaga     120
ttgcttgtaa tattgttaaa catagagagt aataatgcta taaaaattaa aaataatgat     180
aagaaagatc ctatacatgt tcagtacaga tgaaaattta gaaatacttt agctaccact     240
gacgaaattt gtatgtgcag aatgtctgga attaaagaaa ttactgttct ttatataata     300
atagactgta aaatggcaac ttttaaaata tttgctaatt cacaggattt tttctttgga     360
acatctgaac aaatttccct tatatgaatc acttacattt ttgcctgttc atttaaaaaa     420
ctgcaggaaa gttgtgattt ataatgcaac tgcacagcag ccagtcttaa acaatgctaa     480
ccactgtgtt tcagcataaa cttcccacac agtcatacag actatgaaaa cacatgctta     540
aaggcaaatc tttacctcag ttaactattc catagagcca ttgagttcaa gtgcatttag     600
aagatataat gtctatggcc atatatatat atatatatat atatatatat atatatatat     660
atatatatat atcagcacag tggaaacagt taataacatt ttagcatata tactatagaa     720
aataggaggc tggaaggggg ctcagcagtt aatagcacat actattcttc cagaagacta     780
aggtttggtt ttcatcaccc atgtcaggtg gtt                                  813

<210> SEQ ID NO 30
<211> LENGTH: 1576
<212> TYPE: DNA
<213> ORGANISM: Hamster sp.

<400> SEQUENCE: 30
ttgaggggga tctaggtttc ttccaggttc tggctattgc aaataaccct gctatgaaca      60
tagctgaaca tatgtcatta ttgtatgaat ctgttttaca tattttaaac catctctaga     120
ttgcttgtaa tattgttaaa catagagagt aataatgcta taaaaattaa aaataatgat     180
aagaaagatc ctatacatgt tcagtacaga tgaaaattta gaaatacttt agctaccact     240
gacgaaattt gtatgtgcag aatgtctgga attaaagaaa ttactgttct ttatataata     300
atagactgta aaatggcaac ttttaaaata tttgctaatt cacaggattt tttctttgga     360
acatctgaac aaatttccct tatatgaatc acttacattt ttgcctgttc atttaaaaaa     420
ctgcaggaaa gttgtgattt ataatgcaac tgcacagcag ccagtcttaa acaatgctaa     480
ccactgtgtt tcagcataaa cttcccacac agtcatacag actatgaaaa cacatgctta     540
```

```
aaggcaaatc tttacctcag ttaactattc catagagcca ttgagttcaa gtgcatttag        600
aagatataat gtctatggcc atatatatat atatatatat atatatatat atatatatat        660
atatatatat atcagcacag tggaaacagt taataacatt ttagcatata tactatagaa        720
aataggaggc tggaagggg ctcagcagtt aatagcacat actattcttc cagaagacta         780
aggtttggtt ttcatcaccc atgtcaggtg gttcatttct atctgtaacc agatgatacg        840
atgccctcta gtccccttgg gtacctctat cacctgctat tctcacccaa agacacacac        900
actcacatac acatgttcat ggacacatgc atgcacatag ttcaaaaaat aaaattttaa        960
aaggaaaaaa agctcaaatc tttttttgaag agtcttaaaa ttcctatgag tgtgtgatca     1020
aagtcagtat actattctga ggtataatct gtgtggaaaa cacgctagca aagtctctct       1080
cagtattcac acatgaaagt agctaagaat aaaatctatt catctgtttt tccttaaaat      1140
cctggctaca gtgttgactc agtggttgct ttaaattta tgctcaaaag ttgaagcagc       1200
ttttttgaac cggtaattct actttgtatt aaatacttgt tatgcatcgc tcaacaaatc      1260
aagttttaac acaccaaatc ttgccctttt tgtgtatctt aaatttttta aatgggcata     1320
aattgcagct attcctacag aagtcagttc ttcagtacaa ctgaaaatgc attcctgatt     1380
tatgtaaata tatgtatata catatatagc cttaaaaaca aagattgtaa ttttttataaa   1440 ttgtgattt taaaaaaata aacctgcatt atcttcagca ggaggctgcc tgaatgttcc      1500
taagttttgt agaacttgac acgtggcaga gggcaacagg attttagtct acacctgcat    1560
ctgaggacag agcagg                                                                1576

<210> SEQ ID NO 31
<211> LENGTH: 1783
<212> TYPE: DNA
<213> ORGANISM: Hamster sp.

<400> SEQUENCE: 31
ttgaggggga tctaggtttc ttccaggttc tggctattgc aaataaccct gctatgaaca         60
tagctgaaca tatgtcatta ttgtatgaat ctgttttaca tattttaaac catctctaga       120
ttgcttgtaa tattgttaaa catagagagt aataatgcta taaaaattaa aaataatgat      180
aagaaagatc ctatacatgt tcagtacaga tgaaaattta gaaatacttt agctaccact       240
gacgaaattt gtatgtgcag aatgtctgga attaaagaaa ttactgttct ttatataata     300
atagactgta aaatggcaac ttttaaaata tttgctaatt cacaggattt tttctttgga      360
acatctgaac aaatttccct tatatgaatc acttacattt ttgcctgttc atttaaaaaa     420
ctgcaggaaa gttgtgattt ataatgcaac tgcacagcag ccagtcttaa acaatgctaa     480
ccactgtgtt tcagcataaa cttcccacac agtcatacag actatgaaaa cacatgctta    540
aaggcaaatc tttacctcag ttaactattc catagagcca ttgagttcaa gtgcatttag      600
aagatataat gtctatggcc atatatatat atatatatat atatatatat atatatatat        660
atatatatat atcagcacag tggaaacagt taataacatt ttagcatata tactatagaa        720
aataggaggc tggaagggg ctcagcagtt aatagcacat actattcttc cagaagacta         780
aggtttggtt ttcatcaccc atgtcaggtg gttcatttct atctgtaacc agatgatacg        840
atgccctcta gtccccttgg gtacctctat cacctgctat tctcacccaa agacacacac        900
actcacatac acatgttcat ggacacatgc atgcacatag ttcaaaaaat aaaattttaa        960
aaggaaaaaa agctcaaatc tttttttgaag agtcttaaaa ttcctatgag tgtgtgatca     1020
aagtcagtat actattctga ggtataatct gtgtggaaaa cacgctagca aagtctctct       1080
```

```
cagtattcac acatgaaagt agctaagaat aaaatctatt catctgtttt tccttaaaat    1140
cctggctaca gtgttgactc agtggttgct ttaaatttta tgctcaaaag ttgaagcagc    1200
ttttttgaac cggtaattct actttgtatt aaatacttgt tatgcatcgc tcaacaaatc    1260
aagttttaac acaccaaatc ttgccctttt tgtgtatctt aaatttttta aatgggcata    1320
aattgcagct attcctacag aagtcagttc ttcagtacaa ctgaaaatgc attcctgatt    1380
tatgtaaata tatgtatata catatatagc cttaaaaaca aagattgtaa ttttttataaa   1440 ttgtgatttt taaaaaaata aacctgcatt atcttcagca ggaggctgcc tgaatgttcc    1500
taagttttgt agaacttgac acgtggcaga gggcaacagg attttagtct acacctgcat    1560
ctgaggacag agcaggccta acaggaaagg agacacatgt gtggtagttc ccagttttga    1620
cgtgaaaagt cctgcattct tactggaaac ctccctgaat ccatgccaag cactacccat    1680
caccttgact ggcataagca ctcactcatt tcctttgatg cccctccctc agatcctatt    1740
ataaaagcac agtcgtctct ttcctggcaa aacaccccag atc                     1783

<210> SEQ ID NO 32
<211> LENGTH: 399
<212> TYPE: DNA
<213> ORGANISM: Hamster sp.

<400> SEQUENCE: 32
aaaaaactgc aggaaagttg tgatttataa tgcaactgca cagcagccag tcttaaacaa     60
tgctaaccac tgtgtttcag cataaacttc ccacacagtc atacagacta tgaaaacaca    120
tgcttaaagg caaatcttta cctcagttaa ctattccata gagccattga gttcaagtgc    180
atttagaaga tataatgtct atggccatat atatatatat atatatatat atatatatat    240
atatatatat atatatatca gcacagtgga aacagttaat aacatttag catatatact     300 atagaaaata ggaggctgga aggggctca gcagttaata gcacatacta ttcttccaga    360
agactaaggt ttggttttca tcacccatgt caggtggtt                           399

<210> SEQ ID NO 33
<211> LENGTH: 1162
<212> TYPE: DNA
<213> ORGANISM: Hamster sp.

<400> SEQUENCE: 33
aaaaaactgc aggaaagttg tgatttataa tgcaactgca cagcagccag tcttaaacaa     60
tgctaaccac tgtgtttcag cataaacttc ccacacagtc atacagacta tgaaaacaca    120
tgcttaaagg caaatcttta cctcagttaa ctattccata gagccattga gttcaagtgc    180
atttagaaga tataatgtct atggccatat atatatatat atatatatat atatatatat    240
atatatatat atatatatca gcacagtgga aacagttaat aacatttag catatatact     300 atagaaaata ggaggctgga aggggctca gcagttaata gcacatacta ttcttccaga    360
agactaaggt ttggttttca tcacccatgt caggtggttc atttctatct gtaaccagat    420
gatacgatgc cctctagtcc ccttgggtac ctctatcacc tgctattctc acccaaagac    480
acacacactc acatcacat gttcatggac acatgcatgc acatagttca aaaataaaa     540 ttttaaaagg aaaaaaagct caaatctttt ttgaagagtc ttaaaattcc tatgagtgtg    600
tgatcaaagt cagtatacta ttctgaggta taatctgtgt ggaaaacacg ctagcaaagt    660
ctctctcagt attcacacat gaaagtagct aagaataaaa tctattcatc tgttttcct    720
```

```
taaaatcctg gctacagtgt tgactcagtg gttgctttaa attttatgct caaaagttga      780
agcagctttt ttgaaccggt aattctactt tgtattaaat acttgttatg catcgctcaa      840
caaatcaagt tttaacacac caaatcttgc ccttttttgtg tatcttaaat tttttaaatg     900
ggcataaatt gcagctattc ctacagaagt cagttcttca gtacaactga aaatgcattc      960
ctgatttatg taaatatatg tatatacata tatagcctta aaaacaaaga ttgtaatttt     1020
tataaattgt gattttttaaa aaaataaacc tgcattatct tcagcaggag gctgcctgaa    1080
tgttcctaag ttttgtagaa cttgacacgt ggcagagggc aacaggattt tagtctacac     1140
ctgcatctga ggacagagca gg                                              1162

<210> SEQ ID NO 34
<211> LENGTH: 1369
<212> TYPE: DNA
<213> ORGANISM: Hamster sp.

<400> SEQUENCE: 34
aaaaaactgc aggaaagttg tgatttataa tgcaactgca cagcagccag tcttaaacaa       60
tgctaaccac tgtgtttcag cataaacttc ccacacagtc atacagacta tgaaaacaca      120
tgcttaaagg caaatcttta cctcagttaa ctattccata gagccattga gttcaagtgc      180
atttagaaga tataatgtct atggccatat atatatatat atatatatat atatatatat      240
atatatatat atatatatca gcacagtgga aacagttaat aacattttag catatatact      300
atagaaaata ggaggctgga aggggctca gcagttaata gcacatacta ttcttccaga       360
agactaaggt ttggttttca tcacccatgt caggtggttc atttctatct gtaaccagat      420
gatacgatgc cctctagtcc ccttgggtac ctctatcacc tgctattctc acccaaagac      480
acacacactc acatacacat gttcatggac acatgcatgc acatagttca aaaaataaaa      540
ttttaaaagg aaaaaaagct caaatctttt ttgaagagtc ttaaaattcc tatgagtgtg      600
tgatcaaagt cagtatacta ttctgaggta taatctgtgt ggaaaacacg ctagcaaagt      660
ctctctcagt attcacacat gaaagtagct aagaataaaa tctattcatc tgttttttcct   720 taaaatcctg gctacagtgt tgactcagtg gttgctttaa attttatgct caaaagttga      780
agcagctttt ttgaaccggt aattctactt tgtattaaat acttgttatg catcgctcaa      840
caaatcaagt tttaacacac caaatcttgc ccttttttgtg tatcttaaat tttttaaatg     900
ggcataaatt gcagctattc ctacagaagt cagttcttca gtacaactga aaatgcattc      960
ctgatttatg taaatatatg tatatacata tatagcctta aaaacaaaga ttgtaatttt     1020
tataaattgt gattttttaaa aaaataaacc tgcattatct tcagcaggag gctgcctgaa    1080
tgttcctaag ttttgtagaa cttgacacgt ggcagagggc aacaggattt tagtctacac     1140
ctgcatctga ggacagagca ggcctaacag gaaaggagac acatgtgtgg tagttcccag     1200
ttttgacgtg aaaagtcctg cattcttact ggaaacctcc ctgaatccat gccaagcact     1260
acccatcacc ttgactggca taagcactca ctcatttcct ttgatgcccc tccctcagat     1320
cctattataa aagcacagtc gtctctttcc tggcaaaaca ccccagatc                1369

<210> SEQ ID NO 35
<211> LENGTH: 763
<212> TYPE: DNA
<213> ORGANISM: Hamster sp.

<400> SEQUENCE: 35
catttctatc tgtaaccaga tgatacgatg ccctctagtc cccttgggta cctctatcac       60
```

```
ctgctattct cacccaaaga cacacacact cacatacaca tgttcatgga cacatgcatg      120
cacatagttc aaaaaataaa attttaaaag gaaaaaaagc tcaaatcttt tttgaagagt      180
cttaaaattc ctatgagtgt gtgatcaaag tcagtatact attctgaggt ataatctgtg      240
tggaaaacac gctagcaaag tctctctcag tattcacaca tgaaagtagc taagaataaa      300
atctattcat ctgttttttcc ttaaaatcct ggctacagtg ttgactcagt ggttgcttta      360
aattttatgc tcaaaagttg aagcagcttt tttgaaccgg taattctact ttgtattaaa      420
tacttgttat gcatcgctca acaaatcaag ttttaacaca ccaaatcttg ccctttttgt      480
gtatcttaaa ttttttaaat gggcataaat tgcagctatt cctacagaag tcagttcttc      540
agtacaactg aaaatgcatt cctgatttat gtaaatatat gtatacacat atatagcctt      600
aaaaacaaag attgtaattt ttataaattg tgattttttaa aaaaataaac ctgcattatc      660
ttcagcagga ggctgcctga atgttcctaa gttttgtaga acttgacacg tggcagaggg      720
caacaggatt ttagtctaca cctgcatctg aggacagagc agg                       763

<210> SEQ ID NO 36
<211> LENGTH: 970
<212> TYPE: DNA
<213> ORGANISM: Hamster sp.

<400> SEQUENCE: 36
catttctatc tgtaaccaga tgatacgatg ccctctagtc cccttgggta cctctatcac       60
ctgctattct cacccaaaga cacacacact cacatacaca tgttcatgga cacatgcatg      120
cacatagttc aaaaaataaa attttaaaag gaaaaaaagc tcaaatcttt tttgaagagt      180
cttaaaattc ctatgagtgt gtgatcaaag tcagtatact attctgaggt ataatctgtg      240
tggaaaacac gctagcaaag tctctctcag tattcacaca tgaaagtagc taagaataaa      300
atctattcat ctgttttttcc ttaaaatcct ggctacagtg ttgactcagt ggttgcttta      360
aattttatgc tcaaaagttg aagcagcttt tttgaaccgg taattctact ttgtattaaa      420
tacttgttat gcatcgctca acaaatcaag ttttaacaca ccaaatcttg ccctttttgt      480
gtatcttaaa ttttttaaat gggcataaat tgcagctatt cctacagaag tcagttcttc      540
agtacaactg aaaatgcatt cctgatttat gtaaatatat gtatacacat atatagcctt      600
aaaaacaaag attgtaattt ttataaattg tgattttttaa aaaaataaac ctgcattatc      660
ttcagcagga ggctgcctga atgttcctaa gttttgtaga acttgacacg tggcagaggg      720
caacaggatt ttagtctaca cctgcatctg aggacagagc aggcctaaca ggaaaggaga      780
cacatgtgtg gtagttccca gttttgacgt gaaaagtcct gcattcttac tggaaacctc      840
cctgaatcca tgccaagcac tacccatcac cttgactggc ataagcactc actcatttcc      900
tttgatgccc ctccctcaga tcctattata aaagcacagt cgtctctttc ctggcaaaac      960
accccagatc                                                            970

<210> SEQ ID NO 37
<211> LENGTH: 207
<212> TYPE: DNA
<213> ORGANISM: Hamster sp.

<400> SEQUENCE: 37
cctaacagga aggagacac atgtgtggta gttcccagtt tgacgtgaa aagtcctgca        60 ttcttactgg aaacctccct gaatccatgc caagcactac ccatcacctt gactggcata     120
```

-continued

```
agcactcact catttccttt gatgccccte cctcagatcc tattataaaa gcacagtcgt    180
ctctttcctg gcaaaacacc ccagatc                                        207

<210> SEQ ID NO 38
<211> LENGTH: 332
<212> TYPE: DNA
<213> ORGANISM: Hamster sp.

<400> SEQUENCE: 38
aaaaaaataa acctgcatta tcttcagcag gaggctgcct gaatgttcct aagttttgta     60
gaacttgaca cgtggcagag ggcaacagga ttttagtcta cacctgcatc tgaggacaga    120
gcaggcctaa caggaaagga gacacatgtg tggtagttcc cagttttgac gtgaaaagtc    180
ctgcattctt actggaaacc tccctgaatc catgccaagc actacccatc accttgactg    240
gcataagcac tcactcattt cctttgatgc ccctccctca gatcctatta taaaagcaca    300
gtcgtctctt tcctggcaaa acaccccaga tc                                  332
```